US006767719B1

(12) United States Patent
Morin et al.

(10) Patent No.: US 6,767,719 B1
(45) Date of Patent: *Jul. 27, 2004

(54) MOUSE TELOMERASE REVERSE TRANSCRIPTASE

(75) Inventors: Gregg B. Morin, Palo Alto, CA (US); Richard Allsopp, Mountain View, CA (US); Ronald A. DePinho, Pelham Manor, NY (US); Roger A. Greenberg, Bronx, NY (US)

(73) Assignees: Geron Corporation, Menlo Park, CA (US); Albert Einstein College of Medicine of Yeshiva University, a division of Yeshiva University, Bronx, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/042,460

(22) Filed: Mar. 16, 1998

Related U.S. Application Data

(63) Continuation-in-part of application No. 08/979,742, filed on Nov. 26, 1997, now abandoned.

(51) Int. Cl.[7] .......................... C12P 21/06; C12N 5/00; C12N 15/63; C07H 21/04; C07K 1/00

(52) U.S. Cl. ................... 435/69.1; 435/320.1; 435/325; 435/455; 536/23.1; 536/23.5; 530/350

(58) Field of Search ............................ 435/69.1, 320.1, 435/325, 455; 536/23.1, 23.5, 23.7; 530/350; 800/3, 13, 18

(56) References Cited

U.S. PATENT DOCUMENTS

| 6,337,200 B1 | 1/2002 | Morin ......................... 435/194 |
| 2003/0060417 A1 | 3/2003 | Tsuchiya et al. ............... 514/12 |

FOREIGN PATENT DOCUMENTS

| WO | WO/9735967 | * 10/1997 |
| WO | WO 97/35967 | 10/1997 |
| WO | WO97/35967 | * 10/1997 |
| WO | PCT/US/98/25211 | 11/1998 |
| WO | WO 99/35261 | 7/1999 |
| WO | WO 02/74935 | 9/2002 |

OTHER PUBLICATIONS

Ngo, Computational complexity Protein structure prediction and the Levinthal paradox in The Protein Folding Problem and Tertiary Structure Prediction, Merz et al. (eds.), Birkhuaser Boston: Boston, MA, pp. 433 and 492–495, 1994.*

Rudinger Characteristics of amino acids as components of a peptide hormone sequence (in Peptide Hormones, Parsons (ed.), University Park Press: Baltimore, MD, pp. 1–7, 1976).*

PTO Sequence Search report ACC. NO. AF015950, Science 277:955–959, 1997.*

Rosenberg et al., Gene therapist, Heal thyself, 2000, Science, vol. 287, pp. 1751.*

Friedmann, Principles for human gene therapy studies, 2000, Science, vol. 287, pp. 2163–2164.*

Anderson, Human gene therapy, 1998,Nature, vol. 392, pp. 25–30.*

Verma et al., Gene therapy–promises,problems and prospects, 1997, Nature, vol. 389, pp. 239–242.*

Ngo, in The Protein Folding Problem and Tertiary Structure Prediction, Merz et al. (eds.), Birkhauser Boston: Boston, MA, pp. 433 and 492–495, 1994.*

Rudinger, in Peptide Hormones, Parsons (ed.), University Park Press: Baltimore, MD, pp. 1–7, 1976.*

Lundblad, PNAS 95:8415–8416, 1998.*

Rossant et al , Phil. Trans. R. Soc Lond. B. 339:137–254, 1993.*

PTO Sequence Search report ACC. NO. AF015950, Science 277:955–959, 1997.*

Nakamura et al.; *Telomerase Catalytic Subunit Homologs from Fission Yeast and Human*, Science vol. 277, Aug. 1997, pp. 955–959.

Meyerson et al. *Hest2 the Putative Human Telomerase Catalytic Subunit Gene, Is Up–Regulated in Tumor Cells and during Immortalization*, Cell vol. 90, Aug. 1997, pp. 785–795.

Bryan TM, Sperger JM, Chapman KB, Cech TR. Telomerase reverse transcriptasc genes identified in Tetrahymena thermophila and Oxytricha trifallax. Proc Natl Acad Sci U S A. Jul. 21, 1998; 95(15):8479–84.

Collins K, Gandhi L. The reverse transcriptase component of the Tetrahymena telomerase ribonucleoptroein complex. Proc Natl Acad Sci U S A . Jul. 21, 1998;95(15):8485–90.

Counter CM, Meyerson M, Eaton EN, Weinberg RA. The catalytic subunit of yeast telomerase. Proc Natl Acad Sci USA. Aug. 19, 1997;94(17):9202–7.

Friedman KL, Cech TR. Essential functions of amino–terminal domians in the yeast telomerase catalytic subunit revealed by selection for viable mutants. Genes Dev. Nov. 1, 1999;13(21):2863–74.

(List continued on next page.)

*Primary Examiner*—Jeffrey Fredman
*Assistant Examiner*—Sumesh Kaushal
(74) *Attorney, Agent, or Firm*—J. Michael Schiff; David J. Earp

(57) ABSTRACT

This invention provides for murine telomerase reverse transcriptase (mTERT) enzyme proteins and nucleic acids, including methods for isolating and expressing these nucleic acids and proteins, which have application to the control of cell proliferation and aging, including the control of age-related diseases, such as cancer.

21 Claims, 16 Drawing Sheets-

OTHER PUBLICATIONS

Greenberg RA, Allsopp RC, Chin L, Morin GB, DePinho RA. Expression of mouse telomerase reverse transcriptase during development, differentiation and proliferation. Oncogene. Apr. 2, 1998;16(13):1723–30.

Lingner J, Hughes TR, Shevchenko A, Mann M, Lundblad V, Cech TR, Reverse transcriptase motifs in the catalytic subunit of telomerase. Science. Apr. 25, 1997;276(5312):561–7.

Patel PH, Loeb LA. DNA polymerase active site is highly mutable: evolutionary consequences. Proc Natl Acad Sci U S A. May 9, 2000;97(10):5095–100.

Stemmer WP. DNA shuffling by random fragmentation and reassembly: in vitro recombination for molecular evolution. Proc Natl Acad Sci U S A. Oct. 25, 1994;91(22):10747–51.

Weinrich SL, Pruzan R, Ma L, Ouellette M, Tesmer VM, Holt SE, Bodnar AG, Lichtsteiner S, Kim NW, Trager JB, Taylor RD, Carlos R, Andrews WH, Wright WE, Shay JW, Harley CB, Morin GB. Reconstitution of human telomerase with the template RNA component hTR and the catalytic protein subunit hTRT. Nat Genet. Dec. 1997;17(4):498–502.

Xiong Y, Eickbush TH. Origin and evolution of retroelements based upon their reverse transcriptase sequences. EMBO J. Oct. 1990;9(10):3353–62.

Blasco MA, et al. Telomere shortening and tumor formation by mouse cells lacking telomerase RNA. Cell. Oct. 3, 1997;91(1):25–34.

Blasco MA, et al. Mouse models for the study of telomerase. Ciba Found Symp. 1997;211:160–70; discussion 170–6.

Lansdorp PM. Lessons from mice without telmoerase. J Cell Biol. Oct. 20, 1997;139(2):309–12.

Kipling D. Telomere structure and telomerase expression during mouse development and tumorigenesis. Eur J Cancer. Apr. 1997;33(5):792–800.

* cited by examiner

FIGURE 1
page 1 of 3 mTRT cDNA clone
- 3496 base pairs
- cDNA: nucleotides 10 to 3435
- ORF: nucleotides 39 to 3404

```
GAATTCCGGG TGGGAGGCCC ATCCCGGCCT TGAGCACAAT GACCCGCGCT        50
CCTCGTTGCC CCGCGGTGCG CTCTCTGCTG CGCAGCCGAT ACCGGGAGGT       100
GTGGCCGCTG GCAACCTTTG TGCGGCGCCT GGGGCCCGAG GGCAGGCGGC       150
TTGTGCAACC CGGGGACCCG AAGATCTACC GCACTTTGGT TGCCCAATGC       200
CTAGTGTGCA TGCACTGGGG CTCACAGCCT CCACCTGCCG ACCTTTCCTT       250
CCACCAGGTG TCATCCCTGA AAGAGCTGGT GGCCAGGGTT GTGCAGAGAC       300
TCTGCGAGCG CAACGAGAGA AACGTGCTGG CTTTTGGCTT TGAGCTGCTT       350
AACGAGGCCA GAGGCGGGCC TCCCATGGCC TTCACTAGTA GCGTGCGTAG       400
CTACTTGCCC AACACTGTTA TCCCAGACCCT GCGTGTCAGT GGTGCATGGA       450
TGCTACTGTT GAGCCGAGTG TGCTGGTCTA CCTGCTGGCA       500
CACTGTGCTC TTTATCTTCT AGCTGTGCCT ACCAGGTGTG       550
TGGGTCTCCC CTGTACCAAA TTTGTGCCAC CACGGATATC TGGCCCCTG       600
TGTCCGCTAG TTACAGGCCC ACCCGACCCG TGGGCAGGAA TTTCACTAAC       650
CTTAGGTTCT TACAACAGAT CAAGAGCAGT AGTCGCGCAGG AAGCACCGAA       700
ACCCCTGGCC TTGCCATCTC GAGGTACAAA GAGGCATCTG AGTCTCACCA       750
GTACAAGTGT GCCTTCAGCT AAGAAGGCCA GATGCTATCC TGTCCCGAGA       800
GTGGAGGAGG GACCCCACAG GCAGGTGCTA CCAACCCCAT CAGGCAAATC       850
ATGGGTGCCA AGTCCCTGCTC GGTCCCCCGA GGTGCCTACT GCAGAGAAAG       900
ATTTGTCTTC TAAAGGAAAG GTGTCTGACC TGAGTCTCTC TGGGTCGGTG       950
TGCTGTAAAC ACAAGCCCAG CTCCACATCT CTGCTGTCAC CACCCCGCCA      1000
AAATGCCTTT CAGCTCAGGC CATTTATTGA GACCAGACAT TTCCTTTACT      1050
CCAGGGGAGA TGGCCAAGAG CGTCTAAACC CCTCATTCCT ACTCAGCAAC      1100
CTCCAGCCTA ACTTGACTGG GGCCAGGAGA CTGGTGGAGA TCATCTTTCT      1150
GGGCTCAAGG CCTAGGACAT CAGGACCACT CTGCAGGACA CACCGTCTAT      1200
```

FIGURE 1
page 2 of 3 mTR1 cDNA clone
- 3496 base pairs
- cDNA: nucleotides 10 to 3435
- ORF: nucleotides 39 to 3404

```
CGCGTCGATA CTGGCAGATG CGGCCCCTGT TCCAACAGCT GCTGGTGAAC 1250
CATGCAGAGT GCCAATATGT CAGACTCCTC AGGTCACATT GCAGGTTTCG 1300
AACAGCAAAC CAACAGGTGA CAGATGCCTT GAACACCAGC CCACCGCACC 1350
TCATGGATTT GCTCCGCCTG CACAGCAGTC CCTGGCAGGT ATATGGTTTT 1400
CTTCGGGCCT GTCTCTGCAA GGTGGTGTCT GCTAGTCTCT GGGGTACCAG 1450
GCACAATGAG CGCCGCTTCT TTAAGAACTT AAAGAAGTTC ATCTCGTTGG 1500
GGAAATACGG CAAGCTATCA CTGCAGGAAC TGATGTGGAA GATGAAAGTA 1550
GAGGATTGCC ACTGGCTCCG CAGCAGCCCG GGGAAGGACC GTGTCCCCGC 1600
TGCAGAGCAC CGTCTGAGGG AGAGGATCCT GGCTACGTTC CTGTTCTGGC 1650
TGATGGACAC ATACGTGGTA CAGCTGCTTA GGTCATTCTT TTACATCACA 1700
GAGAGCACAT TCCAGAAGAA CAGGCTCTTC TTCTACCGTA AGAGTGTGTG 1750
GAGCAAGCTG CAGAGCATTG GAGTCAGGCA ACACCTTGAG AGAGTGCGGC 1800
TACGGGAGCT GTCACAAGAG GAGGTCAGGC ATCACCAGGA CACCTGGCTA 1850
GCCATGCCCA TCTGCAGACT GCGCTTCATC CCCAAGCCCA ACGGCCTGCG 1900
GCCCATTGTG AACATGAGTT ATAGCATGGG TACCAGAGCT TTGGGCAGAA 1950
GGAAGCAGGC CCAGCATTTC ACCCAGCGTC TCAAGACTCT CTTCAGCATG 2000
CTCAACTATG AGCGGACAAA ACATCCTCAC CTTATGGGGT CTTCTGTACT 2050
GGGTATGAAT GACATCTACA GGACCTGGCG GGCCTTTGTG CTGCGTGTGC 2100
GTGCTCTGGA CCAGACACCC AGGATGTACT TTGTTAAGGC AGATGTGACC 2150
GGGCCTATG ATGCCATCCC CCAGGGTAAG CTGGTGGAGG TTGTTGCCAA 2200
TATGATCAGG CACTCGGAGA CCAGGTACTG TATCCGCCAG TATGCAGTGG 2250
TCCGGAGAGA TAGCCAAGGC GCACGTACTG AGTCCTTTAG GAGACAGGTC 2300
ACCACCCTCT CTGACCTCCA CAAGTCCACA GGCCAGTTCC TTAAGCATCT 2350
GCAGGATTCA GATGCCAGTG CACTGAGGAA CTCCGTTGTC ATCGAGCAGA 2400
```

FIGURE 1
page 3 of 3 mTRT cDNA clone
- 3496 base pairs
- cDNA: nucleotides 10 to 3435
- ORF: nucleotides 39 to 3404

```
GCATCTCTAT GAATGAGAGC AGCAGCAGCC TGTTTGACTT CTTCCTGCAC    2450
TTCCTGCGTC ACAGTGTCGT AAAGATTGGT GACAGGTGCT ATACGCAGTG    2500
CCAGGGCATC CCCCAGGGCT CCAGCCTATC CACCCTGCTC TGCAGTCTGT    2550
GTTTCGGAGA CATGGAGAAC AAGCTGTTTG CTGAGGTGCA GCGGGATGGG    2600
TTGCTTTTAC GTTTTGTTGA TGACTTTCTG TTGGTGACGC CTCACTTGGA    2650
CCAAGCAAAA ACCTTCCTCA GCACCCTGGT CCATGGCGTT CCTGAGTATG    2700
GGTGCATGAT AAACTTGCAG AAGACAGTGG TGAACTTCCC TGTGGAGCCT    2750
GGTACCCTGG GTGGTGCAGC TCCATACCAG CTGCCTGCTC ACTGCCTGTT    2800
TCCCTGGTGT GGCTTGCTGC TGGACACTCA GACTTTGGAG GTGTTCTGTG    2850
ACTACTCAGG TTATGCCCAG ACCTCAATTA AGACGAGCCT CACCTTCCAG    2900
AGTGTCTTCA AAGCTGGGAA GAACAAGCGG AACAAGCTCC TGTCGGTCTT    2950
GCGGTTGAAG TGTCACGGTC TATTTCTAGA CTTGCAGGTG AACAGCCTCC    3000
AGACAGTCTG CATCAATATA TACAAGATCT TCCTGCTTCA GGCCTACAGG    3050
TTCCATGCAT GTGTGATTCA GCTTCCCTTT GACCAGCGTG TTAGGAAGAA    3100
CCTCACATTC TTTCTGGGCA TCATCTCCAG CCAAGCATCC TGCTGCTATG    3150
CTATCCTGAA GGTCAAGAAT CCAGGAATGA CACTAAAGGC CTCTGCCTCC    3200
TTTCCTCCTG AAGCCGCACA TGGCTCTGC TACCAGGCCT TCCTGCTCAA    3250
GCTGGCTGCT CATTCTGTCA TCTACAAATG TCTCCTGGGA CCTCTGAGGA    3300
CAGCCCAAAA ACTGCTGTGC GGAAGCTCC CAGAGGCGAC AATGACCATC    3350
CTTAAAGCTG CAGCTGACCC AGCCCTAAGC ACAGACTTTC AGACCATTTT    3400
GGACTAACCC TGTCTCCTTC CGCTAGATGA ACATGAAGGG CGAATTCCAG    3450
CACACTGGCG GCCGTTACTA GTGGATCCGA GCTCGGTACC      AAGCTT    3496
```

FIGURE 2

1122 Amino Acids
127,979 kD
pI ~ 10.4

```
MTRAPRCPAV RSLLRSRYRE VWPLATFVRR LGPEGRRLVQ PGDPKIYRTL VAQCLVCMHW GSQPPPADLS FHQVSSLKEL   80
VARVVQRLCE RNERNVLAFG FELLNEARGG PPMAFTSSVR SYLPNTVIET LRVSGAWMLL LSRVGDDLLV YLLAHCALYL  160
LVPPSCAYQV CGSPLYQICA TTDIWPSVSA SYRPTRPVGR NFTNLRFLQQ IKSSSRQEAP KPLALPSRGT KRHLSLTSTS  240
VPSAKKARCY PVPRVEEGPH RQVLPTPSGK SWVPSPARSP EVPTAEKDLS SKGKVSDLSL SGSVCCKHKP SSTSLLSPPR  320
QNAFQLRPFI ETRHFLYSRG DGQERLNPSF LLSNLQPNLT GARRLVEIF  LGSRPRTSGP LCRTHRLSRR YWQMRPLFQQ  400
LLVNHAECQY VRLLRSHCRF RTANQQVTDA LNTSPPHLMD LLRLHSSPWQ VYGFLRACLC KVVSASLWGT RHNERRFFKN  480
LKKFISLGKY GKLSLQELMW KMKVEDCHWL RSSPGKDRVP AAEHRLRERI LATFLFWLMD TYVVQLIRSF FYITESTFQK  560
NRLFFYRKSV WSKLQSIGVR QHLERVRLRE LSQEEVRHHQ DTWLAMPICR LRFIPKPNGL RPIVNMSYSM GTRALGRRKQ  640
AQHFTQRLKT LFSMLNYERT KHPHLMGSSV LGMNDIYRTW RAFVLRVRAL DQTPRMYFVK ADVTGAYDAI PQGKLVEVVA  720
NMIRHSESTY CIRQYAVVRR DSQGQVHKSF RRQVTTLSDL QPYMGQFLKH LQDSDASALR NSVVIEQSIS MNESSSSLFD  800
FFLHFLRHSV VKIGDRCYTQ CQGIPQGSSL STLLCSLCFG DMENKLFAEV QRDGLLLRFV DDFLLVTPHL DQAKTFLSTL  880
VHGVPEYGCM INLQKTVVNF PVEPGTLGGA APYQLPAHCL FPWCGLLLDT QTLEVFCDYS GYAQTSIKTS LTFQSVFKAG  960
KTMRNKLLSV LRLKCHGLFL DLQVNSLQTV CINIYKIFLL QAYRFHACVI QLPFDQRVRK NLTFFLGIIS SQASCCYAIL 1040
KVKNPGMTLK ASGSFPPEAA HWLCYQAFLL KLAAHSVIYK CLLGPLRTAQ KLLCRKLPEA TMTILKAAAD PALSTDFQTI 1120
LD                                                                                     1122
```

FIGURE 3
page 1 of 3 mTRT vs. hTRT amino acid alignment mTRT MTRAPRCPAVRSLLRSRYREVWPLATFVRRLGPEGRRLVQPGDPKIYRTLVAQCLVCMHWGSQPPPADLSFHQVS
hTRT MPRAPRCRAVRSLLRSHYREVLPLATFVRRLGPQGWRLVQRGDPAAFRALVAQCLVCVPWDARPPPAAPSFRQVS

SLKELVARVVQRLCERNERNVLAFGFELLNEARGGPPMAFTSSVRSYLPNTVIETLRVSGAWMLLL SRVGDDLLV
CLKELVARVLQRLCERGAKNVLAFGFALLDGARGGPPEAFTTSVRSYLPNTVTDALRGSGAWGLLLRRVGDDVLV

YLLAHCALYLLVPPSCAYQVCGSPLYQICATTDIWPSVSASYRPTRPVGRNFTNLRFLQQIKSSSRQEAPKPLAL
HLLARCALFVLVAPSCAYQVCGPPLYQLGAATQARPPHAS.GPRRRLG        CERAWNHSVREAGVPLGL

PSRGTKRHLSLTSTSVPSAKKARCYPVPRVEEGPHRQVLPTPSGKSWVPSPARSPEVP...TAEKDLSSKGKVSD
PAPGARRGGSASRSLPLPKRPRRGAAPEPERTPVGQGSWAHPGRTRGPSDRGFCVVSPARPAEEATSLEGALSG

LSLS.GSVCCKHKPSSTSLLSPPRQNAFQLRP.FIETRHFLYSRGDGQERLNPSFLLSNLQPN  LTGARRLVEIIF
TRHSHPSVGRQHHAGPPSTSRPPRPWDTPCPPVYAETKHFLYSSGD.KEQLRPSFLLSSLRPSLTGARRLVETIF

LGSRPRTSGPLCRTHRLSRRYWQMRPLFQQLLVNHAECQYVRLLRSHCRFRTA...........    NQQVTDA
LGSRPWMPGTPRRLPRLPQRYWQMRPLFLELLGNHAQCPYGVLLKTHCPLRAAVTPAAGVCAREKPQGSVAAPEE

FIGURE 3
page 2 of 3 mTRT vs. hTRT amino acid alignment

LNTSPPHLMDLLRLHSSPWQVYGFLRACLCKVVSASLWGTRHNERRFFKNLKKFISLGKYGKLSLQELMWKMKVE
EDTDPRRLVQLLRQHSSPWQVYGFVRACLRRLVPPGLWGSRHNERRFLRNTKKFISLGKHAKLSLQELTWKMSVR

Motif T

DCHWLRSSPGKDRVPAAEHRLRERILATFLFWLMDTYVVQLLRSFFYITESTFQKNRLFFYRKSVWSKLQSIGVR
DCAWLRRSPGVGCVPAAEHRLREEILAKFLHWLMSVYVVELLRSFFYVTETTFQKNRLFFYRKSVWSKLQSIGIR

Motif 1    Motif 2

QHLERVRLRELSQEEVRHHQDTWLAMPICRLRFIPKPNGLRPIVNMSYSMGTRALGRRKQAOHFTQRLKTLFSML
QHLKRVQLRELSEAEVRQHREARPALLTSRLRFIPKPDGLRPIVNMDYVVGARTFREKRAERLTSRVKALFSVL

Motif A

NYERTKHPHLMGSSVLGMNDIYRTWRAFVLRVRALDQTPRMYFVKADVTGAYDAIPQGKLVEVVANMIRHSESTY
NYERARRPGLLGASVLGLDDIHRAWRTFVLRVRAQDPPPELYFVKVDVTGAYDTIPQDRLTEVIASIIK.PQNTY

CIRQYAVVRRDSQGQVHKSFRRQVTTLSDLQPYMGQFLKHLQDSDASALRNSVVIEQSISMNESSSLFDFFLHF
CVRRYAVVQKAAHGHVRKAFKSHVSTLTDLQPYMRQFVAHLQET..SPLRDAVVIEQSSSLNEASSGLFDVFLRF

Motif B'                Motif C    Motif D

LRHSVVKIGDRCYTQCCGIPQGSSLSTLLCSLCFGDMENKLFAEVQRDGLLLRFVDDFLLVTPHLDQAKTFLSTL
MCHHAVRIRGKSYVQCQGIPQGSILSTLLCSLCYGDMENKLFAGIRRDGLLLRLVDDFLLVTPHLTHAKTFLRTL

FIGURE 3
page 3 of 3 mTRT vs. hTRT amino acid alignment

Motif D              Motif E
VHGVPEYGCMINLQKTVVNFPVEPGTLGGAAPYQLPAHCLFPWCGLLLDTQTLEVFCDYSGYAQTSIKTSLTFQS
VRGVPEYGCVVNLRKTVVNFPVEDEALGGTAFVQMPAHGLFPWCGLLLDTRTLEVQSDYSSYARTSIRASLTFNR VFKAGKTMRNKLLSVLRLKCHGLFLDLQVNSLQTVCINYKIFLLQAYRFHACVIQLPFDQRVRKNLTFFLGIIS
GFKAGRNMRRKLFGVLRLKCHSLFLDLQVNSLQTVCTNYKILLLQAYRFHACVLQLPFHQQVWKNPTFFLRVIS SQASCCYAILKVKNPGMTLKASGS...FPPEAAHWLCYQAFLLKLAAHSVIYKCLLGPLRTAQKLLCRKLPEATM
DTASLCYSILKAKNAGMSLGAKGAAGPLPSEAVQWLCHQAFLLKLTRHRVTYVPLLGSLRTAQTQLSRKLPGTTL

TILKAAADPALSTDFQTILD 1122
TALEAAANPALPSDFKTILD 1132

FIGURE 4
page 1 of 2

Motif T

```
TRT con      WL      V   LL FFY   TE     R  YY RK  W   L    I
hTRT/hEST2p  WLMSVYVVELLRSFFYVTETTFQKNRLFFYRKSVWSKLQSIGIRQHLK
mTRT         WLMDTYVVQLLRSFFYITESTFQKNRLFFYRKSVWSKLQSIGVRQHLE
Ea_p123      WIFEDLVVSLIRCFFYVTEQQKSYSKTYYYRKNIWDVIMKMSIADLKK
Sc_EST2p     WLFRQLIPKIIQTFFYCTEISSTVT-     IVYFRHDTWNKLITPFIVEYFK
Sp_Trt1p     WLYNSFIIPILQSFFYITESSDLRNRTVYFRKDIWKLLCRPFITSMKM
```

Motif 1                                             Motif 2

```
TRT con               LR  IPK         R I            K
hTRT/hEST2p   EVRQHREARPALLTSRLRFIPKPDG    LRPIVNMDYVVGARTFRREKRAERLTSRV
mTRT          EVRHHQDTWLAMPICRLRFIPKPNG    LRPIVNMSYSMGTRALGRRKQAQHFTQRL
Ea_p123       KEVEEWKKSLGFAPGKLRLIPKKTT    FRPIMTFNKKIVNSDRKTTKLTTNTKLLN
Sc_EST2p      CRNHNSYTLSNFNHSKMRIIPKKSNN   FRIIAIPCRGADEEFTIYKENHKNAIQP
Sp_Trt1p      NNVRMDTQKTTLPPAVIRLLPKKNT    FRLITNLRKRFLIKMGSNKKMLVSTNQTL
```

Motif A

```
              P   YF K  DV    YD I
hTRT/hEST2p   PPPELYFVKVDVTGAYDTIPQDRLTEVIASIIKP
mTRT          QTPRMYFVKADVTGAYDAIPQGKLVEVVANMIRH
Ea_p123       GQPKLFFATMDIEKCYDSVNREKLSTFLKTTKLL
Sc_EST2p      VLPELYFMKFDVKSCYDSIPRMECMRILKDALKN
Sp_Trt1p      FGRKKYFVRIDIKSCYDRIKQDLMFRIVKKKLKD
```

FIGURE 4
page 2 of 2

Motif B'

```
              K Y  Q    GIPQ GS LS   L       Y    D
TRT con
htrt/hEST2p   KSYVQCQGIPQGSILSTLLCSLCYGDMENKLFAGI
mTRT          RCYTQCCQGIPQGSSLSTLLCSLCFGDMENKLFAEV
Ea_p123       KFYKQTKGIPQGLCVSSILSSFYYATLEESSLGFL
Sc_EST2p      KCYIREDGLFQGSSLSAPIVDLVYDDLLEFYSEFK
Sp_Trt1p      SQYLQKVGIPQGSILSSFLCHFYMEDLIDEYLSFT
```

Motif C

```
              LLR    DDFLL IT
TRT con
htrt/hEST2p   LLRLVDDFLLVTPHLTH
mTRT          LLRFVDDFLLVTPHLDQ
Ea_p123       LMRLTDDYLLITTQENN
Sc_EST2p      ILKLADDFLIISTDQQQ
Sp_Trt1p      LLRVVDDFLFITVNKKD
```

Motif D

```
              A    F  G                N  K
TRT con
htrt/hEST2p   AKTFLRTLVRGVPEYGCVVNLRKTVV
mTRT          AKTFLSTLVHGVPEYGCMINLQKTVV
Ea_p123       AVLFIEKLINVSRENGFKFNMKKLQT
Sc_EST2p      VINIKKLAMGGFQKYNAKANRDKILA
Sp_Trt1p      AKKFLNLSLRGFEKHNFSTSLEKTVI
```

Motif E

```
                    W  G
TRT con
htrt/hEST2p   HGLFPWCGLLL
mTRT          HCLFPWCGLLL
Ea_p123       QDYCDWIGISI
Sc_EST2p      KELEVWKHSST
Sp_Trt1p      KKRMPFFGFSV
```

FIGURE 5
General and Murine Specific TERT Amino Acid Motifs $x_n$ - any aa
h = A, L, I, V, P, F, W, M
p = G, S, T, Y, C, M, Q
c = D, E, H, K, R

| | | | | |
|---|---|---|---|---|
| $r_1$ = I, L | $r_5$ = F > L | $r_9$ = R > K | $r_{13}$ = G > H | $r_{17}$ = T > S |
| $r_2$ = R, Q | $r_6$ = P > F | $r_{10}$ = G > V | $r_{14}$ = C > A | |
| $r_3$ = Y > F | $r_7$ = S > L | $r_{11}$ = N > S | $r_{15}$ = I > V | |
| $r_4$ = K > H | $r_8$ = L > M | $r_{12}$ = W > F | $r_{16}$ = L > V | |

" > " = 1st aa preferred over the 2nd
gen = general TERT motif
hum = human specific motif
mus = mouse specific motif
bold residues are species specific changes

Motif T
gen    W-$r_1$-$x_4$-h-h-x-h-h-$r_2$-p-F-F-Y-x-T-E-x-p-$x_3$-p-$x_{2-3}$-$r_3$-$r_3$-R-$r_4$-$x_2$-W
hum   W-$r_1$-$x_4$-h-h-x-h-h-$r_2$-p-F-F-Y-V-T-E-x-p-$x_3$-p-$x_{2-3}$-$r_3$-$r_3$-R-$r_4$-$x_2$-W
mus   W-$r_1$-$x_4$-h-h-x-h-h-$r_2$-p-F-F-Y-I-T-E-x-p-$x_3$-p-$x_{2-3}$-$r_3$-$r_3$-R-$r_4$-$x_2$-W

Motif 1
gen    h-R-h-$r_1$-P-K-$x_2$-p
hum   h-R-h-$r_1$-P-K-x-D-p
mus   h-R-h-$r_1$-P-K-x-N-p

Motif 2
gen    $r_5$-R-h-I-$x_2$-h
hum   "
mus   "

Motif A
gen    P-c-x-$r_3$-F-h-x-h-D-h-$x_2$-$r_{14}$-Y-D-x-$r_{15}$
hum   P-E-x-$r_3$-F-h-x-V-D-h-$x_2$-$r_{14}$-Y-D-x-$r_{15}$
mus   P-R-x-$r_3$-F-h-x-D-D-h-$x_2$-$r_{14}$-Y-D-x-$r_{15}$

Motif B'
gen    Y-x-$r_2$-$x_2$-G-$r_1$-$r_6$-Q-G-$r_7$-x-$r_{16}$-S-x-h-$r_1$
hum   Y-x-$r_2$-$x_2$-G-$r_1$-$r_6$-Q-G-$r_7$-I-$r_{16}$-S-x-h-$r_1$
mus   Y-x-$r_2$-$x_2$-G-$r_1$-$r_6$-Q-G-$r_7$-S-$r_{16}$-S-x-h-$r_1$

Motif C
gen    $r_1$-$r_8$-$r_9$-h-x-D-D-$r_3$-L-h-$R_{15}$-$R_{17}$
hum   $r_1$-$r_8$-$r_9$-L-x-D-D-$r_3$-L-h-$R_{15}$-$R_{17}$
mus   $r_1$-$r_8$-$r_9$-F-x-D-D-$r_3$-L-h-$R_{15}$-$R_{17}$

Motif D
gen    $r_{10}$-$x_2$-c-x-p-$x_3$-$r_{11}$-$x_2$-K-$x_3$
hum   $r_{10}$-$x_2$-c-x-p-$x_3$-$r_{11}$-R-K-$x_3$
mus   $r_{10}$-$x_2$-c-x-p-$x_3$-$r_{11}$-Q-K-$x_3$

Motif E
gen    $r_{12}$-x-$r_{13}$-x-$r_7$-x
hum   "
hum   "

FIGURE 6
page 1 of 2 mTRT Promoter Region
-cDNA start at 1680
-ORF start at 1709

```
AAAGCAGGCC  TGTAACACAA  AGGTCCTTTT  TCCTGTTTA   TCGTGGCTGG    50
TAGACAATTT  CCACTTGTTT  TCCACTTCAG  TTTTTCTAC   TCGGTTGTTA   100
TTGGATTCTG  ATGCTTGAAC  CCAGGTTGGT  AGTCAGCAAG  TGCACCCCTT   150
CCTTCTTTTT  CTTGGTTTTT  TGAGGCAGG   TCTCATTTTG  CCCAAGTGGA   200
CCTAAATTTC  AGCATGTAGT  GGCTGGTTTN  GAATGCTTTT  TCATCCTGCT   250
NTACTTCCCA  AGAGTAGCTA  ACAAGTGTGC  ACCACCATGC  CCCGCGATAT   300
TTTTATTTTT  GAGACTGTTT  TCTATGCTGG  TTTCTTTGGG  GAACTACACT   350
AAGGTAGCTT  ACAAGTGTGC  ACCACCATGC  CCCGCGATAT  TCTTATTTTT   400
GAGACTGTTT  TCTATGCTGG  TTTCTTTGGG  GAACTACACT  AAGGTAGCTT   450
CATTGTTGGC  ATAAATTTCT  CAGTTCAGGC  CCATATCTCT  TAAGTAGCAG   500
AACTAAGCCA  AATCTTCAAA  CAAACCCCTT  CAAAAAGACT  GATGTCCACT   550
AAACGGACTT  CTAAAATAGC  TCCCTGTAAT  CCTGAGCATT  TACCAAGGCG   600
GCAGACTTCC  TATAAGGGAG  TAAATATGAA  AACGCGCCTG  TTCAAATGCT   650
AGGTCGGTGG  ATAGAAGCAA  TTTCCTCAGA  AAGCTGAAGG  CACCAAAGGT   700
TATATTTGTT  AGCATTTCAG  TGTTTGCCAA  ACTCAGCTAC  AGTAGAGATC   750
ACAGATTCCC  TATTTCCCAG  AGATTCAAAA  TTCAGCAGCC  CCTCTCTAAC   800
TATGGCTCAG  AGTCGTGTCA  TTACATATGC  CCCAACAACA  ACCCCACCC   850
CTATCCTACC  CCCGCCTCAC  ACGTGCAAGT  ACTATCACAG  TTGCCAACCT   900
AGCAGAGCTG  CCATCCTAAG  GTCGAGGTCG  CCGCTTTGGC  TGTGTGCACA   950
GGCAAGCGCC  CTCACCCAAT  GGCCCCTGGCC  TTGCTATGGG  TGCGTGAGTT  1000
GAGATGATGC  TCTGGACTCT  GAGGTGAAGG  CCACTGGAAC  AGTGAAAAAA  1050
GCTAACGCAG  GGCTTTTACC  TAGGTCCCCT  TCCTTTGGTG  GTGGGTGTTT  1100
ACGGAACATA  TTTGGGATCT  GGAGTGTATG  GTCGCACCAC  AATAAAGCCT  1150
```

FIGURE 6
page 2 of 2

| | | | | |
|---|---|---|---|---|
| TAACCTATAT | AGTAGAATGT | TCAGCTGTAA | TCATTAAGAA | CTGAGATTGC | 1200
| CACCACCCAC | CTCACTGTCT | GTGTCAACCA | CAGCAGGCTG | GAGCAGTCAG | 1250
| CTCAGGAACA | GGCAAAACCT | TAGGTCCTCC | GCCTACCTAA | CCTTCAATAC | 1300
| ATCAAGGATA | GGCTTCTTTG | CTTGCCCAAA | CCTCGCCCCA | GTCTAGACCA | 1350
| CCTGGGGATT | CCCAGCTCAG | GGCGAAAAGG | AAGCCCGAGA | AGCATTCTGT | 1400
| AGAGGAAAAT | CCTGCATGAG | TGCGCCCCCT | TTCGTTACTC | CAACACATCC | 1450
| AGCAACCACT | GAACTTGGCC | GGGGAACACA | CCTGGTCCTC | ATGCACCAGC | 1500
| ATTGTGACCA | TCAACGGAAA | AGTACTATTG | CTGCGACCCC | GCCCCTTCCG | 1550
| CTACAACGCT | TGGTCCGCCT | GAATCCCGCC | CCTTCCTCCG | TTCCAGCCT | 1600
| CATCTTTTC | GTCGTGGACT | CTCAGTGGCC | TGGGTCCTGG | CTGTTTTCTA | 1650
| AGCACACCCT | TGCATCTTGG | TTCCCGCACG | TGGGAGGCCC | ATCCCGGCCT | 1700
| TGAGCACAAT | GACCCGGCGT | CCTCGTTGCC | CCGCGGGTGCG | CTCTCTGCTG | 1750
| CGCAGCCGAT | ACCGGGAGGT | GTGGCCCGCTG | GCAAACCTTTG | TGCGGCGCCT | 1800
| GGGGCCCG | | | | | 1808 mTERT Genomic DNA

FIGURE 8
page 1 of 2

Preliminary sequence of B2.18, containing the promoter region of mTERT.
cDNA starts at: 2057
ORF starts at: 2087

```
AAACAAAGTC AATGAGGAAT GGCTGTGTTC CATCTTGACC ACTGAGAAGT      50
AAAACCGGGT GCAGTGATGT CCAAAAAGGC AAGTGACAG CAGAGCGGAG      100
GCCCCAATCT AGAGCAGGGC CTTCGGTTTG AATGGGGGAG ATCAAACGGG     150
AGTTGGTTTC TGCCAGCACG TTGGGGTAGA AGGTGGAACA TGAAAGGTCC    200
CCGAGGATTT CGAGAGTCCA TAGGGGTAGC GACACCCGAG GTCTTCTTTT    250
TCACCTCCTT CCCTGCAGGG GAGATGACTT TTACCACAGT CGTTTATGGG    300
AAAGTTCCTA GGGGCAGCCC CTCCCCAAAA AGGCTCTCCC TGGCCTCATG    350
TTTCAAAGCA CAGCTTTTTA AAGCAGGCCT GTTAAGCACA AAGGATCCCG    400
AATCCTGGCT TCATCGTTGG CTGGTAGACA ACTTCCACTC GTTTTCCACT    450
TCAGTTTCTT CTAACTCTGT TGTTATTTGA TTCTGATGCT TGAACCCAGG    500
GTTGTGTAGT CAGCAAGTGC TACCCCCTCC TCCTCTTCTT TGTTTTTTTG    550
AGGCAGGGTC TCATTTTGCC CAAGTGGACC TAAATTTCAG CATGTAGCTG    600
GCCTGGTTTT GAATGCCTTC TCATCCTGCC TCTACTTCCC AAGAGTAGCT    650
TACAAGTGTG CACCACCATG CCCCGCGATA TTCTTATTTT TGAGACTGTT    700
TTCTATGCTG GTTTCTTTGG GGAACTACAC TAAGGTAGCT TACAAGTGTG    750
CACCACCATG CCCCGCGATA TTCTTATTTT TGAGACTGTT TTCTATGCTG    800
GTTTCTTTGG GGAACTACAC TAAGGTAGCT TCATTGTTGG CATAAATTTC    850
TCAGTTCAGG CCCATATCTC CTAAGTAGCA GAACTAAGCA AATCTCAAAC    900
AAACCCCTCA AAAAGACTGA TGTCCACTAA ACGGACTTCT AAAATAGCTC    950
CCTGTAATCC TGAGCATTTA CAAGGGGCA GACCTCCTAT AAGGGAGTAA    1000
ATATGAAAAC GCGCCTGTTC AAATGCTAGG TCGGTGGATA GAAGCAATTT    1050
CCTCAGAAAG CTGAAGGCAC CAAAGGTTAT ATTTGTTAGC ATTTCAGTGT    1100
TTGCCAAACT CAGCTACAGT AGAGATCACA GATTCCCTAT TTCCCAGAGA    1150
TTCAAAATTC AGCAGCCCCT CTCTAACTAT GGCTCAGAGT CGTGTCATTA    1200
CATATGCCCC AACAACAACC CCCACCCCTA TCCTACCCCC GCCTCACACG    1250
TGCAAGTACT ATCACAGTTG CCAACCTAGC AGAGCTGCCA TCCTAAGGTC    1300
GAGGTCGCCG CTTTGGCTGT GTGCACAGGC AAGCGCCCTC ACCAATGGC    1350
CCTGGCCCTG CTATGGGTGC GTGAGTTGAG ATGATGCTCT GGACTCTGAG    1400
```

FIGURE 8
page 2 of 2

```
GTGAAGGCCA CTGGAACAGT GAAAAAAGCT AACGCAGGGC TTTTACCTAG 1450
GTCCCCTTCC TTTGGTGGTG GGTGTTTACG GAACATATTT GGGATCTGGA 1500
GTGTATGGTC GCACCACAAT AAAGCCTTAA CCTATATAGT AGAATTTCAG 1550
CTGTAATCAT TAAGAACTGA GATTGCCACC ACCCACCTCA CTGTCTGTGT 1600
CAACCACAGC AGGCTGGAGC AGTCAGTTCA GGAACAGGCA AAACCTTAGG 1650
TCCCTCCGCC TACCTAACCT TCAATACATC AAGGATAGGC TTCTTTGCTT 1700
GCCCAAACCT CGCCCCAGTC TAGACCACCT GGGGATTCCC AGCTCAGGGC 1750
GAAAGGAAG CCCGAGAAGC ATTCTGTAGA GGGAAATCCT GCATGAGTGC 1800
GCCCCTTTC GTTACTCCAA CACATCCAGC AACCACTGAA CTTGGCCGGG 1850
GAACACACCT GGTCCTCATG CACCAGCATT GTGACCATCA ACGGAAAAGT 1900
ACTATTGCTG CGACCCCGCC CCTTCCGCTA CAACGCTTGG TCCGCCTGAA 1950
TCCCGCCCCT TCCTCCGTTC CCAGCTCAT CTTTTTCGTC GTGGACTCTC 2000
AGTGGCCTGG GTCCTGGCTG TTTTCTAAGC ACACCCTTGC ATCTTGGTTC 2050
CCGCACGTGG GAAGGCCCAT CCCGGCCTTG AGCACAAATGA CCCGCGCTCC 2100
TCGTTGCCCC GCGGTGCGCT CTCTGCTGCG CAGCCGATAC CGGGAGGTGT 2150
GGCCGCTGGC AACCTTTGTG CGGCGCCTGG GGCCCGAGGG CAGGCGGCTT 2200
GTGCAACCCG GGGACCGAAG ATCTACCGCA CTTTGGGTTG CCCAATGCCT 2250
AGTGTGCATG CACTGGGGCT CACAGCCTCC ACCTGCCGAC CTTTCCTTCC 2300
ACCAGGTGGG CCTCCAGGCG GGATCCCCAT GGGTCAGGGG CGGAAAGCCG 2350
GGAGGACGTG GGATAGTGCG TCTAGCTCAT GTGTCAAGAC CCTCTTCTCC 2400
TTACCAGGTG TCATCCCTGA AAAGAGCTGG TGGCCAGGGT TGTGCAGAGA 2450
CTCTGCGAGC GCAACGAGAG AAACGTGCTG GCTTTTGGCT TTGAGCTGCT 2500
TAACGAAGCC AGAAGCGGGC CTCCACACTG TTATTGAAAA CCTGCGTGTC TAGCGTGCGT 2550
AAGCTACTTG CCCAACACTG TTATTGAAAA CCTGCGTGTC AGTGGTGCAT 2600
GGATGCTACT GTTGAGCCCGA ATGGGGCGACA CCTGCTGGTC TACCTGCTGG 2650
C                                                      2651
``` mTERT Genomic DNA

MOUSE TELOMERASE REVERSE TRANSCRIPTASE

This application is a continuation-in-part of and claims the priority benefit of U.S. patent application Ser. No. 08/979,742, filed Nov. 26, 1997, now abandoned.

Incorporated herein by reference in their entirety and for all purposes are the following: U.S. patent application Ser. Nos. 08/979,742; 08/974,549; and 08/974,584; PCT Applications PCT/US97/17618 and PCT/US97/17885; and U.S. patent application Ser. Nos. 08/915,503, 08/912,951, 08/911,312, 08/854,050, 08/851,843, 08/846,017, 08/844,419, and 08/724,643.

This invention was made with United States Government support under Grant No. HD/CA 34880, awarded by the National Institutes of Health. The United States Government has certain rights in the invention.

FIELD OF THE INVENTION

The subject matter of this application provides novel recombinant telomerase enzyme genes and proteins and relates to the cloning and characterization of the catalytic protein component of mouse telomerase enzyme, referred to as mouse telomerase reverse transcriptase ("mTERT").

This invention pertains generally to cell proliferation and aging, including the fields of age-related diseases, such as cancer and cell biology. In particular, this invention pertains to the discovery of a novel mTERT enzyme proteins and nucleic acids, and methods for isolating and expressing by recombinant means these nucleic acids and proteins. The invention provides antibodies specifically reactive with mTERT. The invention also pertains to methods of screening for novel mTERT activity modulators. The invention also includes means of mortalizing cells, creating indefinitely proliferating cells and immortalizing cells, including normal, diploid cells, using the novel reagents, proteins, nucleic acids, enzymes and methods of the invention.

BACKGROUND OF THE INVENTION

The following discussion is intended to provide general information regarding the field of the present invention. The citation of various references is not to be construed as an admission of prior invention.

Telomeres, the protein-DNA structures physically located on the ends of chromosomes in eukaryotic organisms, are required for chromosome stability and are involved in chromosomal organization within the nucleus (Zakian (1995) *Science* 270:1601, Blackburn (1978) *J. Mol. Biol.*, 120:33, Oka (1980) *Gene* 10:301, Klobutcher (1981) *Proc. Natl. Acad. Sci. USA* 78:3015). Telomeres are believed to be essential in most eukaryotes, as they allow cells to distinguish intact from broken chromosomes, protect chromosomes from degradation, and act as substrates for replication. Telomere loss, i.e., inability to maintain telomere structure, is associated with normal human cellular development, including cell aging and cellular senescence. Telomere gain, i.e., the ability to maintain telomere structure in cells, is associated with chromosomal changes and cancer.

Telomeres are generally replicated in a complex, cell cycle and developmentally regulated manner by a "ribonucleoprotein telomerase enzyme complex." The telomerase reverse transcriptase enzyme is a telomere-specific RNA-dependent DNA polymerase comprising a telomerase reverse transcriptase (TERT) protein and an RNA component. Telomerase enzyme uses its RNA component to specify the addition of telomeric DNA repeat sequences to chromosomal ends (U.S. Pat. No. 5,583,016; Villeponteau (1996) *Cell and Develop. Biol.* 7:15–21). In addition to the template RNA component, other proteins have been found to be associated with TRT. For example, telomerase-associated proteins called p80 and p95 were found in *Tetrahymena* (Collins (1995) *Cell* 81:677). Homologs of the p80 protein have been found in humans, rats and mice. Neither enzymatic activity nor amino acid motifs typically associated with RNA-dependent DNA polymerases have been found to be associated with these proteins (Harrington (1997) *Science* 275:973–977). In contrast, mutational analysis and reconstitution in vitro have shown the TERT proteins contain the catalytic moieties of telomerase (Lingner (1997) *Science* 276:561–567; Weinrich (1997) *Nature Genetics* 17:498–502). Various structural proteins that interact with telomeric DNA that are distinct from the protein components of TRT have also been described. In mammals, most of the simple repeated telomeric DNA is packaged in closely spaced nucleosomes (Makarov (1993) *Cell* 73:775, Tommerup (1994) *Mol. Cell. Biol.* 14:5777). However, the telomeric repeats located at the very ends of the human chromosomes appear to be in a non-nucleosomal structure that has been termed the telosome.

Telomeric DNA can consist of a variety of different structures. Typically, telomeres are tandem arrays of very simple sequences, such as simple repetitive sequences rich in G residues, in the strand that runs 5' to 3' toward the chromosomal end. In humans, the telomere repeat sequence is 5'-TTAGGG-3' (SEQ ID NO:7). In contrast, telomeric DNA in Tetrahymena is comprised of repeats of the sequence $T_2G_4$, while in Oxytricha, the repeat sequence is $T_4G_4$ (Zakian (1995) *Science* 270:1601; Lingner (1994) *Genes Develop.* 8:1984). Heterogenous telomeric sequences have been reported in some organisms, such as the repeat sequence $TG_{1-3}$ in Saccharomyces. The repeated telomeric sequence in other organisms is much longer, such as the 25 base pair repeat sequence of *Kluyveromyces lactis*. Furthermore, telomeric structure can be completely different in other organisms. For example, the telomeres of Drosophila are comprised of a transposable element (Biessman (1990) *Cell* 61:663, Sheen (1994) *Proc. Natl. Acad. Sci. USA* 91:12510).

In most organisms, the size of the telomere fluctuates. For example, the amount of telomeric DNA at individual yeast telomeres in a wild-type strain may range from approximately 200 to 400 bp, with this amount of DNA increasing and decreasing stochastically (Shampay (1988) *Proc. Natl. Acad. Sci. USA* 85:534). Heterogeneity and spontaneous changes in telomere length may reflect a complex balance between the processes involved in degradation and lengthening of telomeric tracts. In addition, genetic, nutritional and other factors may cause increases or decreases in telomeric length (Lustig (1986) *Proc. Natl. Acad. Sci. USA* 83:1398, Sandell (1994) *Cell* 91:12061).

Telomeres are not maintained via conventional replicative processes. Complete replication of the ends of linear eukaryotic chromosomes presents special problems for conventional methods of DNA replication. Conventional DNA polymerases cannot begin DNA synthesis de novo; rather, they require RNA primers that are later removed during replication. In the case of telomeres, removal of the RNA primer from the lagging-strand end would necessarily leave a 5'-terminal gap, resulting in the loss of sequence from the leading strand if the daughter telomere was subsequently blunt-ended (Watson, (1972) *Nature New Biol.* 239:197, Olovnikov (1973) *J. Theor. Biol.*, 41:181).

While conventional DNA polymerases cannot accurately reproduce chromosomal DNA ends, specialized factors exist to ensure their complete replication. The telomerase enzyme is a key component in this process. In vivo, telomerase enzyme is assembled as a ribonucleoprotein (RNP) enzyme complex. It is an RNA-dependent DNA polymerase that uses a portion of its internal RNA moiety as a template for telomere repeat DNA synthesis (Yu (1990) Nature 344:126; Singer (1994) Science 266:404; Autexier (1994) Genes Develop. 8:563; Gilley (1995) Genes Develop. 9:2214; McEachern (1995) Nature 367:403; Blackburn (1992) Ann. Rev. Biochem. 61:113; Greider (1996) Ann. Rev. Became. 65:337). A combination of factors, including telomerase processivity, frequency of action at individual telomeres, and the rate of degradation of telomeric DNA, contribute to the size of the telomeres (i.e., whether they are lengthened, shortened, or maintained at a certain size). In vitro, telomerases may be extremely processive; for example, Tetrahymena telomerase can add an average of approximately 500 bases to the G strand primer before dissociation of the enzyme (Greider (1991) Mol. Cell. Biol., 11:4572).

Telomere replication is regulated both by developmental and cell cycle factors. Telomere replication may play a signaling role in the cell cycle. For example, certain DNA structures or DNA-protein complex formations may act as a checkpoint to indicate that chromosomal replication has been completed (Wellinger (1993) Mol. Cell. Biol. 13:4057). Telomere length is also believed to serve as a mitotic clock, which serves to limit the replication potential of cells in vivo and in vitro.

In humans, telomerase activity is not detectable in most somatic tissues. Cell that express either no or only low amounts of telomerase, such as somatic cells, undergo progressive telomere shortening with increasing age (Harley (1990) Nature 345:458, Harley (1994) Cold Spring Harbor Symp. Quant. Biol. 59:307). Some non-transformed, non-immortal cells have detectable telomerase activity. Germline cells express telomerase as required to maintain telomeric structure of chromosomes passed from generation to generation (Greider, (1996) Annu. Rev. Became. 65:337). Low levels of telomerase activity have been detected in activated human B and T lymphocytes and hematopoietic progenitor cells (Keiko (1995) J. Immunol. 155:3711; Igarshi (1997) Blood 89:1299–1307; Igarashi (1996) Biochem. Biophys. Res. Commun. 219:649; Norrback (1996) Blood 88:222).

Immortalized cells, such as most cancer cells, express significantly higher levels of telomerase, allowing for stabilization of telomeric structure. Telomerase activity has been detected in about 85% of biopsies from more than 950 primary human tumors (Kim (1994) Science 266:2011; Hiyama (1995) Nature Med. 1:249–257; Counter (1992) EMBO J. 11:192). Telomerase activity has been detected in many cancers (Wellinger (1993) supra; Autexier (1996) Trends Biochem. Sci. 21:387). However, even in telomerase-positive cells, such as most cancer cells, the levels of telomerase are very low relative to housekeeping and structural proteins.

Because telomerase is expressed (albeit in low levels) in most human cancer cells and is negligibly expressed in other cell types, it is the only true pan-cancer cell marker identified to date. Thus, there exists a great need for inhibitors of telomerase activity, which would be ideal therapeutic compositions in the treatment of cancer or uncontrolled cell growth. Furthermore, loss of or inhibition of telomerase activity is associated with cellular senescence and may lead to cell death. Therefore, there exists a great need for methods and compositions capable of promoting or reconstituting telomerase activity which would be useful in treating age-related disease and anti-aging pharmaceuticals. The present invention fulfills these and other needs.

SUMMARY OF THE INVENTION

This invention has for the first time provided the identification, cloning and characterization of mouse telomerase reverse transcriptase (mTERT) proteins and nucleic acids. Mouse telomerase enzymes, including associated nucleic acids and other polypeptides, are further provided. Also, the invention provides novel reagents and methods complementing this significant achievement.

The invention provides for an isolated or recombinant nucleic acid encoding an mTERT, the protein defined as having a calculated molecular weight of between 50 and 150 kDa, and specifically binding to an antibody raised against the protein of SEQ ID NO:2, or a subsequence thereof, or having at least 60% amino acid sequence identity to an mTERT protein comprising SEQ ID NO:2. In one embodiment, the calculated molecular weight of the encoded mTERT protein is about 127 kDa. In further embodiments, the encoded protein has at least 80% amino acid sequence identity to a protein comprising SEQ ID NO:2, or, the encoded protein comprises SEQ ID NO:2.

In alternative embodiments, the invention provides for an isolated or recombinant nucleic acid which specifically hybridizes to SEQ ID NO:1 under stringent conditions, an isolated nucleic acid encoding a protein which specifically binds to an antibody directed against a protein comprising SEQ ID NO:2, and an isolated nucleic acid comprising either 10 to 15 or more nucleotides identical or exactly complementary to SEQ ID NO:1 or a nucleotide sequence encoding at least about five contiguous amino acids of an mTERT, wherein the TERT has an amino acid sequence as set forth in SEQ ID NO:2 or conservative substitutions of said amino acid sequence. In another embodiment, the invention provides an isolated nucleic acid encoding a fusion protein comprising an mTERT. The invention also provides a nucleic acid free of dideoxynucleotides, as well as nucleic acids comprising non-naturally occurring nucleotides. One embodiment provides for an isolated nucleic acid comprising a label and a nucleotide sequence of the invention.

The invention also provides for an isolated or recombinant peptide encoded by a recombinant or isolated nucleotide sequence encoding at least about five contiguous amino acids of an mTERT.

In another embodiment, the invention provides for an isolated or recombinant mTERT protein where the mTERT has a calculated molecular weight of about 50 to 150 kDa; and specifically binds to an antibody raised against a protein comprising SEQ ID NO:2, or subsequence thereof, or has 60% amino acid sequence identity to a protein comprising SEQ ID NO:2. The isolated or recombinant mTERT protein can have a calculated molecular weight of about 127 kDa, or the protein can comprise SEQ ID NO:2. In an alternative embodiments, the isolated or recombinant mTERT protein is encoded by a nucleic acid molecule which specifically hybridizes to SEQ ID NO:1; and, the isolated or recombinant mTERT protein, or subsequence thereof, can further comprise a fusion protein.

The invention provides for an isolated or recombinant antibody specifically immunoreactive under immunologically reactive conditions to an mTERT protein; the mTERT protein can comprise the sequence as set forth in SEQ ID NO:2. The invention also provides for an isolated or recombinant antibody, specifically immunoreactive under immunologically reactive conditions, to an mTERT protein encoded by the nucleic acid of claim 1; the nucleic acid can comprise the sequence as set forth in SEQ ID NO:1. The invention further provides for an isolated or recombinant mTERT protein which specifically binds to the anti-mTERT antibodies of the invention.

Alternative embodiments provide for a transfected cell comprising a heterologous gene encoding a mTERT protein or subsequence thereof; a transfected cell into which an exogenous nucleic acid sequence has been introduced, where the nucleic acid specifically hybridizes under stringent conditions to SEQ ID NO:1 or a nucleic acid of the invention as described herein, and the cell expresses the exogenous nucleic acid as an mTERT protein; and a transfected cell where the transfected cell is a karotypically normal diploid cell.

The invention also provides for an organism into which an exogenous nucleic acid sequence has been introduced, the nucleic acid specifically hybridizing under stringent conditions to a nucleic acid with a sequence as set forth in SEQ ID NO:1, or a nucleic acid of the invention as described herein, and the organism expresses the exogenous nucleic acid as a mouse TERT protein. The organism can express an exogenous nucleic acid comprising a nucleic acid of the invention. Alternatively, the organism expresses and translates an exogenous nucleic acid sequence into a mouse TERT protein, which can be expressed externally from the organism. The organism can be an insect, as a Spodoptera sp., Trichoplusia sp. or a Lymantria sp. The insect can specifically be a *Spodoptera frugiperda, Trichoplusia ni* or a *Lymantria dispar*. The organism can be a plant, a fungus or a yeast. If it is a yeast, the organism can be a Pichia sp., Hansenula sp., Torulopsis sp., Saccharomyces sp., or a Candida sp. The yeast can specifically be a *Pichia pastoris, Hansenula polymorpha, Torulopsis holmil, Saccharomyces fragilis, Saccharomyces cerevisiae, Saccharomyces lactis,* or a *Candida pseudotropicalis*. The organism can be a bacterium, such as *Escherichia coli, Streptococcus cremoris, Streptococcus lactis, Streptococcus thermophilus, Leuconostoc citrovorum, Leuconostoc mesenteroides, Lactobacillus acidophilus, Lactobacillus lactis, Bifidobacterium bifidum, Bifidobacteriu breve,* or a *Bifidobacterium longum*.

The invention also provides for an expression vector comprising a nucleic acid sequence which specifically hybridizes under stringent conditions to an mTERT encoding nucleic acid; the nucleic acid can have a sequence as set forth in SEQ ID NO:1.

The invention also provides for a transfected cell comprising a recombinant mTERT, wherein said cell is comprised in a transgenic non-human animal. The invention also provides for a transgenic animal which lacks a functional mTERT due to its being "knocked out" using recombinant methods and reagents of the invention. Such mTERT knockouts mice are especially useful in studying the effect of telomerase and in testing anti-cancer telomerase inhibitors, i.e., in mice comprising human tumor xenografts.

In one embodiment, the invention provides for a transgenic cell or non-human animal, and progeny thereof, wherein said animal comprises an endogenous mTERT gene which has been mutated by recombinant means with a nucleic acid comprising a subsequence of a nucleic acid encoding an mTERT or complementary to an mTERT. The transgenic cell or non-human animal can be deficient in at least one mTERT or telomerase enzyme activity, or completely lack all mTERT or telomerase enzyme activity. The transgenic cell or non-human animal can comprise an mTERT with a deficiency in activity which is a result of a mutated gene encoding an mTERT having a reduced level of a telomerase enzyme activity compared to a wild-type telomerase enzyme activity. The transgenic cell or non-human animal can contain a mutated mTERT gene comprising one or more mutations selected from the group consisting of a missense mutation, a substitution, a nonsense mutation, an insertion, or a deletion. The transgenic cell or non-human animal can be a mouse, i.e., of the family Muridae. In particular, *M. spretus* or *M. musculus* spp. are provided. The transgenic non-human animal can further comprise a human telomerase reverse transcriptase.

The invention further provides for a kit for the detection of a mouse TERT gene or polypeptide, the kit comprising a container containing a molecule which can be a TERT nucleic acid or subsequence thereof, a TERT polypeptide or subsequence thereof, or an anti-TERT antibody.

The invention also provides a method of determining whether a test compound is a modulator of mTERT or telomerase enzyme activity, the method comprising the steps of: providing a mouse TERT composition, contacting the TERT with the test compound and measuring the activity of the TERT, where a change in TERT activity in the presence of the test compound is an indicator of whether the test compound modulates mouse TERT or telomerase enzyme activity.

In a further embodiment, the method is carried out in a buffered aqueous solution comprising a template polynucleotide, an mTERT, a buffered aqueous solution compatible with telomerase enzyme activity, and sufficient additional nucleotide species necessary for telomerase-catalyzed polymerization of a DNA polynucleotide complementary to said template polynucleotide. This method can be carried out in a cell-free extract, an organism or a transgenic organism. In alternative embodiments of this method: the DNA is a telomere or comprises a telomeric sequence; the template polynucleotide is a mouse telomerase RNA (mTR, or mouse telomerase related component, or mTERC) or comprises an mTERC subsequence; the activity of the telomerase is measured by monitoring incorporation of a nucleotide label into DNA; the activity of the telomerase enzyme is measured by monitoring the change in rate of incorporation of nucleotides into the DNA; the activity of the telomerase enzyme can also be measured by monitoring the accumulation or loss of nucleotides into the DNA; the activity of the telomerase enzyme and mTERT can be further measured by monitoring the loss of the ability to bind to a telomerase-associated protein; the activity of the telomerase enzyme and mTERT is measured by monitoring the loss of the ability to bind to a nucleic acid; and, the activity of the mTERT is measured by monitoring the loss of the ability to bind to a chromosome.

The invention also includes a method where the test compound produces a statistically significant decrease in the activity of mTERT as compared to the relative amount of incorporated label in a parallel reaction lacking the agent, thereby determining that the agent is a telomerase enzyme or mTERT inhibitor or activator. The method can be used to determine if there is a change in telomerase enzyme or TERT activity using, e.g., a TRAP assay or using a quantitative polymerase chain reaction assay. The method can determine a change in telomerase enzyme and mTERT activity by measuring the accumulation or loss of telomere structure.

The invention provides for isolated and recombinant murine proteins and nucleic acids that include murine (mTERT) specific motifs (see FIGS. 4 and 5) and TERT specific "motifs." These motifs effect common telomerase structure and function and uniquely define members of the mTERT species of the invention. Novel reagents of the invention corresponding to these motif regions can be used in methods of the invention to generate unique murine peptides and nucleic acids, including complementary and antisense hybridization probes and primers, to identify additional mTERT, including mTERT isoforms, homologues and alleles.

Two mTERT proteins are considered to have a statistically significant sequence identity, i.e., having significant homology, at the amino acid level in a conserved region of the TERT protein, such as the motifs described above and in FIGS. 4, and 5, if, after adjusting for deletions, additions and the like, the conserved regions have about 20% to 30% sequence identity, as can be deduced or derived from FIGS. 4 or 5. However, this sequence identity can be higher, e.g., as high as about 40% to 50% or higher, if, e.g. the conserved region of comparison is shorter, i.e., a region of about 5 to about 10 consecutive amino acids. Furthermore, the skilled artisan can deduce or derive additional mTERT motifs, modifications of these mTERT motifs, and variations in the amount of sequence identity in a particular mTERT motif to determine whether a polypeptide or nucleic acid is a member of the mTERT species of the invention, and the like, by reference to the teachings and sequences of the invention, particularly including FIGS. 4 and 5.

A further understanding of the nature and advantages of the present invention may be realized by reference to the remaining portions of the specification, the figures and claims.

BRIEF DESCRIPTION OF THE FIGURES

FIG. 1 shows the complete sequencing of the mouse TERT cDNA (SEQ ID NO:1).

FIG. 2 shows the deduced mTERT translation product (SEQ ID NO:2).

FIG. 3 shows the alignment of mTERT (SEQ ID NO:2) with hTERT (SEQ ID NO:3). Positions of motifs are also indicated. Motifs 2 and D are underlined to help distinguish them from motifs 1 and C, respectively.

FIG. 4 shows mTERT motifs in relation to the sequence conservation between mTERT motifs and other TERT motifs. Motif alignments from top to bottom: human (SEQ ID NOS:21–27), mouse (SEQ ID NOS:28–39), *Euplotes aediculatus* (SEQ ID NOS:35–42), *Saccharomyces cerevisiae* (SEQ ID NOS:43–50), *Schizosaccharomyces pombe* (SEQ ID NOS:51–58). Conserved residues are indicated in bold. Consensus amino acids (TRT con)=(SEQ ID NOS:59–61).

FIG. 5 shows the murine, or Mus, specific TERT motif (specifically, Motif T, Motif 1, Motif 2, Motif A, Motif B', Motif C, Motif D, and Motif E) sequences of the invention (SEQ ID NOS:78–80, 65, and 70, respectively) in relation to other TERT amino acid motifs, (hum=human specific TRT motif=SEQ ID NOS:71–73, 65, 74–77 and 70, respectively; gen=general TRT motif=SEQ ID NOS:62–70, respectively)

FIG. 6 shows a preliminary sequence of the genomic promoter region of mTERT (SEQ ID NO:4).

FIG. 8 shows a sequence of the genomic promoter region of mTERT (SEQ ID NO:5).

DETAILED DESCRIPTION OF THE INVENTION

Figure 7:
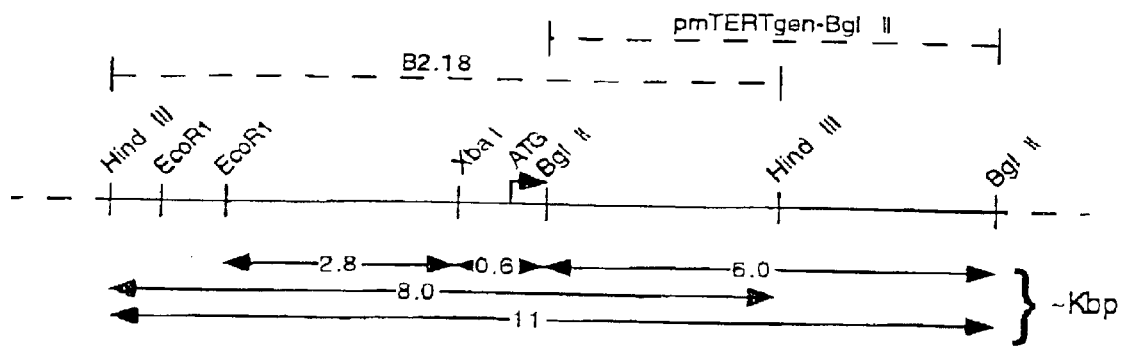
FIG. 7 shows a schematic of mTERT genomic DNA from the lambda phage genomic insert, including relevant restriction enzyme cleavage sites and fragment sizes.

This invention relates to the cloning and characterization of the mouse telomerase reverse transcriptase (mTERT) gene and provides isolated and recombinant mTERT proteins and nucleic acids. The invention further includes isolated and recombinant mouse telomerase enzymes and related methods.

The present invention provides an isolated (from synthetic or natural sources) or recombinant mTERT. In other embodiments, the invention provides for isolated and recombinant mTERT isoforms, homologues and alleles, and methods for identifying such mTERT species. In one embodiment, the mTERT is a protein of about 127 kd, having the sequence of SEQ ID NO:2, encoded by the cDNA depicted by SEQ ID NO:1.

The invention also provides for an isolated or recombinant mouse telomerase enzyme complex comprising at least one mTERT and a telomerase-associated nucleic acid moiety for use as a template for DNA synthesis. The telomerase-associated nucleic acid moiety can be derived from or based on such nucleic acids found in mice (mTERC) or humans (hTERC). In one embodiment, the telomerase enzyme complex is comprised of components of mouse origin, including mTERT encoded by the cDNA of SEQ ID NO:1, a mouse telomerase-associated RNA (mTERC) moiety. In another embodiment, the telomerase enzyme complex is comprised of components of mouse and human origin, including mTERT encoded by the cDNA of SEQ ID NO:1 and an hTERC moiety. The mouse telomerase enzyme-associated RNA component (mTERC) has been cloned and characterized, see U.S. Ser. No. 08/782,787, filed 10 Feb. 1997; U.S. Ser. No. 08/670,516, filed 27 Jun. 1996; and U.S. Ser. No. 08/485,778, filed 7 Jun. 1995. In addition, hTERC (hTR) knockout mice have been constructed, see U.S. Ser. No. 08/623,166, filed 28 Mar. 1996. hTERC has been cloned and characterized, see PCT Publication Nos. 96/01835 and 96/40868 and U.S. Pat. No. 5,583,016.

In alternative embodiments the telomerase can include any number of enzyme complex-associated proteins, such as co-purifying proteins and other proteins that regulate enzyme activity.

The present invention provides a number of different methods for expressing and isolating mTERT, telomerase enzyme and telomerase-associated compounds that can be employed, in one or more aspects, as reagents and are useful in methodologies as described herein. The novel reagents and methods of the invention provide for mice lacking in full or partial mTERT activity, i.e., mTERT "knockout" mice, and methods for making such mice.

The telomerase-associated protein can be, for example, the mouse homologue of the Tetrahymena p80 protein, described in Harrington (1997) *Science* 275:973. While some telomerase-associated proteins are known, the present invention provides methods and reagents for identifying additional telomerase enzyme-associated proteins and other compounds and assembling (i.e, "reconstituting") them with mTERT. Such telomerase enzyme-associated proteins can be prepared in accordance with, e.g., U.S. Ser. No. 08/883, 377 and PCT application No. 97/06012, both filed Apr. 4, 1997; and PCT application No. 96/14679, U.S. Ser. No. 08/710,249 and 08/713,922, all filed Sep. 13, 1996. The Tetrahymena p80 and p95 putative telomerase proteins are described in PCT publication No. 96/19580.

The invention, providing for mTERT isoforms, homologues and alleles, describes structural features common to the mTERT species of the invention in the form of structural motifs, see FIGS. 4 and 5. These motifs can effect common mTERT and telomerase enzyme functions. Sequence analysis of mTERT shows that it contains murine-specific amino acid regions, i.e., "motifs," common to other mTERT proteins, as illustrated in FIG. 5.

Novel reagents of the invention corresponding to these motif regions can be used in methods of the invention to generate antibodies and to identify additional mTERT isoforms, homologues and alleles. The invention provides oligonucleotides corresponding to these motif regions, including restriction enzyme fragments and amplification products generated from an mTERT. Oligonucleotides corresponding to motifs can also be synthesized in vitro. These oligonucleotides can also be used as PCR amplification primers or hybridization probes to identify and isolate additional mouse isoforms, homologues and alleles. These oligonucleotides can also be used as primers to amplify additional mTERT species, using techniques such as RACE, as described below.

The invention further provides for an isolated, purified or recombinant mouse telomerase enzyme complex capable of replicating telomeric DNA or any sequence determined by a telomerase enzyme-associated nucleic acid component. The telomerase enzyme complex of the invention can comprise components that are purified or isolated from a natural or synthetic source, a recombinantly manufactured.

The mTERT of the complex can be modified to delete the full or a "partial activity" of the TERT or enzyme complex, as described below.

Telomerase reverse transcriptase enzymes and mTERT are very rare in nature, and few successful attempts have been made to purify the enzyme complex; see, as examples of such successful purification, U.S. Ser. No. 08/510,736, filed Aug. 4, 1995, and U.S. Ser. No. 08/833,377, and PCT application No. 97/06012, both filed Apr. 4, 1997. The aforementioned patent applications provide useful methodologies and reagents that can be applied to the methods and reagents of the present invention. The present invention provides a variety of methods and reagents for creating the most pure mouse telomerase enzyme and mTERT preparations ever made, including methods for making recombinant telomerase enzyme and mTERT in abundant levels in recombinant host cells, methods for producing telomerase enzyme and mTERT synthetically and in cell-free translation systems. The invention provides methods for isolating recombinant or native telomerase enzyme, mTERT and telomerase components by reacting the telomerase or mTERT with an anti-telomerase antibody of the invention.

Also provided are methods and compositions for the expression of the mouse telomerase enzymes and mTERTs of the invention. In alternative embodiments, the compositions of the invention are expressed as fusion proteins comprising exogenous sequences to aid in cell targeting, purification, expression and/or detection of mTERT and telomerase enzyme. The recombinant telomerase enzyme, mTERTs and telomerase-associated compositions of the invention can be independently or co-expressed in any system, including bacteria, yeast, fungi, insect or mammalian cells or the whole organism. The telomerase enzymes and mTERTs of the invention can also be expressed ex vivo, or in vivo, e.g., as in transgenic non-human animals.

The invention also provides for methods of reconstituting telomerase enzyme and mTERT activity, including fill and partial activity, in vitro and in vivo, using the purified mTERT of the invention, with or without further incorporation of its RNA moiety or telomerase-associated components. As used herein, the term reconstitution of a telomerase activity in a cell or animal also includes inducement, augmentation or replacement of low, lost or "knocked out" telomerase enzyme or mTERT activity. In one embodiment, the method can reconstitute "full" telomerase activity, ie., the ability to synthesize telomere DNA. Alternatively, the reconstitution can be only for "partial activities," as described in detail below. The invention include reconstitution of hTERT in such mTERT "knockout" mice, and the animals and their progeny produced by such reconstitution. The cloning and characterization of hTERT is described, e.g., in U.S. Ser. No. 08/854,050, filed May 9, 1997; in U.S. Ser. No. 08/915,503, U.S. Ser. No. 08/912,951, and, U.S. Ser. No. 08/911,312, all filed Aug. 14, 1997; and in U.S. Ser. No. 08/974,549, and U.S. Ser. No. 08/974,584, both filed on Nov. 19, 1997.

The assays of the invention can be used to assess the degree of purification, identify a new mTERT species, such as an mTERT allele, homologue, or isoform, or to screen for modulators (antagonists and agonists) of telomerase-mediated DNA replication. Methods for identifying modulators of a telomerase enzyme activity have been described in U.S. Pat. No. 5,645,986; and U.S. Ser. No. 08/151,477, filed Nov. 12, 1993; and U.S. Ser. No. 08/288,501, filed Aug. 10, 1994, and the reagents of the invention may be employed in such methods. Antagonists and agonists of mTERT can be used to modify the activity of other telomerase enzymes, such as hTERT (hTRT).

The invention contemplates screening for compositions capable of modifying the polymerase activity of telomerase enzyme, or a partial activity, by any means. In various embodiments, the invention includes: screening for antagonists that bind to mTERT's active site or interfere with transcription of its RNA moiety, as mTERC; screening for compositions that inhibit the association of nucleic acid and/or telomerase-associated compositions, such as the association of mTERC with mTERT or the association of mTERT with mouse p80-homologue or other telomerase-associated proteins, or association of mTERT with a telomere, chromosome, nucleosome or a nucleotide; screening for compositions that promote the dissociation or promote the association of the enzyme complex, such as an antibody directed to mTERC or mTERT; screening for agents that effect the processivity of the enzyme; and screening for nucleic acids and other compositions that bind to mTERT, such as a nucleic acid complementary to mTERC. The invention further contemplates screening for compositions that increase or decrease the transcription of the mTERT gene and/or translation of the mTERT gene product. These compositions can be used to modify the transcription or translation of other TERT genes, such as hTERT.

Screening for antagonist activity provides for compositions that decrease telomerase replicative capacity, thereby limiting the proliferative, replicative potential of indefinitely proliferating cells, or mortalizing otherwise immortal cells, such as cancer cells.

Screening for agonist activity or transcriptional or translational activators provides for compositions that increase the telomerase enzyme's telomere replicative capacity, or, alternatively, a partial activity as described herein. Such agonist compositions provide for methods of creating indefinitely proliferating cells, and immortalizing or increasing the proliferative capacity of otherwise normal, untransformed cells, including cells which can express useful proteins. Such agonists can also provide for methods of controlling cellular senescence, see co-pending U.S. Ser. Nos. 08/912,951 and 08/915,503.

The novel telomerase compositions and activity reconstitution assays of the invention also provide for a novel telomerase repeat amplification protocol assay (TRAP) and variations of this assay. The TRAP assay is an amplification-based method for detecting, determining, and measuring telomerase activity and is described in PCT Publication Nos. 97/15687 and 95/13381 and U.S. Pat. No. 5,629,154; see also U.S. Ser. No. 08/632,662, and U.S. Ser. No. 08/631,554, filed 15 Apr. 1996 and 12 Apr. 1996, respectively. See also, Kim (1994) supra. The present invention provides reagents useful for the TRAP assay as well as new amplification-based telomerase activity assays for a wide variety of applications. For example, TRAP assays comprising an mTERT protein or a telomerase enzyme complex of the invention can be used to screen for modulators of telomerase activity. Such compositions can also be used to modulate the activity of other telomerase enzymes, such as hTERT, or to act as a basis for identification of such human telomerase enzyme modulators.

The novel telomerase compositions of the invention can also be used in telomere length assays. Because of the relationship between telomerase activity and telomere length, the diagnostic and therapeutic methods of the invention can be used in conjunction with telomere length assays. A variety of telomere length assays have been described, see PCT Patent publication Nos. 93/23572, 95/13382, 95/13383, and 96/41016, and U.S. Ser. No. 08/660,402, filed 6 Jun. 1996; 08/479,916, filed Jun. 7, 1995; and, 08/475,778 and 08/487,290, both filed Jun. 7, 1995.

The invention provides a method of screening for telomerase modulators in animals by reconstituting a telomerase activity, or an anti-telomerase activity, into an animal, such as a transgenic, non-human animal. The invention provides for in vivo assays systems that include mouse "knockout" models in which the endogenous mTERT has been deleted, altered, or inhibited. The endogenous mTERT can be deleted, altered, or inhibited in either one or both endogenous mTERT alleles. One embodiment provides for a telomerase deficient mouse, or mTERT "knockout" mouse, and its progeny. Other embodiments provide for "knockout" mice, and their progeny, whose ability to express the telomerase RNA moiety and/or telomerase-associated proteins has also been deleted, altered, or modified. In one embodiment, an exogenous telomerase activity (such as human TERT), or endogenous mouse telomerase activity, full or partial, wild-type or modified, is reconstituted in the "knock-out" mouse or increased in an otherwise normal mouse. In alternative embodiments, endogenous mouse telomerase enzyme or mTERT activities, full or partial, can remain either in one or both alleles. The telomerase activity reconstituted in the "knockout" mouse model can include modified endogenous or exogenous TERT, e.g., mTERT or hTERT alone, hTERT and hTERC, mTERT and mTERC, mTERT and hTERC. The invention also provides for transgenic cells and animals, in addition to mice, where mTERT and/or murine telomerase activity has been inserted through recombinant methodologies. The non-human transgenic animals of the invention also provide for methods of expressing large amounts of fully or partially active telomerase enzyme and mTERT. Transgenic animals also provide for the construction of indefinitely proliferating cells and the immortalization of otherwise normal cells, which can then be used, for example, to express compositions of interest.

In one embodiment of the invention, recombinant mTERT is expressed in normal, diploid mortal cells to provide for indefinitely proliferating cells, immortalization of cells, or to facilitate long-term culture or replication of the cells. Telomerase enzyme complex components, such as nucleic acid telomeric sequence template molecules (mTERC, for example) or other associated proteins, that are beneficial for expression or act as modulators of activity, can also be co-expressed. This invention provides methods to obtain indefinitely proliferating cells and diploid immortal cells with an otherwise normal phenotype and karyotype. This aspect of the invention is of enormous practical and commercial utility; for example, the FDA and public would value the production of recombinant proteins from normal cells to minimize concern regarding viral or other contamination of the products made from such cells as are commonly used today. The present invention allows one to produce indefinitely proliferating and immortal hybrids of B lymphocytes and myeloma cells to obtain hybridomas for monoclonal antibody production. Using the methods of this invention, transfection of mTERT protein and telomerase enzyme activity into B lymphocytes allows one to generate indefinitely proliferating cells and immortal cells for antibody production.

Another embodiment provides for methods for introducing recombinant mTERT and/or telomerase associated RNA and other compounds of the invention into cells to produce a commercially desirable protein. For example, by the methods of the invention an indefinitely proliferating and an immortal, yet karyotypically normal, pituitary cell that makes hormones, such as growth hormone, could be produced for commercial use. In a variation of this embodiment, a normal cell is removed from the animal, transformed into an indefinitely proliferating cell, or immortalized, using the methods and reagents of the invention, transfected with a gene of interest such that the gene is expressed at appropriate levels and introduced back into the animal such that the transfected gene expresses a molecule that impacts the health or other qualities of the animal.

Another embodiment of the invention involves a similar method, but the cell is a "universal donor cell" which has been modified to delete histocompatibility antigens or modified in some way to prevent or decrease the possibility of immune rejection. A complication arising from the re-introduction of these cells into an animal is the possibility that the cells may lose growth control and change to a state of uncontrolled cell growth, becoming a cancer, tumor or other malignancy. The present invention solves this complication by providing means to express mTERT or other telomerase components conditionally and/or by providing means for knocking out telomerase enzyme, mTERT or a telomerase enzyme complex component necessary for activity. Moreover, even "mortal" cells used in transplantation or for other purposes can be mortalized by such methods of the invention. Without an active telomerase, the cells are irreversibly mortal, thus decreasing the probability of cancerous or malignant transformation after transplantation or other re-introduction into a host organism. This would not affect the cell's function, as telomerase enzyme is not normally active in somatic cells.

The present invention also provides methods and reagents relating to cis-acting transcriptional and translational regulatory elements. Examples of cis-acting transcriptional regulatory elements include promoters and enhancers of the mTERT gene. Examples of cis-acting translational regulatory elements include elements that stabilize mRNA or protect the transcript from degradation. The identification and isolation of cis- and trans-acting regulatory agents provide for further methods and reagents for identifying agents that modulate transcription and translation of mTERT and other telomerase enzymes and TERTs, such as hTERT. While many aspects of these methods and reagents are described more fully below, U.S. Ser. No. 08/714,482, filed Sep. 16, 1996, provides useful information relating to reagents and screens for the hTERC (hTR) promoter that usefully supplements understanding of certain embodiments of the present invention relating to the mTERC promoter and isolated and recombinant molecules comprising all or part of the mTERT promoter and related methods.

The present invention also provides novel methods and reagents for immunizing animals to generate an anti-murine telomerase enzyme and an anti-mTERT immune response. While these methods and compositions are fully described below, see also U.S. Ser. No. 08/734,052, filed Oct. 18, 1996, for additional useful information.

1. Nucleic Acids Encoding mTERTs

This invention for the first time provides the identification, cloning and characterization of the mTERT gene, related polypeptide, and telomerase enzyme complexes including, as well as providing novel reagents including or derived from these new compositions that complement this significant achievement.

The invention provides for novel means of expressing mTERT in vitro, ex vivo, and in vivo, thereby providing a means to increase or decrease endogenous or exogenous TERT expression and activity. These novel means of expressing mTERT also provide for in vitro, ex vivo, and in vivo assays to screen for telomerase activity modulators, including agonist and antagonists. Screening for agonist and antagonist activity further provides for compositions that can decrease or increase the telomerase enzyme and TERT's ability to extend telomeres, i.e., telomere replicative capacity. Agonist compositions and methods for creating indefinitely proliferating cells and immortalizing otherwise normal, untransformed cells, thereby extending cell life, including cells which can express useful proteins and other compounds, are also provided. Such agonists and methods provide a means to control cellular senescence and so ameliorate the diseases associated with aging and debilitating conditions.

Telomerase activity has been identified as an important cancer marker, one whose levels can predict the outcome or seriousness of disease, as described in U.S. Pat. Nos. 5,489,508; 5,648,125 and 5,639,613. Antagonist compositions, means for screening for such compositions and methods for inhibiting mTERT and telomerase enzyme in continuously proliferating, transformed and immortal cells, thereby shortening cell life, thus are also provided by the invention. Antagonists of mTERT can also be antagonists of hTERT.

In another embodiment, the novel compositions of the invention, including mTERT-encoding nucleic acids and anti-mTERT antibodies, can also be used to identify and purify mTERT isoforms, homologues, and alleles. In an alternative embodiment, mTERT and known telomerase enzyme complex components are used to identify additional telomerase-associated components. In one embodiment, the nucleic acids of the invention are used to reconstitute mTERT activity in vitro, ex vivo, or in vivo. The nucleic acids of the invention can also be used modify the activity of mTERT, as for example, the invention provides antisense nucleotide sequences, telomerase-inhibiting ribozymes, dominant negative mTERT proteins, and gene therapy vectors encoding the same.

The invention also provides for methods and associated reagents incorporating the nucleic acids of the invention that include or can be used to identify mTERT-specific cis-acting transcriptional control elements, such as mTERT promoters, and trans-acting elements that bind to such sequences.

The invention can be practiced in conjunction with any method or protocol known in the art, which are well described in the scientific and patent literature. Therefore, only a few general techniques will be described prior to discussing specific methodologies and examples relative to the novel reagents and methods of the invention.

a. General Techniques

The mTERT, telomerase enzyme and telomerase-associated nucleic acids of this invention, whether RNA, cDNA, genomic DNA, or a hybrid thereof, or synthetically prepared using non-naturally occurring reagents, may be isolated from a variety of sources or may be synthesized in vitro. Nucleic acids coding for the protein compositions of the invention can be expressed in transgenic animals, transformed cells, in a cell lysate, or in an isolated, partially purified or a substantially pure form. Techniques for nucleic acid manipulation of genes encoding the mTERT species of the invention, such as generating libraries, subcloning into expression vectors, labeling probes, sequencing DNA, and DNA hybridization are described generally in Sambrook, ed., MOLECULAR CLONING: A LABORATORY MANUAL (2ND ED.), Vols. 1–3, Cold Spring Harbor Laboratory, (1989) ("Sambrook"); CURRENT PROTOCOLS IN MOLECULAR BIOLOGY, Ausubel, ed. John Wiley & Sons, Inc., New York (1997) ("Ausubel"); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993) ("Tijssen"). Sequencing methods typically can include dideoxy sequencing (Sequenase, U.S. Biochemical), however, other kits and methods are available and well known to those of skill in the art.

Nucleic acids and proteins are detected and quantified in accordance with the teachings and methods of the invention described herein by any of a number of general means well known to those of skill in the art. These include, for example, analytical biochemical methods such as spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immuno-fluorescent assays, and the like, Southern analysis, Northern analysis, Dot-blot analysis, gel electrophoresis, RT-PCR, quantitative PCR, other nucleic acid or target or signal amplification methods, radiolabeling, scintillation counting, and affinity chromatography, to name only a few.

b. Isolation, Synthesis, and Purification of Nucleic Acids Encoding mTERT

In another embodiment, the invention provides methods to identify and isolate mTERT isoforms, homologues, and alleles. The invention provides a recitation of structural features common to mTERT species of the invention, ie., motifs which are mTERT specific and motifs which can be used to identify additional mTERT species (see FIGS. 4 and 5). The murine, or Mus, specific TERT motif (specifically, Motif T, Motif 1, Motif 2, Motif A, Motif B', Motif C, Motif D, and Motif E) sequences of the invention are shown in FIG. 5.

Typically, TERTs are large, basic, proteins having telomerase-specific amino acid motifs, some of which are reverse transcriptase (RT) motifs, as disclosed herein. Because these motifs are conserved across diverse organisms, additional murine TERT mRNA, cDNA and genes can be obtained or identified using primers, nucleic acid probes, and antibodies to one or more of the motif sequences.

Sequence analysis of mTERT shows that it contains amino acid regions, or motifs, that identify it as a reverse transcriptase (RT) enzyme. FIGS. 3, 4, and 5, show the alignment of mTERT with other TERT proteins. The RT region is in the approximately middle third of the mTERT mRNA (cDNA, SEQ ID NO:1), is the most structurally conserved region of mTERT as compared to RTs from other organisms. Thus, in one embodiment, the nucleic acids comprising this and the other motifs (described in FIGS. 4 and 5) can be used as probes to identify additional mTERT species. In an alternative embodiment, primers able to amplify these motif-encoding regions can directly generate new mTERT species, or generate nucleic acids to be used as hybridization probes for such mTERT specie identification. In another embodiment, nucleic acids comprising regions poorly conserved between TERTs, particularly hTERT, can be used to identify TERTs closely related to mouse mTERT, such as those from other rodent species. Alternatively, motif regions can be excised by restriction enzyme digestion for use as hybridization probes, as described below. Probes targeting mTERT motifs can also be produced synthetically.

The motifs found in TERTs, while similar to those found in other reverse transcriptases, have particular hallmarks. For example, in motif C the two aspartic acid residues (DD) that coordinate active site metal ions (see, Kohlstaedt (1992) *Science* 256:1783; Jacobo-Molina (1993) *Proc. Natl. Acad. Sci. USA* 90:6320; Patel (1995) *Biochemistry* 34:5351) occur in the context hxDD(F/Y) (SEQ ID NO:85) in the telomerase RTs compared to (F/Y)xDDh (SEQ ID NO:86) in the other RTs (where h is a hydrophobic amino acid, and "x" is any amino acid; see Xiong (1990) *EMBO J*. 9:3353; Eickbush, in *The Evolutionary Biology of Viruses* (S. Morse, Ed., Raven Press, N.Y., p. 121, 1994). Another systematic change characteristic of the telomerase reverse transcriptase enzymes occurs in motif E, where WxGx (SEQ ID NO:87) is a consensus among the telomerase proteins, whereas hLGxxh (SEQ ID NO:88) is characteristic of other RTs (Xiong, supra; Eickbush supra). This motif E is called the "primer grip" (Jacobo-Molina (1993) supra, Wohrl (1997) *J. Biol. Chem.* 272:17581–17587) and mutations in this region affect priming in RNA polymerases but not priming in DNA polymerases (Powell (1997) *J. Biol. Chem.* 272:13262). In addition, the distance between motifs A and B' is longer in the TERTs than is typical for other RTs, which may be accommodated as an insertion within the "fingers" region of the structure which resembles a right hand (see Kohlstaedt, supra; Jacobo-Molina, supra; and Patel, supra).

The T motif ("motif T") is an additional hallmark of TERT proteins (see FIGS. 3 and 4). The T motif comprises a sequence that can be described using the formula: W-$X_{12}$-FFY-X-T-E-$X_{10-11}$-R-$X_3$-W (SEQ ID NOS:89 and 90), or, alternatively described using the formula: Trp-$R_1$-$X_7$-$R_1$-$R_1$-$R_2$-X-Phe-Phe-Tyr-X-Thr-Glu-$X_{8-9}R_3$-$R_3$-Arg-$R_4$-$X_2$-Trp SEQ ID NOS:91 and 92), where X is any amino acid and the subscript refers to the number of consecutive residues, $R_1$ is leucine or isoleucine, $R_2$ is glutamine or arginine, $R_3$ is phenylalanine or tyrosine, and $R_4$ is lysine or histidine.

The T motif can also be described using the formula: Trp-$R_1$-$X_4$-h-h-X-h-h-$R_2$-p-Phe-Phe-Tyr-X-Thr-Glu-X-p-$X_3$-p-$X_{2-3}$-$R_3$-$R_3$-$R_3$-Arg-$R_4$-$X_2$-Trp (SEQ ID NOS:62 and 63) where X is any amino acid, a subscript refers to the number of consecutive residues, $R_1$ is leucine or isoleucine, $R_2$ is glutamine or arginine, $R_3$ is phenylalanine or tyrosine, R4 is lysine or histidine, h is a hydrophobic amino acid selected from Ala, Leu, Ile, Val, Pro, Phe, Trp, and Met, and p is a polar amino acid selected from Gly, Ser, Thr, Tyr, Cys, Asn and Gln.

Motif 1 can also be described using the formula: L-R-$X_2$-P-K-$X_3$ (SEQ ID NO:93), or, alternatively, h-R-h-I-P-K-$X_3$ (SEQ ID NO:94).

Motif 2 can also be described using the formula: X-R-X-I-X (SEQ ID NO:95), or, alternatively, (F/L)-R-h-I-$X_2$-h (SEQ ID NO:65).

Motif A can also be described using the formula: $X_4$-F-$X_3$-D-$X_4$-Y-D-$X_2$ (SEQ ID NO:96), alternatively P-X-L-Y-F-h-X-h-D-h-$X_3$-Y-D-X-I (SEQ ID NO:97)

Motif B' can also be described using the formula: Y-$X_4$-G-$X_2$-Q-G-$X_3$-S-$X_8$ (SEQ ID NO:98), or, alternatively Q-$X_2$-G-I-P-Q-G-S-X-L-S-X-h-L (SEQ ID NO:99).

Motif C can also be described using the formula: $X_6$-D-D-X-L-$X_3$ (SEQ ID NO:100), or, alternatively, L-L-R-F-X-D-D-F-L-L-X-T (SEQ ID NO:101).

It will be apparent to one of skill that, provided with the reagents, and the mTERT sequences disclosed herein for those reagents, and the methods and guidance provided herein (including specific methodologies described infra), mTERT genes and proteins can be obtained, isolated and produced in recombinant form by one of ordinary skill. For example, primers (e.g., degenerate amplification primers) are provided that hybridize to gene sequences encoding motifs characteristic of mTERT species to identify further mTERT isoforms, homologues, and alleles. One or more primers or degenerate primers that hybridize (as discussed infra) to sequences encoding the above described mTERT motifs, or combinations of such motifs or TERT consensus sequence (as shown in FIGS. 4 and 5), can be prepared based on the codon usage of the target organism, and used to amplify the mTERT gene sequence from genomic DNA or cDNA prepared from the target organism. Use of degenerate primers is well known in the art and entails sets of primers that hybridize to the set of nucleic acid sequences that can potentially encode the amino acids of the target motif, taking into account codon preferences and usage of the target organism, and by using amplification (e.g., PCR) conditions appropriate for allowing base mismatches in the annealing steps. Typically two primers are used; however, single primer (or, in this case, a single degenerate primer set) amplification systems are well known and may be used to obtain mTERT encoding nucleic acids.

The T motif is necessary for at least one of telomerase's activity, including enzymatic catalysis. The mTERT of the invention and fragments thereof which include the T motif provide for a preferred nucleic acid or amino acid sequence or subsequence to be used in methods of the invention, including, for example, methods for identifying and isolating mTERT alleles, isoforms, and homologues, or, as described below, for making dominant negative mutant constructs, see below.

The mTERTs of the invention can also be identified, isolated and expressed using methods of the invention, including: i) computer searches of murine DNA databases for DNAs containing sequences conserved with an mTERT specie and having sequence identity with TERT motifs and mTERT sequences described above, ii) hybridization with a probe from a known mTERT sequence to mouse mRNA, cDNA or RT DNA sequence or murine cDNA or genomic libraries, and iii) by PCR or other signal or target amplification technologies of mouse nucleic acid using primers complementary to regions highly conserved among different TERTs, such as the motifs of the invention. Amino acid sequences can be conserved, but, because of the degeneracy of the genetic code, codon usage bias, or amino acid changes, the DNA sequences corresponding to motif regions can be different between organisms. For this reason, one can employ in the methods nucleotides at the positions in the primers that are degenerate for a particular amino acid to ensure that one or more of the different primers can hybridize to an mTERT whose nucleotide sequence is not completely known. In performing PCR with such primers, one may take allowances for the degenerate positions probe by using conditions appropriate for allowing certain base mismatches to occur in the annealing steps of PCR, i.e., degenerate PCR conditions. Primers of the invention are used to identify murine mTERT species encompassed by the invention.

While methods for isolating total DNA or RNA are well known to those of skill in the art, e.g., see Tijssen and Sambrook, illustrative example of methods for identifying, characterizing and isolating mTERT nucleic acids of the invention are provided below.

i. Preparation and Screening of TERT-encoding DNA Libraries

There are numerous methods for isolating DNA sequences encoding the mTERT of the invention. For example, mTERT DNA can be identified by stringent hybridization and isolated from a murine genomic or cDNA library using oligonucleotide probes, typically labeled, having sequences complementary to mTERT sequences or subsequences, such as TERT motifs, as disclosed herein. For example, the mTERT encoded by the genomic and cDNA nucleic acid whose sequence is set forth in SEQ ID NO:1, can be used to construct such probes or primers. Such probes can be used directly in hybridization assays to isolate DNA encoding mTERT species. Alternatively probes can be designed for use in amplification techniques such as PCR.

The invention provides compositions and methods to screen both genomic and cDNA libraries for mTERT sequences. Screening cDNA libraries for coding sequences has certain advantages in that no intronic sequences are usually present. Screening genomic libraries has an advantage in that upstream and downstream cis-acting transcriptional regulatory elements can be identified and isolated, as well as introns, promoters and enhancers which may be beneficial to include in some expression vectors. Furthermore, in some species, the intronic or untranscribed mTERT sequences may be the most conserved. Accordingly, the invention provides for the isolation of mTERT genomic nucleic acids, including introns, protein-encoding exons, and transcribed and non-transcribed genomic sequences as additional reagents and means to identify and screen for mTERT isoforms, alleles and homologues.

Identification of mTERT cis-acting regulatory elements provides reagents and means to isolate further mTERT trans-acting regulatory compounds. Identification of such mTERT regulatory elements provides the means to design TERT modulating compounds which can be used to up- or down-regulate TERT transcription, translation, or assembly of a functional or partially functional (i.e., having "partial activity") TERT or telomerase enzyme. The invention also provides isolated and recombinant nucleic acids comprising the mouse genomic promoter region, as described below, and identified in SEQ ID NO:1.

To prepare a cDNA library, mRNA is isolated, reverse transcribed and inserted into vectors in accordance with general procedures well known in the art. The vectors are transfected into a recombinant host for propagation, screening and other applications. Methods for making and screening cDNA libraries are well known, see e.g, Gubler (1983) *Gene* 25:263–269; Shepard (1997) *Nucleic Acids Res.* 25:3183–3185; Davis (1997) *Proc. Natl. Acad. Sci. USA* 94:2128–2132; Alphey (1997) *Biotechniques* 22:481–484; and Sambrook. To make a genomic library, total DNA is extracted and purified by well-known methods (see, e.g., Sambrook, Ausubel). DNA of appropriate size is produced by known methods, such as mechanical shearing or enzymatic digestion, to yield DNA fragments, e.g., of about 12 to 20 kb. The fragments are then separated, as for example, by gradient centrifugation, or gel electrophoresis, from undesired sizes. Selected fragments can be inserted in bacteriophage or other vectors. These vectors and phage can be packaged in vitro, as described, e.g., in Sambrook. Recombinant phage can be analyzed by plaque hybridization as described, e.g., in Benton (1977) *Science* 196:180; Chen (1997) *Methods Mol Biol* 62:199–206. Colony hybridization can be carried out as generally described in the scientific literature, e.g., as in Grunstein (1975) *Proc. Natl. Acad. Sci. USA* 72:3961–3965; Yoshioka (1997) *J. Immunol Methods* 201:145–155; Palkova (1996) *Biotechniques* 21:982.

DNA encoding an mTERT isoform, homologue, or allele can be identified in either murine cDNA or genomic libraries by hybridization with nucleic acid probes of the invention, e.g., probes containing 10 to 20 to 50 or more contiguous nucleotides of SEQ ID NO:1, on Southern blots. Once identified, these DNA regions are isolated by standard methods familiar to those of skill in the art. Alternatively, RNA encoding mTERT protein may be identified by hybridization to nucleic acid probes in Northern blots or other formats; see, e.g., Sambrook for general procedures relating to such formats.

Oligonucleotides for use as probes can be chemically synthesized, as described below. Synthetic nucleic acids, including oligonucleotide probes and primers, mTERT coding sequences, antisense, ribozymes and the like can be prepared by a variety of solution or solid phase methods. Detailed descriptions of the procedures for solid phase synthesis of nucleic acids by phosphite-triester, phosphotriester, and H-phosphonate chemistries are widely available. For example, the solid phase phosphoramidite triester method of Beaucage and Carruthers using an automated synthesizer is described in Itakura, U.S. Pat. No. 4,401,796; Carruthers, U.S. Pat. Nos. 4,458,066 and 4,500,707; Carruthers (1982) *Genetic Engineering* 4:1–17; see also Needham-VanDevanter (1984) *Nucleic Acids Res.* 12:6159–6168; Beigelman (1995) *Nucleic Acids Res* 23: 3989–3994; Jones, chapt 2, Atkinson, chapt 3, and Sproat, chapt 4, in OLIGONUCLEOTIDE SYNTHESIS: A PRACTICAL APPROACH, Gait (ed.), IRL Press, Washington D.C. (1984); Froehler (1986) *Tetrahedron Lett.* 27:469–472; Froehler, *Nucleic Acids Res.* 14:5399–5407 (1986); Sinha, *Tetrahedron Lett.* 24:5843–5846 (1983); and Sinha, *Nucl. Acids Res.* 12:4539–4557 (1984); for synthesis of fluorescently labeled oligonucleotides and their application in DNA sequencing, see Markiewicz (1997) *Nucleic Acids Res.* 25:3672–3680; Shchepinov (1997) *Nucleic Acids Res.* 25:4447–4454, describing synthesis of a phosphoramidite synthon.

Methods to purify oligonucleotides include, for example, native acrylamide gel electrophoresis, anion-exchange HPLC, as described in Pearson (1983) *J. Chrom.* 255:137–149, and Ausserer (1995) *Biotechniques* 19:136–139; Arghavani (1995) *Anal. Biochem.* 231:201–209, using reversed-phase high-performance liquid chromatography, and the like. The sequence of the synthetic oligonucleotide can be verified using any chemical degradation method, e.g., see Maxam (1980) *Methods in Enzymol.* 65:499–560, Xiao (1996) *Antisense Nucleic Acid Drug Dev.* 6:247–258; or for solid-phase chemical degradation procedures, see e.g., Rosenthal (1987) *Nucleic Acids Symp.*

Ser. 18:249–252; to sequence phosphorothioate DNA, see Froim (1997) *Nucleic Acids Res.* 25:4219–4223.

ii. Amplification of Nucleic Acids Encoding TERT and Telomerase

The present invention provides oligonucleotide primers and probes that can hybridize specifically to nucleic acids having mTERT protein-encoding cDNA or genomic nucleic acid, such as the mTERT sequence of SEQ ID NO:1, encoding the polypeptide of SEQ ID NO:2. Such reagents can be used to identify any species of mTERT protein-encoding and genomic sequences. mTERT genomic sequences include intronic and genomic, non-transcribed sequences, promoters, and enhancers which can also be amplified using the PCR primers of the invention to identify new mTERT isoforms, alleles and homologues. Illustrative PCR primers and amplification methods are described below.

Amplification of mTERT sequences which are conserved amongst different mTERT species, i.e., consensus or motif mTERT sequences, as described above, can be used to generate oligonucleotides that are preferred reagents of the invention. The reagents are used as hybridization probes to identify and isolate additional mTERT species. These oligonucleotides can also be used as primers to amplify additional mTERT species directly, using any amplification technique, such as, for example RACE, as described below.

Oligonucleotides can be used to identify and detect additional mTERT species using a variety of hybridization techniques and conditions. One of skill in the art will appreciate that, whatever amplification method is used, if a quantitative result is desired, care must be taken to use a method that maintains or controls for the relative frequencies of the amplified nucleic acids. Suitable amplification methods include, but are not limited to: polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y. ("Innis")), ligase chain reaction (LCR) (Wu (1989) *Genomics* 4:560; Landegren (1988) *Science* 241:1077; Barringer (1990) *Gene* 89:117); transcription amplification (Kwoh (1989) *Proc. Natl. Acad. Sci. USA* 86:1173); self-sustained sequence replication (Guatelli (1990) *Proc. Natl. Acad. Sci. USA*, 87:1874); Q Beta replicase amplification (Smith (1997) *J. Clin. Microbiol.* 35:1477–1491, automated Q-beta replicase amplification (Burg (1996) *Mol. Cell. Probes* 10:257–271); and other RNA polymerase mediated techniques (e.g., NASBA, Cangene, Mississauga, Ontario); see also Berger (1987) *Methods Enzymol.* 152:307–316, Sambrook, and Ausubel, as well as Mullis (1987) U.S. Pat. Nos. 4,683,195 and 4,683,202; Arnheim (1990) *C&EN* 36–47; Lomell (1989) *J. Clin. Chem.* 35:1826; Van Brunt (1990) *Biotechnology* 8:291–294; Wu (1989) *Gene* 4:560; and Sooknanan (1995) *Biotechnology* 13:563–564. Methods for cloning in vitro amplified nucleic acids are described in Wallace, U.S. Pat. No. 5,426,039.

The invention provides for amplification and manipulation or detection of the products from each of the above methods to prepare DNA encoding mTERT protein or otherwise identical or complementary mTERT gene sequences. In PCR techniques, oligonucleotide primers complementary to the two borders of the DNA region to be amplified are synthesized and used (see, e.g., Innis). PCR can be used in a variety of protocols to amplify, identify, isolate and manipulate nucleic acids encoding mTERT. In these protocols, appropriate primers and probes for identifying and amplifying DNA encoding mTERT polypeptides and fragments thereof are generated that comprise all or a portion of any of the DNA sequences listed herein. PCR-amplified sequences can also be labeled and used as detectable oligonucleotide probes, but such nucleic acid probes can be generated using any synthetic or other technique well known in the art.

The present invention provides RACE-based methods for isolating mTERT nucleic acids. RACE is another PCR-based approach for DNA amplification. Briefly, this technique involves using PCR to amplify a DNA sequence using an introduced random 5' primer and a gene-specific 3' primer (5' RACE) or an introduced random 3' primer and a gene specific 5' primer (3' RACE). The amplified sequence is then subcloned into a vector where can be sequenced and manipulated using standard techniques. The RACE method is well known to those of skill in the art and kits to perform RACE are commercially available, e.g. Gibco BRL, Gaithersburg, Md., #18374-058 (5' RACE) or #18373-019 (3' RACE), see also Lankiewicz (1997) *Nucleic Acids Res* 25:2037–2038; Frohman (1988) *Proc. Natl. Acad. Sci. USA* 85:8998; and Doenecke (1997) *Leukemia* 11:1787–1792.

For 5' RACE, a primer, the gene-specific primer, is selected near the 5' end of the known sequence oriented to extend towards the 5' end. The primer is used in a primer extension reaction using a reverse transcriptase and mRNA. After the RNA is optionally removed, the specifically-primed cDNA is either: 1) "tailed" with deoxynucleotide triphosphates (dNTP) and dideoxyterminal transferase; then a primer that is complementary to the tail with a 5' end that provides a unique PCR site and the first gene-specific primer is used to PCR amplify the cDNA; subsequent amplifications are usually performed with a gene-specific primer nested with respect to the first primer, or 2) an oligonucleotide that provides a unique PCR site is ligated to an end of the cDNA using RNA ligase; then a primer complimentary to the added site and the first gene-specific primer is used to PCR amplify the cDNA, with subsequent amplifications usually performed with a gene-specific primer nested with respect to the first primer. Amplified products are then purified, usually by gel electrophoresis, then sequenced and the sequence examined to determine if the products contain the additional cDNA sequences desired.

For 3' RACE, an oligo dT-primer is annealed to the poly-A tails of an mRNA and then extended by a reverse transcriptase. Usually the oligo dT primer has a 5' end that provides a unique PCR site. The RNA is then removed, optionally, or dissociated, and the cDNA is amplified with a primer to the oligo dT tail and a gene-specific primer near the 3' end of the known sequence (oriented towards the 3' end). Subsequent amplifications are usually performed with a gene-specific primer nested with respect to the first primer. Amplified products are then purified, usually by gel electrophoresis, then sequenced and examined to determine if the products contain the additional cDNA sequences desired.

Another useful means of obtaining nucleic acids of the invention, such as large genomic clones, is to screen BAC or P1 murine genomic libraries. BACs, bacterial artificial chromosomes, are vectors that can contain 120+ Kb inserts (for example, see Asakawa (1997) *Gene* 191:69–79, for a description of the construction and of a human BAC library. BACs are based on the *E. coli* F factor plasmid system and are simple to manipulate and purify in microgram quantities. Because BAC plasmids are kept at one to two copies per cell, the problems of rearrangement observed with YACs, which can also be employed in the present methods, are reduced. For delivery of bacterial artificial chromosomes into mammalian cells see, e.g., Baker (1997) *Nucleic Acids*

*Res.* 25:1950–1956. BAC vectors can include marker genes for luciferase and green fluorescent protein (GFP). (Baker (1997) *Nucleic Acids Res* 25:1950–1956). P1 is a bacteriophage that infects *E. coli* that can contain 75–100 Kb DNA inserts (Mejia (1997) *Genome Res* 7:179–186; Ioannou (1994) *Nat Genet* 6:84–89), and are screened in much the same way as lambda libraries.

iii. Analysis of the mTERT Species: Isoforms, Alleles, Homologues

The mTERT-encoding nucleic acid sequences of the invention include isolated and recombinant nucleic acids relating to mTERT genes and gene products identified and characterized by analysis of mTERT sequences. Optimal alignment of sequences for comparison can use any means to analyze sequence identity (homology) known in the art, e.g., by the progressive alignment method of termed "PILEUP" (see below); by the local homology algorithm of Smith & Waterman, *Adv. Appl. Math.* 2: 482 (1981); by the homology alignment algorithm of Needleman & Wunsch, *J. Mol. Biol.* 48:443 (1970); by the search for similarity method of Pearson (1988) *Proc. Natl. Acad. Sci. USA* 85: 2444; by computerized implementations of these algorithms (GAP, BESTFIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by Higgins (1988) *Gene*, 73: 237–244; Corpet (1988) *Nucleic Acids Res.* 16:10881–90; Huang (1992) *Computer Applications in the Biosciences* 8:155–65, and Pearson (1994) *Methods in Molec. Biol.* 24:307–31), TreeAlign, MALIGN, and SAM sequence alignment computer programs; or, by inspection. See also Morrison (1997) *Mol. Biol. Evol.* 14:428–441, as an example of the use of PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp (1989) *CABIOS* 5: 151–153. The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison. For example, hTERT can be compared to other TERT species using the following parameters: default gap weight (3.00), default gap length weight (0.10), and weighted end gaps.

Another example of algorithm that is suitable for determining sequence similarity is the BLAST algorithm, which is described in Altschul (1990) *J. Mol. Biol.* 215: 403–410. Software for performing BLAST analyses is publicly available through the National Center for Biotechnology Information; see also Zhang (1997) *Genome Res.* 7:649–656 (1997) for the "PowerBLAST" variation. This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff (1989) *Proc. Natl. Acad. Sci. USA* 89:10915) alignments (B) of 50, expectation (E) of 10, M=5, N=−4, and a comparison of both strands. The BLAST algorithm performs a statistical analysis of the similarity between two sequences (see, e.g., Karlin (1993) *Proc. Natl. Acad. Sci. USA* 90: 5873–5787). One measure of similarity provided by the BLAST algorithm is the smallest sum probability (P(N)), which provides an indication of the probability by which a match between two nucleotide or amino acid sequences would occur by chance.

iv. Sequencing of mTERT DNA

Sequencing of isolated mTERT-encoding nucleic acid can be used to identify and characterize new mTERT species. mTERT protein-encoding sequences can be sequenced as inserts in vectors, as inserts released and isolated from the vectors or in any of a variety of other forms (i.e., as amplification products). mTERT-encoding inserts can be released from the vectors by restriction enzymes or amplified by PCR or transcribed by a polymerase. For sequencing of the inserts to identify full length mTERT coding sequences, primers based on the N- or C-terminus, or based on insertion points in the original phage or other vector, can be used. Additional primers can be synthesized to provide overlapping sequences. A variety of nucleic acid sequencing techniques are well known and described in the scientific and patent literature, e.g., see Rosenthal (1987) supra; Arlinghaus (1997) *Anal. Chem.* 69:3747–3753, for use of biosensor chips for sequencing; Healey (1997) *Anal. Biochem.* 251:270–279, describing fiberoptic DNA sensor arrays capable of detecting point mutations; Pastinen (1996) *Clin. Chem.* 42:1391–1397; Nyren (1993) *Anal Biochem.* 208:171–175.

v. Chromosomal Location of mTERT Encoding DNA

Identification of the location of the chromosomal location of mTERT coding sequences in different strains of wild-type mice will provide insights into mechanisms controlling the expression of the mTERT gene. Identification of the chromosomal location of mTERT in transgenic and mouse mTERT "knockout" mice also helps evaluate model systems. To ascertain the chromosomal location of the mTERT gene in a mouse, the segregation of mTERT in a Jackson Laboratory BSS interspecific backcross (see Rowe (1994) *Mammalian Genome* 5:253–274) was analyzed. Comparison of the allele distribution pattern of the mTERT locus with those of other loci previously mapped throughout the genome showed that mTERT cosegregated with D13Mit8 and D13Gor1 (Rowe (1994) supra, Xu (1996) *Mammalian Genome* 7:16–19). Comparing the BSS cross data to information from other linkage crosses in the Mouse Genome Database (MGD, see www.informatics.jax.org/mgd.html, The Jackson Laboratory), one finds that mTERT fits the composite mouse chromosome 13 map near MGD offset 40, in proximity to srd5a1, Adcy2, Dat1, and S1c9a3 genes. The specific region to which mTERT maps defines a conserved linkage group near the terminus of the short arm of human chromosome 5, band 15. Similar techniques can be used to map mTERT inserted into transgenic animals into which mTERT nucleic acid has been inserted to express murine telomerase as an exogenous entity; or, in "knockout" mice into which mTERT nucleic acid or a variant has been inserted to alter or abrogate the expression of endogenous mTERT.

c. Nucleic Acid Hybridization Techniques

The hybridization techniques disclosed herein can be utilized to identify, isolate and characterize genes and gene products (i.e., mRNA) encoding mTERT species. A variety of methods for specific DNA and RNA detection and measurement using nucleic acid hybridization techniques are known to those of skill in the art. See, e.g., NUCLEIC ACID HYBRIDIZATION, A PRACTICAL APPROACH, Ed. Hames, B. D. and Higgins, S. J., IRL Press, 1985; Gall (1989) *Proc. Natl. Acad. Sci. USA* 63:378; and Sambrook. The selection of a DNA hybridization format is often optional. For example, one method for evaluating the presence or absence of a DNA encoding an mTERT protein in a sample involves a Southern transfer. Briefly, the nucleic acid sample, such as digested murine DNA or mRNA, is run on agarose slab or polyacrylamide gel in buffer and transferred to membranes. Hybridization is carried out using nucleic acid probes. For the mTERT nucleic acids of this invention, the nucleic acid probes can comprise nucleic acid sequences conserved amongst mTERT nucleic acids. Preferably nucleic acid probes are 10 to 20 bases or longer in length, see, e.g., Sambrook for methods of selecting nucleic acid probe sequences for use in nucleic acid hybridization. Both quantitative and qualitative determination of the presence or absence of DNA or RNA encoding mTERT protein can be performed in accordance with the present methods.

Similarly, and as but one of many examples, a Northern transfer can be used for the detection of murine message RNA encoding mTERT polypeptides. For example, mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern transfers, probes, labeled probes or PCR amplification products can be used to identify the presence or absence of telomerase protein-encoding nucleic acid. The mTERT mRNA of the invention is often expressed in cells at such low levels that it can be difficult to detect by Northern blotting, even using the most sensitive assays. This can be true even with cells that express relatively high levels of mTERT mRNA, such as indefinitely proliferating, immortal and cancer cells. The low level of mTERT mRNA, even in mTERT-positive cells, ie., cells that express telomerase enzyme activity, such as cancer cells, is reflected by the low levels of mTERT protein that may be seen in such cells. Such protein can be detected by the detection methods of the invention, including immunoblotting (e.g., Western blots).

Sandwich assays can also be used to detect mTERT species. They are commercially useful hybridization assays for detecting or isolating protein or nucleic acid. Such assays utilize a "capture" nucleic acid or protein that is often covalently immobilized to a solid support and a labeled "signal" nucleic acid, typically in solution. A clinical or other sample provides the target nucleic acid or protein. The "capture" nucleic acid or protein and "signal" nucleic acid or protein hybridize with or bind to the target nucleic acid or protein to form a "sandwich" hybridization complex. To be effective, the signal nucleic acid or protein cannot hybridize or bind substantially with the capture nucleic acid or protein. Typically, oligonucleotide probes are labeled signal nucleic acids that are used to detect hybridization. Complementary probe nucleic acids or signal nucleic acids may be labeled by any one of several methods typically used to detect the presence of hybridized polynucleotides. Labels for autoradiography or autofluorography, such as $^3$H, $^{125}$I, $^{35}$S, $^{14}$C, or $^3$P-labeled probes or the like (see definition of label, above) can be used. Other labels include ligands which bind to labeled antibodies, fluorophores, chemiluminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal, i.e., antibody-antigen or complementary nucleic acid binding. The label may also allow indirect detection of the hybridization complex. For example, where the label is a hapten or antigen, the sample can be detected by using antibodies. In these systems, a signal is generated by attaching fluorescent or enzymatic molecules to the antibodies or, in some cases, by attachment of a radioactive label. The sensitivity of the hybridization assays may be enhanced through use of a target nucleic acid or signal amplification system which multiplies the target nucleic acid or signal being detected. In vitro amplification techniques suitable for amplifying sequences for use as molecular probes or for generating nucleic acid fragments for subsequent subcloning are known, as described above. These systems can be used to directly identify allelic variations or mutated sequences where the PCR or LCR primers or other reagents are designed to be extended or ligated only when a specific sequence is present. Alternatively, the specific sequences can be generally amplified using, for example, more generic PCR primers and the amplified target region later probed or sequenced to identify a specific sequence indicative of the allele or mutation.

It will be appreciated that nucleic acid hybridization assays for identification, diagnosis, sequencing, and the like, of mTERT can also be performed in an array-based format. Arrays involve a multiplicity of different "probe" or "target" nucleic acids (or other compounds) that are hybridized against a target nucleic acid. In this manner a large number of different hybridization reactions can be run essentially "in parallel". This provides rapid, essentially simultaneous, evaluation of a wide number of reactants. Methods of performing hybridization reactions in array based formats are well known to those of skill in the art, e.g., Jackson (1996) *Nature Biotechnology* 14:1685; Chee, *Science* 274:610 (1995); Pastinen (1997) *Genome Res.* 7:606–614, describing minisequencing on oligonucleotide arrays; and Drobyshev (1997) *Gene* 188:45–52, for sequence analysis by hybridization with oligonucleotide microchip.

An alternative means for determining the level of expression of a gene encoding a protein is in situ hybridization. In situ hybridization assays are well known and are generally described in Angerer (1987) *Methods Enzymol* 152:649. In an in situ hybridization assay, cells can be fixed to a solid support, typically a glass slide, or be free in solution. If DNA is to be probed, the cells are typically denatured with heat or alkali. The cells are then contacted with a hybridization solution at a moderate temperature to permit annealing of labeled probes specific to the nucleic acid sequence encoding the protein. The probes are typically labeled, i.e., with radioisotopes or fluorescent reporters. See also U.S. Pat. No. 5,583,016, U.S. Ser. Nos. 08/472,802 and 08/482,115, both filed Jun. 7, 1995; U.S. Ser. No. 08/521,634, filed Aug. 31, 1995; U.S. Ser. No. 08/714,482, filed Sep. 16, 1996; and U.S. Ser. Nos. 08/770,564 and 08/770,565, both filed 20 Dec. 1996; Soder (1997) Oncogene 14:1013–1021, all of which describe in situ hybridization of hTERC. Another well-known in situ hybridization technique is the so-called FISH fluorescence in situ hybridization, see Macechko (1997) J. Histochem. Cytochem. 45:359–363; and Raap (1995) Hum. Mol. Genet. 4:529–534.

d. Expression of Recombinant Telomerase and mTERT

To create cell-based assay systems to screen for modulators of mTERT, a variety of cell-based and in vitro systems are provided by the invention. The invention provides for methods and reagents to express the novel mouse telomerase enzymes and mTERTs of the invention in any prokaryotic, eukaryotic, yeast, fungal, plant, insect, human or animal cell, either alone or co-expressed with a telomerase-associated RNA moiety and/or other telomerase-associated proteins. The mTERT can be associated with mTERC or hTERC. The transfected mTERT can be expressed as an exogenous telomerase in a cell having full or partial endogenous telomerase enzyme activity. The mTERT can also be mutated or modified and subsequently transfected and expressed in a mouse cell.

In one embodiment, the endogenous mTERT can be first debilitated, or "knocked out" in either one or both alleles before introducing an exogenous TERT and/or TERC (e.g., altering endogenous mTERT activity and reconstituting with mTERT and mTERC, mTERT and hTERC, hTERT and mTERC, or, hTERT and hTERC) and other telomerase-associated components. The expression of mTERT in cells that have less than full or completely "knocked out" endogenous telomerase activity can reconstitute or re-introduce full or partial telomerase enzyme activity. Other telomerase-associated compositions, such as p80, can be co-expressed in these cell systems.

Using these or other in vitro or in vivo cell systems, the invention provides a means to assay for modulators of telomerase enzyme expression, including agonist and antagonists of telomerase enzyme and mTERT activity, transcription and translation of the mTERT gene, and assembly, processivity and substrate binding of mTERT and telomerase (see the further discussion of "partial" TERT activity, below). The invention also provides method for reconstitution of full or partial telomerase of mTERT activity in vitro.

Telomerase-encoding nucleic acids of the invention may be introduced into the genome or into the cytoplasm or nucleus of an animal or plant cell by a variety of conventional techniques, well described in the scientific and patent literature. A few selected illustrative general and specific teaching examples relevant to such technology are described below.

i. Cloning, Vectors, and Transcriptional Control Elements

The invention provides methods and reagents for expressing the novel murine telomerase enzyme and mTERT nucleic acids of the invention and further provides methods and reagents for identifying, isolating and using mTERT transcriptional and translational cis- and trans-acting control elements. After the coding region of a mTERT gene has been identified, the expression of natural, recombinant or synthetic mTERT-encoding or other (i.e., antisense, ribozyme) mTERT nucleic acids can be achieved by operably linking the coding region to a promoter (that can be telomerase-specific or not, constitutive or inducible), incorporating the construct into an expression vector, and introducing the vector (or plasmid) into a suitable host cell. Synthetic procedures may also be used. Typical vectors contain transcription and translation terminators, transcription and translation initiation sequences, and promoters useful for transcribing DNA into RNA.

The vectors optionally comprise generic expression cassettes containing at least one independent terminator sequence, sequences permitting replication of the cassette in eukaryotes, or prokaryotes, or both (e.g., shuttle vectors), and selection markers for both prokaryotic and eukaryotic systems. See, for example Roberts, Nature (1987) 328:731; Berger (1987) supra; Schneider (1995) Protein Expr. Purif. 6435:10; Sambrook and Ausubel. Product information from manufacturers of biological reagents and experimental equipment also provide information regarding known biological methods. Such manufacturers include the SIGMA chemical company (Saint Louis, Mo.), R&D systems (Minneapolis, Minn.), Pharmacia Biotech (Piscataway, N.J.), Clontech Laboratories, Inc. (Palo Alto, Calif.), Aldrich Chemical Company (Milwaukee, Wis.), GIBCO BRL Life Technologies, Inc. (Gaithersburg, Md.), Fluka Chemica-Biochemika Analytika (Fluka Chemie AG, Buchs, Switzerland), Applied Biosystems (Foster City, Calif.), as well as many other commercial sources known to one of skill. Promoters and vectors useful in regards in this invention can also be isolated from natural sources, obtained from such sources as the ATCC or from GenBank libraries, or prepared by synthetic methods, as described herein.

Various embodiments of the invention include use of inducible and constitutive promoters, depending on the expression system and desired levels of control of expressed protein. For example, the Tet-On/Tet-Off systems available from Clontech are useful in this regard. Viral, prokaryotic or eukaryotic promoters can be incorporated in expression vectors or expression cassettes. For example, highly efficient viral promoters can be used in the expression vectors of the invention, including cytomegalovirus (CMV) immediate early promoter, Rous sarcoma virus (RSV), murine leukemia virus (SL3-3) and simian virus 40 (SV40) early promoters. Other viral sequences, such as adenovirus tripartite leader (TPL) sequences, can also increase expression yields in eukaryotic expression systems (see, e.g., Lee (1997) Mol. Cells 7:495–501).

The telomerase enzyme and mTERT of the invention can be expressed in vectors which are transiently expressed in cells using, e.g., episomal vectors such as those derived from vaccinia virus, see Cooper (1997) Proc Natl Acad Sci USA 94:6450–6455; Muruve (1997) Transplantation 64:542–546. Alternatively, mTERT coding sequences can be inserted into the host cell genome becoming an integral part of the host chromosomal DNA, using for example, retroviral vectors derived from, e.g., SIV or HIV, see, e.g. Naldini (1996) Science 272:263–267; Vanin (1997) J. Virol. 71:7820–7826; Zufferey (1997) Nat. Biotechnol. 15:871–875, describing attenuated lentiviral vector gene delivery in vivo; Feng (1997) Nat Biotechnol 15:866–870, describing stable in vivo gene transduction via adenoviral/retroviral chimeric vector.

Expression vectors can contain selection markers that confer a selectable phenotype on transformed cells and sequences coding for episomal maintenance and replication such that integration into the host genome is not required. For example, the marker may encode antibiotic resistance, particularly resistance to chloramphenicol, kanamycin, G418, bleomycin and hygromycin, to permit selection of those cells transformed with the desired DNA sequences, see, e.g., Blondelet-Rouault (1997) *Gene* 190:315–317; Aubrecht (1997) *J. Pharmacol. Exp. Ther.* 281:992–997. Because selectable marker genes conferring resistance to substrates like neomycin or hygromycin can in certain cases only be utilized in tissue culture, chemoresistance genes are also used as selectable markers in vitro and in vivo. Various target cells are rendered resistant to anticancer drugs by transfer of chemoresistance genes encoding P-glycoprotein, multidrug resistance-associated protein-transporter, dihydrofolate reductase, glutathione-S-transferase, O 6-alkylguanine DNA alkyltransferase, or aldehyde reductase (Licht (1997) *Stem Cells* 15:104–111), and the like.

A DNA or RNA sequence coding for an mTERT protein, e.g., a cDNA sequence encoding the full length mTERT, can be combined with transcriptional (such as promoters and enhancers) and translational regulatory sequences which will direct the transcription and translation of the nucleic acid in a constitutive or a cell-specific or tissue-specific manner. A wide variety of well known transcriptional regulatory elements can be included in the vectors selected to express an mTERT protein of the invention. mTERT promoter constructs which direct the expression of mTERT in its native state are provided by the invention. Additional mTERT promoters can be identified by analyzing the 5' sequences of murine genomic clones. Sequences controlling eukaryotic gene expression have been extensively studied, and promoters have characteristic subsequences. For instance, promoter sequence elements include the TATA box consensus sequence (TATAAT), which is usually 20 to 30 base pairs upstream of the transcription start site. In most instances, the TATA box is required for accurate transcription initiation. In construction of recombinant expression cassettes of the invention, a recombinant or isolated promoter fragment, either related to the murine telomerase of this invention or heterologous thereto, may be employed which will direct expression of the gene in all or only some of the tissues of a transgenic organism, depending on the promoter and conditions employed. Promoters that drive expression continuously under physiological conditions, ie., "constitutive" promoters, are active under most environmental conditions and states of development or cell differentiation.

In some expression systems, to ensure optimal polypeptide expression levels, a polyadenylation region at the 3'-end of the coding region can be included. The polyadenylation region can be derived from the natural gene or from any of a variety of other genes, e.g., see de Moor (1997) *Mol. Cell. Biol.* 17:6419–6426.

ii. Transformation of Cells with mTERT-vectors

There are several well-known methods of introducing nucleic acids into bacterial and other cells, a process often called "transforming," any of which may be used in the methods of the present invention (see Sambrook). Techniques for transforming a wide variety of animal and plant cells are well known and described in the technical and scientific literature. See, e.g., Weising (1988) *Ann. Rev. Genet.* 22:421–477, for plant cells and Sambrook for animal and bacterial cells. Specific examples of methods of expressing the novel murine telomerase proteins of the invention are described below. For example, these include fusion of the recipient cells with bacterial protoplasts containing mTERT DNA, DEAE dextran transformation, infection with viral vectors, and the like.

Methods for transforming bacterial cells are well known in the art, and include, e.g., electroporation and heat shock of competent cells (see, e.g., Sambrook). Bacterial strains which can be used to express telomerase nucleic acid include, e.g., *Escherichia coli, Bacillus subtillus, Streptococcus cremoris, Streptococcus lactis, Streptococcus thermophilus, Leuconostoc citrovorum, Leuconostoc mesenteroides, Lactobacillus acidophilus, Lactobacillus lactis, Bifidobacterium bifidum, Bifidobacteriu breve*, and *Bifidobacterium longum*. To simplify identification of colonies of bacteria transformed with vectors containing the inserts, many cloning vectors have restriction enzyme sites or other splicing sites located within a coding sequence for an enzyme, such as, e.g., beta-galactosidase. If an insert has successfully been inserted into the vector at the restriction or splicing sites, the enzyme is either activated or inactivated. After transformation of the bacteria with the vector, colonies grown in the presence of isopropyl-D-thiogalactoside (IPTG) (for beta-galactosidase) appear white, while the colonies derived from a bacteria which did not incorporate the insert appear blue in the presence of the substrate. Thus, even if the frequency of ligation of the insert into the vector was low, one can pick the few colonies that contain inserts over the many that do not.

In addition to bacterial expression systems, the TERT and telomerase-associated proteins of this invention can be expressed in other systems, such as yeast, insect (baculovirus), mammalian and plant cells. The system used will depend on a variety of factors, including activities and amounts desired.

Yeast expression systems, being eukaryotic, provide an attractive alternative to bacterial systems for some applications; for an overview of yeast expression systems, see *Protein Engineering Principles and Practice*, eds. Cleland et al., Wiley-Liss, Inc. p 129 (1996). A variety of yeast vectors are publicly available. For example, the expression vector pPICZ B (Invitrogen, San Diego, Calif.) has been modified to create expression vectors of the invention to express the mTERT of the invention in yeast, such as *Pichia pastoris*. Yeast episomal plasmids comprising inducible promoters can be used for the intracellular expression of protein. Vectors include the pYES2 expression vector (Invitrogen, San Diego, Calif.) and pBS24.1 (Boeke (1984) *Mol. Gen. Genet.* 197:345); see also Jacobs (1988) *Gene* 67:259–269. Yeast promoters for yeast expression vectors suitable for the expression of an mTERT include the inducible promoter from the alcohol dehydrogenase gene, ADH2, also called the yeast alcohol dehydrogenase II gene promoter (ADH2P) (La Grange (1997) *Appl. Microbiol. Biotechnol.* 47:262–266). In another embodiment, the TERT to be expressed can also be fused at the amino terminal end to the secretion signal sequence of the yeast mating pheromone alpha-factor (MF alpha 1S) and fused at the carboxy terminal end to the alcohol dehydrogenase II gene terminator (ADH2T), see van Rensburg (1997) *J. Biotechnol.* 55:43–53. The yeast alpha mating pheromone signal sequence allows for secretion of the expressed telomerase. Direct intracellular expression of mTERT is useful for a variety of cell-based screens or mTERT protein production or telomerase enzyme reconstitution.

Yeast strains which can be used to express exogenous nucleic acids include *Pichia pastoris, Hansenula polymorpha, Torulopsis holmil, Saccharomyces fragilis, Saccharomyces cerevisiae, Saccharomyces lactis*, and *Candida pseudotropicalis*. A large number of vectors are available for *S. cerevisiae*. *Kluyveromyces lactis* and the methylotrophs *Hansenula polymorphas* and *Pichia pastoris* can offer certain advantages over baker's yeast *S. cerevisiae* for the production of certain proteins, see Gellissen (1997) *Gene* 190:87–97; Wegner (1990) *FEMS Microbiol. Rev.* 87:279.

The present invention also provides insect expression systems to express large amounts of recombinant mTERT and telomerase enzyme of the invention. A commonly used insect system utilizes *Spodoptera frugiperda* infected with a baculovirus, such as *Autographa californica* nuclear polyhedrosis virus. This virus can be used to infect Sf21 (Deutschmann (1994) *Enzyme Microb Technol* 16:506–512) or Sf9 cells (MaxBac 2.0, Invitrogen, San Diego, Calif.) (Zhu (1996) *J. Virol. Methods* 62:71–79) derived from *Spodoptera frugiperda*, High Five cells derived from *Trichoplusia ni* insect cells (Parrington (1997) *Virus Genes* 14:63–72), and *Lymantria dispar* (Vaughn (1997) *In Vitro Cell Dev Biol Anim* 33:479–482); see also Grabherr (1997) *Biotechniques* 22:730–735). Baculovirus transfer vectors can be used to replace the wild-type AcMNPV polyhedron gene with a heterologous gene of interest. Sequences that flank the polyhedrin gene in the wild-type genome are positioned 5' and 3' of the expression cassette on the transfer vectors. Following cotransfection with AcMNPV DNA, a homologous recombination event occurs between these sequences resulting in a recombinant virus carrying the gene of interest and the polyhedrin or p10 promoter. Baculovirus expression vectors are publicly available, such as pAC360 (Invitrogen, San Diego, Calif.). In addition to manufacturers' instructions accompanying the commercially available baculovirus systems, see, e.g., "Current Protocols in Molecular Biology," Ausubel, Chapter 16.

The present invention also provides methods and reagents for recombinant mTERT and telomerase enzyme expression in plant cell systems. Constitutive promoters of plants include the cauliflower mosaic virus (CaMV) 35S transcription initiation region, the 1'- or 2'-promoter derived from T-DNA of *Agrobacterium tumafaciens*, the promoter of the tobacco mosaic virus and transcription initiation regions from various plant genes known to those of skill in the art. The promoter may direct expression in only a specific tissue (tissue-specific promoters) or may be under environmental control (inducible promoters). Examples of tissue-specific plant promoters under developmental control include promoters that initiate transcription only in certain tissues, such as fruit, seeds, or flowers. The tissue specific E8 promoter from tomato is particularly useful for directing gene expression so that a desired gene product is located in fruits. Other suitable promoters include those from genes encoding embryonic storage proteins. Examples of environmental conditions that may affect transcription by inducible promoters include anaerobic conditions, elevated temperature, or the presence of light.

Plants can be transformed using viral vectors, such as, for example, tobacco mosaic virus derived vectors, to express recombinant telomerase enzyme or mTERT of the invention. Selection and construction of vectors and techniques for transforming a wide variety of plant cells are well known, e.g., see Hamamoto, U.S. Pat. No. 5,618,699. For example, mTERT constructs can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch, *Science* (1984) 233:496, and Fraley (1983) *Proc. Natl Acad. Sci USA* 80:4803; see also Chong (1997) *Transgenic Res.* 6:289–296, describing *Agrobacterium tumefaciens*-mediated leaf disc transformation methods. Plant regeneration from cultured protoplasts is described in Evans, PROTOPLASTS ISOLATION AND CULTURE, HANDBOOK OF PLANT CELL CULTURE, pp. 124–176, Macmillian Publishing Company, New York, 1983; and Binding, REGENERATION OF PLANTS, PLANT PROTOPLASTS, pp. 21–73, CRC Press, Boca Raton, 1985. Regeneration can also be obtained from plant callus, explants, organs, or parts thereof. Such regeneration techniques are described generally in Klee (1987) *Ann. Rev. of Plant Phys.* 38:467; Jafari (1995) *Acta Biol. Hung.* 46:51–59.

The invention provides methods and reagents for expression of mTERT and telomerase enzyme in mortal, transformed, or transformed immortal indefinitely proliferating mammalian cells using a wide variety of combinations of transcriptional control elements (e.g., promoters and enhancers), translational control elements, vectors (plasmid, viral, episomal, integrating), selectable marker genes, and related agents and cells. In some embodiments, endogenous mTERT, or mTERT and mTERC, activity can be debilitated, modified or fully deleted, ie., "knocked out," before insertion of vectors encoding modified endogenous or exogenous TERT (e.g., hTERT), TERC (e.g., hTERC) or other telomerase enzyme-associated compositions of the invention. The endogenous mTERT can be debilitated or deleted in either one or both alleles. The endogenous mTERC can also be debilitated or deleted in either one or both alleles. In an alternative embodiment, the mTERT of the invention or a variant, such as a deletion variant, is introduced into the cell to produce such a "knock-out" cell or animal.

Promoters can be constitutive or inducible, as described above. Vectors and promoters can be "transcriptionally targeted" to restrict the expression of the TERT sequence to appropriate cells. If the expression is to be used in a therapeutic method, such as gene therapy, there may be a therapeutic window for certain proteins such that levels of expression below and above certain thresholds may be ineffective or toxic, requiring vectors that allow exogenous control of expression, so that levels of the therapeutic protein can be raised or lowered according to therapeutic need. See e.g., Miller (1997) *Hum. Gene Ther.* 8:803–815; Walther (1996) *J. Mol. Med.* 74:379–392; Walther (1997) *Gene Ther.* 4:544–552.

In one embodiment of the invention, recombinant mTERT is expressed in normal, diploid mortal cells to create an indefinitely proliferating cell or to immortalize them. Illustrative vectors incorporating mTERT genes and coding sequences for the production of indefinitely proliferating and immortal B lymphocytes to obtain cells for monoclonal antibody production include, e.g., adenovirus-based vectors (Cantwell (1996) *Blood* 88:4676–4683; Ohashi (1997) *Proc Natl Acad Sci USA* 94:1287–1292), Epstein-Barr virus-based vectors (Mazda (1997) *J Immunol Methods* 204:143–151), adenovirus-associated virus vectors, Sindbis virus vectors (Strong (1997) *Gene Ther* 4: 624–627), Herpes simplex virus vectors (Kennedy (1997) *Brain* 120:1245–1259) and retroviral vectors (Schubert (1997) *Curr Eye Res* 16:656–662). The present invention provides a variety of vectors for introducing mTERT and telomerase enzyme into cells to produce an indefinitely proliferating or immortal normal cell that in turn produces a commercially desirable protein, such as pituitary cells that make hormones, like growth hormone, and is karyotypically normal. Epstein-Barr virus episomal vectors (Horlick (1997) *Protein Expr. Purif.* 9:301–308), and plasmid DNA (Lowrie (1997) *Vaccine* 15: 834–838) can also be used to express the mTERT and/or the telomerase enzyme of the invention in vivo or ex vivo. The use of mammalian tissue cell culture to express polypeptides is discussed generally in Winnacker, From Genes to Clones, VCH Publishers, NY, N.Y., 1987)

vii. Optimizing Expression of mTERT and Telomerase Enzyme

In bacterial and other expression systems, codon usage is known to present a potential impediment to high-level gene expression. "Rare" codons, depending on their frequency and context in an mRNA, can have an adverse effect on levels of protein translated therefrom. The problem, if encountered, can be alleviated by modification of the relevant codons or by coexpression of the cognate tRNA genes or by other means (see Kane (1995) Curr. Opin. Biotechnol. 6:494–500). Use of protease-deficient host strains can also increase yields from bacterial expression systems, see Makrides (1996) Microbiol Rev 60:512–538.

One can also optimize levels of expression of mTERT by vector design modifications, such as using exogenous transcriptional regulatory elements. For example, as discussed below, the myeloproliferative sarcoma virus (MPSV) LTR promoter consistently drives higher expression levels in some mammalian cell lines (see Dirks (1994) Gene 149:389–390).

Generally, those of skill in the art recognize that nucleic acids having certain specific sequences can be poorly expressed in one cell and expressed well in other cells. Thus, alternative embodiments of the invention include expression systems that do not incorporate extraneous sequences, i.e., non-coding sequences such as 3' untranslated sequences from a cDNA, with the desired coding sequence. Thus, one optimization method involves removing all extraneous sequences from the coding sequence insert. This method can in some circumstances increase protein expression 5 to 10 fold in bacteria, insect, yeast, mammalian and other cells expression systems.

Gene amplification, whether by higher vector copy number or by replication of a gene in a chromosome, can increase yields of recombinant proteins in mammalian and other cells. One amplification method for heterologous gene expression in mammalian cells is based on the stable transfection of cells with long, linear DNA molecules having several copies of complete expression units coding for the gene of interest linked to one terminal unit coding for a selectable marker. Gene amplification of the gene of interest can be achieved by linking it to a dihydrofolate reductase (Dhfr) gene and administering methotrexate to the transfected cells; this method can increase recombinant protein production many fold (see Monaco (1996) Gene 180:145–150).

vii Use of Cells, Animals and Plants Expressing Recombinant mTERT

The invention provides in vivo assays using transformed cells and transgenic animals expressing recombinant mTERT. These living assay systems can be used to screen for modulators of mTERT; the endogenous TERT, or TERT and TERC, in the non-human cells or animal can be first modified, debilitated, or "knocked out" before reconstituting telomerase activity with mTERT, or, mTERT and mTERC. The reconstitution can be with or without the co-introduction of mTERC or hTERC and/or other telomerase enzyme-associated components. In one embodiment, the invention provides screening assays to identify modulators of mTERT and telomerase enzyme activity in vitro and in vivo, such as in animal and plant cells and whole organisms. The screening assays can utilize mTERT or telomerase enzyme derived by a full or partial reconstitution of telomerase activity, or by an augmentation of existing activity. The assay or screens provided by the invention can be used to test for the ability of telomerase to synthesize telomere DNA or to test for any one or all or of the "partial activities" of mTERT. The assay can incorporate ex vivo modification of cells which have been manipulated to express mTERT with or without an RNA moiety (such as mTERC or hTERC) or associated proteins, and these can be reimplanted into an animal, and so used for in vivo testing.

The invention also provides transformed cells, transgenic animals and methods for expressing mTERT in such animals, as well as otherwise normal cells that can be used to express compositions of interest and can be used in related methods. Such transformed cells and transgenic animals can express the exogenous mTERT either alone or co-expressed with an RNA moiety (i.e., mTERC or hTERC) or other telomerase-associated proteins. The invention provides transgenic animals and recombinant cells to be used, e.g., as bioreactors (Khillan (1997) Methods Mol. Biol. 63:327–342) to produce large amounts of mTERT or telomerase enzyme.

The mTERT-expressing nucleic acid of the invention may be introduced into the genome of an animal or plant host organism by a variety of conventional techniques (Jacenko (1997) Methods Mol. Biol. 62:399–424). For example, recent advances in transgenic and gene-targeting approaches allow a sophisticated manipulation of the mouse genome by gene addition, gene deletion, or gene modifications, making this animal convenient for the methods of the invention (Franz (1997) J. Mol. Med. 75:115–129; Peterson (1997) Genet. Eng. (N.Y.) 19:235–255). Many cloning vectors for transgene construction are known in the art, e.g., Yang (1997) Biotechniques 22:1032–1034. There are two well-established procedures for simple introduction of DNA into animal genomes, pronuclear DNA injection and transduction using a retrovirus (Wei (1997) Annu. Rev. Pharmacol. Toxicol. 37:119–141). Microinjection techniques for use in introducing DNA into animals and plants are known in the art and described in the scientific and patent literature (e.g., Bartoli (1997) Mol. Cell. Biochem. 172:103–109). The introduction of DNA constructs into cells using polyethylene glycol precipitation is described, e.g., in Paszkowski (1984) EMBO J. 3:2717. Electroporation techniques are described, e.g., in Fromm (1985) Proc. Natl. Acad. Sci. USA 82:5824. Ballistic transformation techniques are described, e.g., in Klein (1987) Nature 327:70; Zelenin (1997) FEBS Lett 414:319–322.

The invention also provides transgenic plants and methods for expressing the TERT and telomerase enzyme compositions of the invention and screening assays to identify modulators of telomerase activity in such plants. In plants, the DNA construct may be introduced directly into the genomic DNA of the plant cell using techniques such as electroporation and microinjection of plant cell protoplasts (Schnorf(1991) Transgenic Res. 1:23–30), or the DNA constructs can be introduced directly to plant tissue using ballistic methods, such as DNA particle bombardment (Baum (1997) Plant J. 12:463–469). As discussed above, plant virus vectors such as tobacco mosaic virus containing the telomerase sequences of the invention can be used to inoculate a plant (Rouwendal (1997) Plant Mol Biol 33:989–999).

e. mTERT-deficient "Knockout" Mouse Cells and Animals

In one embodiment, the mTERT nucleic acids and reagents of the invention are used to create mouse cells and animals in which the endogenous mTERT is deleted, modified, supplemented or inhibited. One or several units of the endogenous telomerase enzyme complex, in addition to mTERT, such as mTERC, can also be deleted, modified, supplemented or inhibited. For example, mTERT and mTERC can be deleted, modified or inhibited on either one or both alleles. The cells or animals can be reconstituted with a wild-type or modified mTERT or an exogenous TERT, including for example, a TERT from a non-mouse species, such as hTERT. In TERC knockout cells, a TERC from a non-mouse species, such as hTERC, can be introduced. Other telomerase enzyme complex associated molecules can also be introduced into the knockout cell or animal. Alternative methodologies for constructing knockout cells or animals and methods of screening and selection, are all well known in the art; an illustrative example is set forth below.

Construction of a "knockout" cell and animal is based on the premise that the level of expression of a particular gene in a mammalian cell can be decreased or completely abrogated by introducing into the genome a new DNA sequence (e.g., an mTERT or other nucleic acid construct of the invention) that serves to interrupt some portion of the DNA sequence of the gene to be suppressed. To prevent expression of functional enzyme, simple mutations that either alter the reading frame or disrupt the promoter can be suitable. To upregulate expression, a native promoter can be substituted with a heterologous promoter that induces higher levels of transcription. Also, "gene trap insertion" can be used to disrupt a host gene, and mouse embryonic stem (ES) cells can be used to produce knockout transgenic animals, as described herein and, e.g., in Holzschu (1997) *Transgenic Res* 6: 97–106.

The insertion of the exogenous sequence is typically by homologous recombination between complementary nucleic acid sequences. Thus, the exogenous sequence, which is typically an mTERT nucleic acid in this invention, is some portion of the target (mTERT) gene to be modified, such as exonic, intronic or transcriptional regulatory sequences, or any genomic sequence which is able to affect the level of the target gene's expression; or a combination thereof. The construct can also be introduced into other (i.e., non-mTERT gene) locations in the genome. Gene targeting via homologous recombination in pluripotential embryonic stem cells allows one to modify precisely the gene of interest.

The exogenous sequence is typically inserted in a construct, usually also with a marker gene to aid in the detection of the knockout construct and/or a selection gene. The construct can be any of a variety of expression vectors, plasmids, and the like, as described above. The knockout construct is inserted in a cell, typically an embryonic stem (ES) cell, using a variety of techniques, as described above. The insertion of the exogenous DNA usually occurs by homologous recombination. The resultant transformed cell can be a single gene knockout (i.e., only one of the two copies of the endogenous mTERT has been modified) or a double gene knockout. The knockout construct can be integrated into one or several locations in the cell's genome due to the random nature of homologous recombination events; however, the recombination does occur between regions of sequence complementarity. Typically, less than one to five percent of the ES cells that take up the knockout construct will actually integrate exogenous DNA in these regions of complementarity; thus, identification and selection of cells with the desired phenotype is usually necessary and a selection or marker sequence is usually incorporated into the construct for this purpose. Cells which have incorporated the construct are selected for prior to inserting the genetically manipulated cell into a developing embryo; for example, the cells are subjected to positive selection (using G418, for example, to select for neomycin-resistance) and negative selection (using, for example, FIAU to exclude cells lacking thymidine kinase). A variety of selection and marker techniques are well known in the art, e.g., antibiotic resistance selection or beta-galactosidase marker expression can be used and are further described herein. Alternatively, insertion of the exogenous sequence and levels of expression of the endogenous mTERT or marker/selection genes can be detected by hybridization or amplification techniques or by antibody-based assays, as described herein.

After selection of manipulated cells with the desired phenotype, i.e., complete or partial inability to express mTERT, the cells are inserted into a mouse embryo. Insertion can be accomplished by a variety of techniques, such as microinjection, in which about 10 to 30 cells are collected into a micropipet and injected into embryos that are at the proper stage of development to integrate the ES cell into the developing embryonic blastocyst, at about the eight cell stage, which for mice is about 3.5 days after fertilization. The embryos are obtained by perfusing the uterus of pregnant females. After the ES cell has been introduced into the embryo, it is implanted into the uterus of a pseudopregnant foster mother, which is typically prepared by mating with vascectomized males of the same species. In mice, the optimal time to implant is about two to three days pseudopregnant. Offspring are screened for integration of the mTERT nucleic acid sequences and the modified telomerase activity phenotype. Offspring that have the desired phenotype are crossed to each other to generate a homozygous knockout. If it is unclear whether germline cells of the offspring have modified mTERT, they can be crossed with a parental or other strain and the offspring screened for heterozygosity of the desired trait. The heterozygotes can be crossed with each other to produce mice homozygous for modified mTERT genomic sequence. While the above described methodology describes a typical protocol, any technique can be used to create, screen for, propagate, mTERT knockout mice, e.g., see Bijvoet (1998) *Hum. Mol. Genet.* 7:53–62; Moreadith (1997) *J. Mol. Med.* 75:208–216; Tojo (1995) *Cytotechnology* 19:161–165; Mudgett (1995) *Methods Mol. Biol.* 48:167–184; Longo (1997) *Transgenic Res.* 6:321–328; U.S. Pat. Nos. 5,616,491 (Mak, et al.); 5,464,764; 5,631,153; 5,487,992; 5,627,059; 5,272,071; and, WO 91/09955, WO 93/09222, WO 96/29411, WO 95/31560, and WO 91/12650. Thus, the invention provides for the use of the mTERT reagents of the invention to produce "knockout" mouse cells and animals, and their progeny, in which one or several units of the endogenous telomerase enzyme complex have been deleted, modified or inhibited. These cells and animals can be further reconstituted with wild type or modified endogenous mTERT or exogenous TERT, such as hTERT, or other telomerase enzyme associated components, as described herein.

f. Site-specific Mutations

The invention also provides for an mTERT and telomerase enzyme that have been modified in a site-specific manner to modify or delete any or all functions of the telomerase enzyme or the mTERT protein. Such a modified telomerase provides for means to alter, especially inhibit, telomerase activity in cells and animals and so to control the unlimited proliferative capacity of cells, such as cancer cells. Such telomerases and mTERT proteins can also be employed in the screens of the invention to discover therapeutic agents. For example, the mTERT can be engineered to lose its ability to bind substrate DNA, to bind an RNA moiety (as mTERC or hTERC), to catalyze the addition of telomeric DNA, to bind deoxynucleotide substrate, to have nucleolytic activity, to bind telomere-associated proteins or chromosomal structures, and the like. The resulting "mutant proteins" or "muteins" can be used to identify compounds that specifically modulate one, several, or all functions or activities of the mTERT protein or telomerase enzyme. Site-specific mutations can be introduced into mTERT-encoding nucleic acid by a variety of conventional techniques, well described in the scientific and patent literature. For example, one rapid method to perform site-directed mutagenesis efficiently is the overlap extension polymerase chain reaction (OE-PCR) (Urban (1997) *Nucleic Acids Res.* 25:2227–2228). Other illustrative examples include: Ke (1997) *Nucleic Acids Res* 25:3371–3372, and Chattopadhyay (1997) *Biotechniques* 22:1054–1056, describing PCR-based site-directed mutagenesis "megaprimer" method; Bohnsack (1997) *Mol. Biotechnol.* 7:181–188; Ailenberg (1997) *Biotechniques* 22:624–626, describing site-directed mutagenesis using a PCR-based staggered re-annealing method without restriction enzymes; Nicolas (1997) *Biotechniques* 22:430–434, site-directed mutagenesis using long primer-unique site elimination and exonuclease III.

In another system, a correctly folded, complete protein and its mutagenized encoding mRNA both remain attached to a ribosome and can be assessed for alterations in ligand-binding properties of the native protein. Libraries of native folded proteins with engineered site-specific mutations can now be screened while "evolving" in a cell-free system without the transformation or other constraints imposed when using a host cell (Hanes (1997) *Proc. Natl. Acad. Sci. USA* 94:4937–4942). Modified mTERT proteins of the invention can be produced by site-directed mutagenesis and/or chemical modification methods to introduce unnatural amino acid side chains (see Paetzel (1997) *J. Biol. Chem.* 272:9994–10003 for general methodology).

For example, the invention provides for an mTERT protein that is modified in a site-specific manner and optionally modified to facilitate cloning into bacterial, mammalian, yeast and/or insect expression vectors without any 5' and/or 3' untranslated mTERT sequence, or optionally with altered codon usage produced synthetically. In some circumstances, minimizing the amount of non-protein encoding sequence allows for improved protein production (yield) and/or increase mRNA stability.

As an illustrative example, one can place an additional restriction endonuclease site just upstream (5') to the start (ATG) codon of mTERT cDNA in accordance with the teaching herein. The creation of a restriction site just 5' to the coding region for the protein allows for ready construction of a wide variety of vectors for the production of fusion proteins, including fusion labels and peptides capable of being bound by predefined antibodies (TAGs), i.e., for immuno- or other detection and purification schemes. This modified mTERT provided by the invention can be conveniently used for the construction of expression plasmids of the invention.

2. Detection and Purification of mTERT a. Detection of mTERT and Telomerase Enzyme The invention also provides methods and reagents for detecting or quantitating telomerase enzyme and/or mTERT by a variety of methods. For example, mTERT can be detected and quantified by incorporating functional activity assays of the invention, by immunological assays utilizing a variety of anti-mTERT antibodies provided by the invention, and by nucleic acid-based methodologies, examples of which are also described in detail below.

i. Antibody Production

In one embodiment, the invention provides antibodies that bind one mTERT specie specifically or mTERTs generally, and so can be used to identify and isolate any mTERT species provided for in the invention or to identify a single allele, homologue or isoform of mTERT. Antibodies which can identify any mTERT specie can be generated by using as antigens peptides containing structural features, i.e., motifs, common to all mTERT species, as described herein. In general, the antibodies of the invention can be used to identify, purify, or inhibit any or all activity of murine telomerase enzyme complex and mTERT protein.

Antibodies can act as antagonists of telomerase enzyme activity in a variety of ways, for example, by preventing the telomerase complex or nucleotide from binding to its DNA substrates, by preventing the components of telomerase enzyme from forming an active complex, by maintaining a functional (telomerase enzyme complex) quaternary structure or by binding to one of the enzyme's active sites or other sites that have allosteric effects on activity (the different partial activities of telomerase are described in detail elsewhere in this specification). General methods for producing the antibodies of the invention are described below.

Methods of producing polyclonal and monoclonal antibodies are known to those of skill in the art and described in the scientific and patent literature, see, e.g., Coligan, CURRENT PROTOCOLS IN IMMUNOLOGY, Wiley/Greene, N.Y. (1991); Stites (eds.) BASIC AND CLINICAL IMMUNOLOGY (7th ed.) Lange Medical Publications, Los Altos, Calif., and references cited therein ("Stites"); Goding, MONOCLONAL ANTIBODIES: PRINCIPLES AND PRACTICE (2d ed.) Academic Press, New York, N.Y. (1986); Kohler (1975) *Nature* 256:495; Harlow and Lane (1988) ANTIBODIES, A LABORATORY MANUAL, Cold Spring Harbor Publications, New York. Such techniques include selection of antibodies from libraries of recombinant antibodies displayed in phage ("phage display libraries") or similar on cells. See, Huse (1989) *Science* 246:1275; Ward (1989) *Nature* 341:544; Hoogenboom (1997) *Trends Biotechnol.* 15:62–70; Katz (1997) *Annu. Rev. Biophys. Biomol. Struct.* 26:27–45. Recombinant antibodies can be expressed by transient or stable expression vectors in mammalian cells, as in Norderhaug (1997) *J. Immunol Methods* 204:77–87; or in yeast, Boder (1997) *Nat. Biotechnol.* 15:553–557.

To produce large amounts of antibodies for use in, for example, immunoaffinity purification or diagnostics, a number of immunogens provided by the invention may be used. Telomerase enzyme or mTERT isolated or purified from a natural source (see co-pending U.S. Ser. No. 08/833,377, filed Apr. 4, 1997), from a recombinant protein isolated from transformed cells provided by the present invention, or isolated as a synthetically produced composition, can be used as immunogens for the production of monoclonal or polyclonal antibodies. Naturally occurring murine telomerase enzyme or mTERT proteins or recombinant mTERT and/or telomerase enzyme can be used either in pure or impure form. Synthetic peptides are made using any portion of the mTERT amino acid sequence for use as immunogens, particularly peptides comprising the motif structures described herein. The peptides can be used alone or conjugated to another composition as immunogens.

Methods for the production of polyclonal and monoclonal antibodies are known to those of skill in the art. In brief, an immunogen is mixed with an adjuvant, as described above, and animals are immunized. The animal's immune response to the immunogen preparation is monitored by taking test bleeds and determining the titer of reactivity to the immunogen. When appropriately high titers of antibody to the inununogen are obtained, blood is collected from the animal and antisera prepared. Further fractionation of the antisera to enrich for antibodies reactive to the protein can be done (Harlow and Lane, supra). Various illustrative peptides, proteins and fusion proteins of the invention can be used to generate such polyclonal antibodies.

Large amounts of monoclonal antibodies for use in immunoaffinity purification or immunoassays may be obtained by various techniques familiar to those skilled in the art. Briefly, spleen cells from an immunized animal are immortalized, commonly by fusion with a myeloma cell. Alternative methods of immortalization include transformation with Epstein Barr Virus, oncogenes, or retroviruses, or other methods well known in the art. In the antibody-generating methods of the instant invention, colonies arising from single immortalized cells are screened for production of antibodies of the desired specificity and affinity for murine telomerase enzyme and/or mTERT protein. The yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from appropriate human B cells, ie., immunized according to the general protocol outlined in Huse (1989) *Science*, supra.

The concentration of telomerase enzyme or mTERT protein can be measured by a variety of immunoassay methods of the invention. Generally, immunoassays are described in Stites, supra. The immunoassays of the present invention can be performed in any of several configurations; for background information see ENZYME IMMUNOASSAY, Maggio, ed., CRC Press, Boca Raton, Fla. (1980); Tijssen, Harlow and Lane, supra.

To make the anti-mTERT sera of the invention (e.g., for use in an immunoassay for telomerase) natural, recombinant or synthetic mTERT or telomerase protein preparations, or immunogenic fragments thereof, are produced as described herein. Animals, e.g., inbred strains of mice or rabbits, can be immunized with an mTERT, such as the polypeptide of SEQ ID NO:2, or with isoforms, homologues or immunogenic fragments thereof, alone or using a standard adjuvant, such as Freund's adjuvant, and a standard immunization protocol. Alternatively, a synthetic peptide derived from the sequences disclosed herein and conjugated to a carrier protein can be used an immunogen. Polyclonal sera are collected and titered against the telomerase in an immunoassay, for example, a solid phase immunoassay with the telomerase immobilized on a solid support. Polyclonal antisera with a titer of, e.g., $10^4$ or greater are selected and tested for their cross reactivity against homologous proteins from other organisms and/or non-telomerase protein, using, e.g., a competitive binding immunoassay. Specific monoclonal and polyclonal antibodies and antisera will usually bind with a $K_D$ of at least about 1 $\mu$M, preferably at least about 0.1 $\mu$M or better, and most preferably, 0.01 $\mu$M or less. However, the antisera and monoclonal antibodies of the invention are not limited to these binding affinities.

ii. Immunological Binding Assays

Immunological binding assays (e.g. U.S. Pat. Nos. 4,366,241; 4,376,110; 4,517,288; and 4,837,168) are known in the art. For a review, see also METHODS IN CELL BIOLOGY Vol. 37: Antibodies in *Cell Biology*, Asai, ed. Academic Press, Inc. New York (1993); and Stites, supra. Immunological binding assays (or immunoassays) typically utilize a capture agent to bind specifically to and often immobilize the analyte. The capture agent is a moiety that specifically binds to the analyte. In one embodiment of the present invention, the capture agent is an antibody that specifically binds to telomerase enzyme or mTERT.

Immunoassays also often utilize a labeling agent to specifically bind to and label the binding complex formed by the capture agent and the analyte, as described above. The labeling agent may itself be, for example, one of the moieties comprising the antibody/analyte complex: the labeling agent can be a labeled mTERT or a labeled anti-mTERT antibody. Alternatively, the labeling agent may be a third moiety, such as another antibody, that specifically binds to the antibody-mTERT complex. The labeling agent can be, for example, a second anti-mTERT antibody bearing a label. The second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin. Other proteins capable of specifically binding immunoglobulin constant regions, such as protein a or protein G may also be used as the label agent. These proteins are normal constituents of the cell walls of streptococcal bacteria and exhibit a strong non-immunogenic reactivity with immunoglobulin constant regions from a variety of species (see, generally Akerstrom (1985) *J. Immunol.* 135:2589–2542; Chaubert (1997) *Mod. Pathol.* 10:585–591).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

(1) Non-competitive Assay Formats

Immunoassays for detecting murine telomerase enzyme and mTERT protein may be, for example, either competitive or noncompetitive. Noncompetitive immunoassays are assays in which the amount of captured analyte (as mTERT) is directly measured. In one preferred "sandwich" assay, for example, the capture agent (anti-mTERT antibodies) can be bound directly to a solid substrate where they are immobilized. These immobilized antibodies then capture protein present in the test sample. The mTERT protein thus immobilized is then bound by a labeling agent, such as a second anti-mTERT antibody bearing a label. Alternatively, the second anti-mTERT antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

(2) Competitive Assay Formats

In competitive assays, the amount of analyte (telomerase) present in the sample is measured indirectly by measuring the amount of an added (exogenous) analyte (mTERT) displaced (or competed away) from a capture agent (anti-TERT antibody) by the analyte present in the sample. In one competitive assay, a known amount of, in this case mTERT, usually labeled, is added to the sample, and the sample is then contacted with a capture agent, in this case an antibody that specifically binds mTERT. The amount of labeled mTERT bound to the antibody is inversely proportional to the concentration of mTERT present in the sample. In another embodiment, the antibody is immobilized on a solid substrate. The amount of mTERT bound to the antibody may be determined either by measuring the amount of mTERT present in an mTERT/antibody complex, or alternatively by measuring the amount of remaining uncomplexed mTERT. The amount of mTERT may be detected by providing a labeled mTERT molecule.

A hapten inhibition assay is another competitive assay. In this assay a known analyte, in this case mTERT, is immobilized on a solid substrate, a known amount of anti-mTERT antibody is added to the sample, and the sample is then contacted with the immobilized mTERT. In this case, the amount of anti-mTERT antibody bound to the immobilized mTERT is inversely proportional to the amount of telomerase or mTERT present in the sample. The amount of immobilized antibody is determined by detecting either the immobilized fraction of antibody or the fraction of the antibody that remains in solution. Detection may be direct where the antibody is labeled or indirect by the subsequent addition of a labeled moiety that specifically binds to the antibody, as described above.

Immunoassays in the competitive binding format can be used for crossreactivity determinations to permit one of skill to determine if a protein or enzyme complex is an mTERT or murine telomerase enzyme. For example, an mTERT of SEQ ID NO:2 can be immobilized to a solid support, a putative mTERT protein is added to the assay to compete with the binding of the anti-mTERT sera to an immobilized mTERT. The ability of the protein to compete with the binding of the antisera to the immobilized mTERT is compared to the ability of soluble mTERT (same as on the solid support) to compete with the binding of the antisera to the immobilized mTERT.

(3) Other Assay Formats

The present invention also provides methods for Western blot (inmmunoblot) analysis to detect and/or quantify the presence of mTERT or telomerase enzyme protein in a sample. The technique generally comprises separating sample proteins by gel electrophoresis on the basis of molecular weight, transferring the separated proteins to a suitable solid support (such as a nitrocellulose filter, a nylon filter, or derivatized nylon filter) and incubating the sample with antibodies that specifically bind mTERT. The anti-mTERT antibodies specifically bind to mTERT on the solid support. These antibodies may be directly labeled or alternatively may be subsequently detected using a second labeled antibody that specifically binds to the anti-mTERT antibody.

Antibodies can also be used to probe expression libraries, see Young (1982) *Proc. Natl. Acad Sci. USA* 80:1194. In general, a cDNA expression library may be prepared from commercially available kits or using readily available components. Phage (Hurst (1997) *Methods Mol Biol* 69:155–159), bacteria (Davis (1997) *Proc. Natl. Acad. Sci. USA* 94:2128–2132), insect cells (Granziero (1997) *J. Immunol. Methods* 203:131–139), yeast, and animal cells (*Xenopus oocytes*) can be used. One selects mRNA from a source that is optionally enriched with the target mRNA or in which the protein is abundant and creates cDNA which is then ligated into a vector, and the vector is transformed into the library host cells for immunoscreening. Screening involves binding and identification of antibodies bound to specific proteins on cells or immobilized on a solid support such as nitrocellulose or nylon membranes. Positive clones are selected for purification to homogeneity and the isolated cDNA then prepared for expression in the desired host cells. See also METHODS OF CELL BIOLOGY, VOL. 37, *Antibodies in Cell Biology*, Assai (ed.) 1993.

The methods of the invention are also compatible with other assay formats, including liposome immunoassays (LIA) (Rongen (1997) *J. Immunol. Methods* 204:105–133), in which liposomes designed to bind specific molecules (e.g., antibodies) and release encapsulated reagents or markers are employed. The released chemicals can be detected using standard techniques (see, e.g. Monroe (1986) *Amer. Clin. Prod. Rev.* 5:34).

b. Purification and Isolation of mTERT and Telomerase Enzyme

The methods and reagents of the invention enable one to isolate and purify the naturally occurring and recombinantly expressed murine telomerase enzyme and mTERT protein of the invention from a variety of sources, such as larval homogenates, bacterial cells, yeast, mammalian cells, human cells, tissue culture media, transgenic plants and animals, to substantial purity. For general information relating to standard purification procedures, including selective precipitation with such substances as ammonium sulfate; column chromatography, immunopurification methods, and others see, for instance, Scopes, R. K., Protein Purification: Principles and Practice, 2nd ed., Springer Verlag, (1987), U.S. Pat. No. 4,673,641, Ausubel, and Sambrook. The purification of TERT polypeptides is described herein and in related applications. The purification of telomerase enzyme from a natural source is also described in co-pending U.S. Ser. No. 08/833,377, filed Apr. 4, 1997. The present invention also provides improvements to such methods relating to antibodies against mTERT for purification, as well as fusion proteins comprising a mTERT protein and a label that aids purification.

i. Isolation of mTERT from Bacterial Cultures

The present invention provides secreted recombinant mTERT proteins which can isolated from the broth in which bacterial or eukaryote cells have been cultured. In one embodiment, the mTERT-encoding nucleic acids of the invention can be expressed as a fusion protein with maltose-binding protein (MBP) or other proteins or peptides fused thereto to increase the amount of secreted and soluble product (see Chames (1997) *FEBS Lett.* 405:224–228); Sagiya (1994) *Appl. Microbio.l Biotechnol.* 42:358–363).

ii. Purification of mTERT from Bacterial Cells

When recombinant mTERT protein is expressed in bacteria, such as *E. coli*, the protein may be exported into the periplasm of the bacteria. The periplasmic fraction of the bacteria can be isolated by cold osmotic shock or by other methods known to skill in the art; see Ausubel (1970) *J. Biol. Chem.* 245:4842; Blight (1994) *Curr. Opin. Biotechnol.* 5:468–474. For example, to isolate proteins from the periplasm, the cells are centrifuged to form a pellet. The pellet can be resuspended in a buffer containing, for example, 20% sucrose. To lyse the cells, cells can be treated as described below. The suspension can be centrifuged and the supernatant decanted and saved. The proteins present in the supernatant can be separated and purified as described herein.

iii. Purification of mTERT from Inclusion Bodies

When recombinant mTERT and other telomerase enzyme proteins are expressed by transformed bacteria or other cells in large amounts, the proteins can form insoluble aggregates. Purification of aggregate proteins, i.e., inclusion bodies, typically involves extraction, separation and purification by disruption of the cells, typically but not limited by, incubation in a buffer of about 100–150 $\mu$g/mL lysozyme and 0.1% NONIDET P40 a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel and Sambrook and will be apparent to those of skill in the art.

The cell suspension is centrifuged and the pellet containing the inclusion bodies resuspended in buffer, e.g., 20 mM Tris-HCl (pH 7.2), 1 mM EDTA, 150 mM NaCl and 2% TRITON-X 100, a non-ionic detergent. The wash step may be repeated to remove more cellular debris. The remaining pellet of inclusion bodies may be resuspended in an appropriate buffer (e.g., 20 mM sodium phosphate, pH 6.8, 150 mM NaCl). Other appropriate buffers will be apparent to those of skill in the art. Following the washing step, the inclusion bodies can be solubilized by the addition of a solvent that is both a strong hydrogen acceptor and a strong hydrogen donor (or a combination of solvents each having one of these properties) together with a reducing agent such as DTT. The proteins that formed the inclusion bodies can then be renatured by dilution or dialysis with a compatible buffer. Suitable solvents include, but are not limited to, urea (typically from about 4 M to about 8 M), formamide (typically at least about 80%, volume/volume basis), and guanidine hydrochloride (typically from about 4 M to about 8 M). Some solvents capable of solubilizing aggregate-forming proteins include, e.g., SDS (sodium dodecyl sulfate), 70% formic acid, but may be inappropriate if irreversible denaturation of the proteins occurs, which is typically accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. The protein can be separated during or after solubilization from other bacterial or other contaminating host proteins by standard separation techniques using the reagents of the invention in accordance with the methods of the invention.

iv. Standard Protein Separation Techniques

The present invention can provides methods for purifying telomerase enzyme and mTERT from a natural source or as a recombinant protein from transformed cells or transgenic animals. The novel reagents of the invention, such as the anti-mTERT antibodies, can be used to improve purification procedures, such as those described in co-pending U.S. Ser. No. 08/833,377, filed Apr. 4, 1997. Some illustrative examples of methods for purifying murine telomerase enzyme, mTERT, and other compositions used in the methods of the invention are described below.

(1) Solubility Fractionation

If the protein mixture is complex, an initial salt fractionation can separate many of the unwanted host cell proteins (or proteins derived from the cell culture media) from the protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations, a typical protocol is to add saturated ammonium sulfate to a protein solution so that the resultant ammonium sulfate concentration is between 20–30%. This will precipitate the most hydrophobic of proteins. The precipitate is discarded (unless the protein of interest is hydrophobic), and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

(2) Size Differential Filtration

If the size of the protein of interest is known or can be estimated from the cDNA sequence, proteins of greater and lesser size can be removed by ultrafiltration through membranes of different pore size (e.g., Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The protein will pass through the membrane into the filtrate. The filtrate can then be chromatographed.

(3) Column Chromatography

Proteins can be separated on the basis of their size, net surface charge, hydrophobicity and affinity for ligands. In addition, antibodies raised against proteins can be conjugated to column matrices and the proteins immunopurified. All of these general methods are well known in the art. See Scopes (1987) supra. Chromatographic techniques can be performed at any scale and using equipment from many different manufacturers (e.g., Pharmacia Biotech). Protein concentrations can be determined using any technique, e.g., as in Bradford (1976) Anal. Biochem. 72:248–257.

v. Isolation of mTERT and Murine Telomerase Enzyme

Telomerase can be isolated and purified by any of a variety of means provided by the invention, as described above. In one embodiment of the invention, telomerase enzyme can be purified to over 60,000-fold purity over cytoplasmic crude cell preparations. The steps to be included in a purification method depend on the level of purification one desires. An illustrative method to purify telomerase enzyme or mTERT protein from an impure composition containing organic biomolecules to at least 60,000-fold compared to crude extract (about 4% relative purity) can involve, e.g., (1) contacting the mTERT with a first matrix that binds molecules bearing a negative charge, for example, POROS 50 HQ, separating mTERT from other organic biomolecules that do not bind to the matrix and collecting the mTERT; (2) contacting the mTERT with a matrix that binds molecules bearing a positive charge, for example POROS Heparin 20 HE-1, and separating mTERT from other organic biomolecules that do not bind to the matrix and collecting the mTERT; (3) contacting the mTERT with a second matrix that binds molecules bearing a negative charge, e.g., SOURCE 15Q, separating mTERT from other organic biomolecules that do not bind to the matrix and collecting the mTERT; (4) contacting the mTERT with an affinity agent having specific affinity for mTERT, e.g., an oligonucleotide complementary to the telomerase enzyme's RNA moiety or an anti-mTERT antibody, separating mTERT from other organic biomolecules that do not bind to the affinity agent and collecting the mTERT; and/or (5) separating the mTERT from other organic biomolecules according to molecular size, shape, or buoyant density, e.g., separating molecules according to size on a TosoHaas TSK-gel*G5000PW$_{XL}$ sizing column and collecting the mTERT. The isolation and purification protocol also can include the step of contacting the mTERT with an intermediate-selectivity matrix, separating mTERT from other organic biomolecules that do not bind to the intermediate-selectivity matrix and collecting the mTERT, preferably before the affinity step. mTERT can be isolated to different levels of purity by altering, changing the sequence of, or eliminating any of the steps in the purification protocol. However, any preferred protocol will typically include contacting the mTERT with an affinity agent, such as the antibodies of the invention. Contacting the mTERT with at least one matrix that binds molecules bearing a negative charge or a positive charge is the next preferred step or steps to include in the protocol.

c. Amino Acid Sequence Determination

Illustrative amino acid sequences of mTERT of this invention can be determined by, for example, Edman degradation, a technique which is well known in the art. In addition to the internal sequencing (see also Hwang (1996) *J. Chromatogr. B. Biomed. Appl.* 686:165–175), N-terminal sequencing can be performed by techniques known in the art. For C-terminal sequence determination, a chemical procedure for the degradation of peptides and analysis by matrix-assisted-laser-desorption ionization mass spectrometry (MALDI-MS) can be used, see, e.g., Thiede (1997) *Eur. J. Biochem.* 244:750–754.

d. Molecular Weight/Isoelectric Point Determination

The molecular weight of a protein can be determined by many different methods, all known to one of skill in the art. Some methods of determination include: SDS gel electrophoresis, native gel electrophoresis, molecular exclusion chromatography, zonal centrifugation, mass spectroscopy, and calculation from sequencing. Disparity between results of different techniques can be due to factors inherent in the technique. For example, native gel electrophoresis, molecular exclusion chromatography and zonal centrifugation depend on the size of the protein. The proteins that are cysteine rich can form many disulfide bonds, both intra- and intermolecular. Mobility under SDS gel electrophoresis conditions depends on the binding of SDS to amino acids present in the protein. Some amino acids bind SDS more tightly than others, therefore, proteins will migrate differently depending on their amino acid composition. Mass spectroscopy and calculated molecular weight from the sequence in part depend upon the frequency that particular amino acids are present in the protein and the molecular weight of the particular amino acid. If a protein is glycosylated, mass spectroscopy results will reflect the glycosylation but a calculated molecular weight may not.

The calculated molecular weight of mTERT (SEQ ID NO:2), with a calculated length of 1122amino acids, is estimated to be about 127 kD (specifically, 127,979 kD); and its apparent molecular weight by SDS gel electrophoresis is estimated to be between about 115 kD to about 140 kD. However, additional mTERT proteins, mTERT isoforms, alleles and homologues within the scope of the invention are not limited to this molecular weight range.

The isoelectric point of a protein can be determined by native gel (or disc) electrophoresis, isoelectric focussing or, in a preferred method, by calculation given the amino acid content of the protein (see, e.g., Wehr (1996) *Methods Enzymol.* 270:358–374; Moorhouse (1995) *J. Chromatogr. a.* 717:61–69, describing capillary isoelectric focusing). The isoelectric point (pI) of mTERT (SEQ ID NO:2) has been calculated to be about 10.4. However, mTERT alleles, isoforms and homologues, within the scope of the invention are not limited to this range of isoelectric points.

e. mTERT Fusion Proteins

The mTERT of the invention can also be expressed as a recombinant protein with one or more additional polypeptide domains linked thereto to facilitate protein detection, purification, or other applications. Such detection- and purification-facilitating domains include, but are not limited to, metal chelating peptides such as polyhistidine tracts and histidine-tryptophan modules that allow purification on immobilized metals, protein a domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and telomerase or telomerase-associated protein(s) may be useful to facilitate purification. One such expression vector provides for expression of a fusion protein comprising the sequence encoding an mTERT of the invention and nucleic acid sequence encoding six histidine residues followed by thioredoxin and an enterokinase cleavage site (e.g., see Williams (1995) *Biochemistry* 34:1787–1797). The histidine residues facilitate detection and purification while the enterokinase cleavage site provides a means for purifying the desired protein(s) from the remainder of the fusion protein. Technology pertaining to vectors encoding fusion proteins and applications of fusion proteins are well described in the patent and scientific literature, see e.g., Kroll (1993) *DNA Cell. Biol.*, 12:441–53.

3. Assaying for Telomerase Activity

The assays described below can be used to detect, assess the purity of and quantify isolated or recombinant mTERT produced in bacteria, insect and yeast, tissue culture fluid and plant and animal tissues, or other, including natural, sources. The activity assays described below and provided by the present invention can be used to identify compositions which modulate mTERT, i.e., modify, activate or inhibit, the activity of telomerase, ie., act as antagonists or agonists of telomerase-mediated DNA replication.

a. Measuring an Increase or Decrease in the Length of Telomeres

Because telomerase enzyme extends telomerase DNA, and because telomeres shorten as cells divide in the absence of telomerase, one can indirectly detect mTERT or telomerase enzyme by measuring telomere length. Assays well known in the art that can be used to determine the length of telomeres include restriction endonuclease digestion and probing as well as a modified Maxam-Gilbert reaction, see e.g., WO 93/23572; WO 95/13382; WO 96/41016; U.S. Pat. Nos. 5,645,986; 5,707,795; and 5,686,245.

Direct fluorescence in situ by fluorochrome-labeled nucleic acid probes enables determination of the presence and location of DNA sequences complementary to the labeled probe. Without further amplification, this method can be limited to detecting targets with middle to high copy numbers. However, both signal and target amplification is possible, for example, with labeled antibody (as a fluorochrome) specific for a label which is covalently attached to the nucleic acid probe, as discussed above; also, see Schwarzacher (1994) "Direct fluorochrome-labeled DNA probes for direct fluorescent in situ hybridization to chromosomes" *Methods Mol. Biol.* 28:167–176.

In one embodiment of the invention, telomerase enzyme-generated products or telomeric structures are detected using a variation of an antibody amplification technique, the so-called catalyzed signal amplification (CSA) technique. This immunohistochemical assay allows in situ visualization of the telomere (or any composition) of interest. In one variation, incubation with primary antibody is followed by secondary antibody conjugated to biotin, followed by a strepavidin-biotin-peroxidase complex, biotinyl-tyramide reagent and 3,3'-diaminobenzidine tetrahydrochloride (see Sanno (1996) *Am. J. Clin. Pathol.* 106:16–21; Sanno (1997) *Neuroendocrinology* 65:299–306).

b. In Vitro Telomerase Activity Assays

In one embodiment, the mTERT protein of the invention is used to reconstitute telomerase activity. Such reconstitution is useful not only for detecting modulators of telomerase-mediated DNA replication in in vitro activity assays, but also for identifying mTERT polypeptides and telomerase enzymes, including mTERT isoforms, alleles and homologues.

i. Detecting Telomerase Activity Using Immobilized Enzyme

In one embodiment of the invention, telomerase activity is monitored in a solid-phase system using the so-called catalyzed reporter deposition (CARD) system. Telomerase enzyme or mTERT is immobilized onto a solid phase using the antibodies of the invention or chemical linkers, and the like. To assay fill or a "partial" mTERT or telomerase enzyme activity, a telomerase enzymatic reaction is carried out in a buffered aqueous solution compatible with the assayed telomerase activity. The appropriate reagents are added to detect the activity, for example, to allow the telomerase to catalyze multiple copies of detectable, reaction product. For general information, see Bobrow (1992) "The use of catalyzed reporter deposition as a means of signal amplification in a variety of formats" *J. Immunol. Methods* 150:145–149; and Schmidt (1997) "Signal amplification in the detection of single-copy DNA and RNA by enzyme-catalyzed deposition (CARD) of the novel fluorescent reporter substrate Cy3.29-tyramide" *J. Histochem. Cytochem*. 45:365–373.

c. Incorporation of Labeled Nucleotides—Primer Extension

One method which assays for telomerase activity in cell samples relies on the incorporation of radioactively or otherwise labeled nucleotides into newly synthesized polynucleotides by elongation of a telomerase substrate, i.e., the telomerase extension product. Briefly, this assay measures the amount of nucleotides incorporated into polynucleotides synthesized on a primer sequence. The amount incorporated is typically measured as a function of the intensity of a band on a phosphor screen, such as the PhosphorImager® or FluorImager® (Molecular Dynamics, Sunnyvale, Calif.) exposed to a gel on which the radioactive products are separated. See Morin (1989) *Cell* 59:521–529.

Conventional "primer extension" assays use an oligonucleotide substrate, a radioactive deoxyribonucleotide triphosphate (dNTP) for labeling the extended substrate, and gel electrophoresis for resolution and display of telomerase extension products. Because telomerase stalls and can release the DNA after adding the first G in the 5'-TTAGGG-3' (SEQ ID NO:7) telomeric repeat, the characteristic pattern of products detected on the gel is a six nucleotide ladder of extended oligonucleotide substrates. The phase of the repeat depends on the 3' end sequence of the substrate; telomerase recognizes where the end is in the repeat and synthesizes accordingly to yield contiguous, repetitive sequences. As noted above, the nucleotides, substrate, and extended substrate can be alternatively labeled with non-radioactive means such as fluorescent, phosphorescent, or chemiluminescent labels. The nucleotides or extended substrate can be "tagged," where the "tag" can be identified by a second labeled molecule. For example, the tag can be biotin. The resultant tagged nucleotide can be recognized by using a labeled avidin, such as avidinylated horseradish peroxidase, followed by a chromogenic substrate, as, e.g., in Durrant (1996) *Mol. Biotechnol*. 6:65–67. Many variations on these detection formats are well known in the art.

i. Dot Blot Assay

Another assay for telomerase activity is the dot blot assay. The dot blot assay is useful for routine screening because it can be used in high throughput mode, and hundreds of assays can be carried out in a single day with a good portion of the labor performed automatically. The dot blot assay is most effective for comparing activity of samples at roughly the same level of purity and is less effective for a multiplicity of samples at different stages of purity, and so may not be a preferred assay for determining relative purity. See co-pending U.S. Ser. No. 08/833,377, filed Apr. 4, 1997.

ii. Reverse Transcription PCR/Quantitative PCR

The present invention provides polymerase chain reaction (PCR) assays that can be used to detect and quantify levels of telomerase enzyme-generated product. See also, U.S. Pat. No. 5,629,154. Other target amplification techniques can also be employed in these methods, and one of skill in the art will appreciate that, whatever amplification method is used, if a quantitative result is desired, care must be taken to use a method that maintains or controls for the relative amplification of the various nucleic acids amplified. PCR is discussed in general above, a comprehensive discussion on quantitative PCR can be found in the scientific and patent literature, and is, for example, outlined in Innis, supra; see also Okamoto (1997) *Biol. Pharm. Bull*. 20:1013–1016.

iii. Telomeric Repeat Amplification Protocol (TRAP Assay)

The invention also provides for novel embodiments of the TRAP assay and variations of this well known telomerase activity assay. The present invention provides reagents useful for the TRAP assay as well as new amplification based telomerase activity assays for a wide variety of applications.

One limitation of the primer extension assay, described above, for assessing telomerase activity is weak signal strength, often necessitating long (7 or more days) autoradiographic exposure. Fortunately, the highly sensitive PCR-based "TRAP" assay for measuring telomerase activity has been developed. The TRAP assay is an amplification-based method for detecting, determining, and measuring telomerase activity and is described in PCT Publication Nos. WO 97/15687 and WO 95/13381 and U.S. Pat. No. 5,629,154; see also U.S. Ser. No. 08/632,662, and U.S. Ser. No. 08/631,554, filed 15 Apr. 1996 and 12 Apr. 1996, respectively. See also, Kim (1994) *Science* 266:2011; PCT/US96/09669; Piatyszek (1995) *Methods in Cell Science* 17:1–15; Krupp (1997) *Nuc. Acids Res*. 25:919–921; Kim (1994) *Science* 266:2011–2015; Wright (1995) *Nucleic Acids Res*. 23:3794–3795; Tatematsu (1996) *Oncogene* 13:2265–2274; and Kim (1997) *Nuc. Acids Res*. 25:2595–2597.

The TRAP assay allows one to measure the elongation of a short oligonucleotide primer known to act as an efficient substrate of telomerase enzyme. Telomerase is an RNA-dependent DNA polymerase that normally synthesizes telomeric repeats at the 3' end of the leading DNA strand. mTERC and hTERC can function as templates for the extension of a chromosomal end. hTERT synthesizes telomeric repeats (TTAGGG)n (SEQ ID NO:7) onto the 3' end of a telomerase substrate oligonucleotide ("TS"), 5'-AATCCGTCGAGCAGAGTT-3' (SEQ ID NO:6). Although the TS sequence lacks TTAGGG (SEQ ID NO:7) repeats, it is a good human telomerase enzyme substrate (first described in Morin, (1991) *Nature* 353:454–456). The TS substrate lacks TTAGGG repeats, allowing for forward PCR amplification primers specific for extended TS. The forward, or other primer of the primer pair anneals only to the TTAGG (SEQ ID NO:7) repeats added by the telomerase to TS, and that primer pair enables efficient amplification of the extended TS. mTERT activity can be assayed using this TRAP model, as demonstrated in the Example, below.

For use of internal controls in TRAP assays, see the publications cited supra and, e.g., Yashima (1997) "Telomerase activity and in situ telomerase RNA expression in malignant and non-malignant lymph nodes" *J. Clin Pathol* 50:110–117.

iv. Reconstitution of Activity In Vitro

In one embodiment of the invention, using mTERT encoding nucleic acid, telomerase enzyme activity, full or "partial," is reconstituted in vitro in an appropriate in vitro translation or transcription/translation system, many of which are commercially available, e.g., RiboMAX™ Large Scale RNA Production System, Flexi Rabbit Reticulocyte Lysate System, Promega Corp., Madison, Wis. In alternative embodiments, the RNA component of the mTERT-containing telomerase enzyme complex can be mTERC or hTERC: Other telomerase-associated proteins can also be co-expressed in the system.

d. In Vivo/In Situ Telomerase Activity Assays—Reconstitution of Activity

The present invention provides methods for identifying modulators of mTERT-containing telomerase enzyme-mediated DNA replication by in vitro, in vivo and in situ activity assays. Methods for identifying modulators of telomerase activity have been described. See, e.g., U.S. Pat. No. 5,645,986; and Ser. No. 08/288,501, filed Aug. 10, 1994. The present invention provides improvements to these known methods by providing highly purified murine telomerase enzyme, mTERT, as well as anti-mTERT antibodies for use as controls or agents. The present invention also provides activity assays that can identify modulators of full or a partial activity of mTERT or telomerase enzyme.

In certain embodiments, assay formats are chosen that detect the presence, absence or abundance of either a telomerase enzyme or mTERT protein, a telomerase- or mTERT-generated product, an mTERT isoform, allele, or homologue, in each cell in a sample or in a representative sampling. Examples of such formats include those that detect a signal by histology, e.g., immunohistochemistry, and with nucleic acids, either including signal-enhancing steps, such as in situ nucleic acid amplification followed by fluorescence-activated cell sorting (FACS-PCR). These formats are particularly advantageous when dealing with a highly heterogeneous cell population, e.g., containing multiple cell types from among which only one or a few types have elevated mTERT levels.

In vivo assays include non-human cell systems into which recombinant mTERT is expressed. The RNA moieties mTERC or hTERC can either be simultaneously co-expressed with mTERT or hTERT to generate telomerase enzyme activity. Other murine telomerase-associated proteins can also be co-expressed in this in vivo assay system. This reconstitution of full or "partial" telomerase activity using mTERT in vivo provides for a method of screening for telomerase modulators in cells or animals from any origin. Telomere length can also be measured, as described above.

Telomerase enzyme antagonists that can cause or accelerate loss of telomeric structure can be identified by monitoring and measuring their effect on mTERT or telomerase enzyme activity in vivo, ex vivo, or in vitro, or by their effects on telomeric length (as through staining or use of tagged hybridization probes) or, simply, through cell death of telomerase positive cancer cells (critical shortening of telomeres leads to a phenomenon termed "crisis" or M2 senescence (Shay (1991) Biochem. Biophys. Acta 1072:1–7), which cancer cells can bypass by activating telomerase or another telomere length maintenance pathway but which otherwise will lead to their death through chromosomal deletion and rearrangement).

The present invention also provides assays that can also be used to screen for agents that increase the full or a "partial" activity of telomerase, either by causing TERT protein or telomerase to be expressed in a cell in which it normally is not expressed or by increasing telomerase activity levels in telomerase positive cells. Such agonists can be identified in an activity assay of the invention or by their effect on telomere length or both.

i. Administering Telomerase-activity-modulators to Mortal Cells

In one embodiment, the invention provides recombinant mTERT and mTERT-containing telomerase enzyme and necessary telomerase enzyme complex components for expression in normal, diploid mortal cells to create indefinitely proliferating cells, to immortalize those cells, or to increase their proliferative capacity. For example, expression of mTERT of the invention can be used to create immortal or indefinitely proliferating B lymphocytes. In another embodiment, mortal cells that produce a commercially desirable protein, such as pituitary cells, are immortalized or made indefinitely proliferating by expression of an mTERT, e.g., as that of SEQ ID NO:2.

In another embodiment, the invention provides means to inhibit the expression or activity of telomerase enzyme in a cell to be used for transplantation into a host so that the transplanted cell cannot become immortalized or indefinitely proliferating. This method is ideal for cells that have been modified to delete histocompatibility antigens or modified in some way to prevent or decrease the possibility of immune rejection, because such cells are preferred for transplantation. Reintroduction of normal cells into an individual presents a risk that the cells may change to a state of uncontrolled cell growth, becoming a malignancy. The present invention prevents this complication by "knocking out" or inhibiting (antagonizing) telomerase activity (or a telomerase enzyme complex component necessary for activity). Without an active telomerase, the cells are "irreversibly mortal," decreasing the probability of malignant transformation after reintroduction.

When reconstituting telomerase activity in mortal cells, in which telomerase activity normally cannot be detected, generation of a maximum level of telomerase activity may necessitate co-expression of mTERT with other components, especially such as mTERC, and in some cases, other telomerase-associated proteins.

ii. Administering Telomerase-activity-modulators to Immortal Cells

Antagonists of telomerase-mediated DNA replication can be identified by administering the putative inhibitory composition to a cell that is known to exhibit significant amounts of telomerase activity, such as cancer cells or indefinitely proliferating cells. Such compositions so identified can then be used to treat diseases, such as cancer, that are exacerbated by or caused by or depend on a minimum level of telomerase expression or activity. Telomerase enzyme-positive cells can be tumor cell lines, isolated from in vivo sources, or present in an intact animal, as for example, in a solid tumor. Reconstitution of activity by the methods and with the reagents of the invention in an in vitro system, cell or animal using mTERT, mTERC, and/or other telomerase-associated components, allows one to screen for antagonists by assaying or monitoring the expected decrease in telomerase activity, or accelerated loss of telomeric length, or senescence (cancer cells that continue to divide despite critical telomere shortening die in the absence of telomerase activity).

iii. Transgenic Animals Incorporating mTERT Genes

The introduction of mTERT or other TERT genes into mice to create transgenic mice can be used to assess the consequences of mutations or deletions to the coding or transcriptional regulatory (e.g., promoter) regions. In one embodiment, the endogenous mTERT gene in these mice is still functional and wild-type (native) telomerase activity can still exist. With the use of a promoter that drives high level expression of the exogenous TERT construct, the endogenously produced mTERT protein can be competitively replaced with the introduced, exogenous TERT protein. This transgenic animal (retaining a functional endogenous telomerase activity) is preferred in situations where it is desirable to retain "normal," endogenous telomerase function and telomere structure.

In other situations, where it is desirable that all telomerase activity is by the introduced exogenous TERT protein, use of an mTERT knockout line (described below) is preferred.

Promoter function, and in a preferred embodiment, mTERT promoter function, can be assessed with mTERT transgenic animals. Alterations of mTERT promoters can be constructed that drive mTERT or a reporter gene to assess their function and expression pattern and characteristics (the invention also provides constructs and methods for gene expression driven by an mTERT promoter by transient transfection). In one embodiment, the ability of an mTERT promoter to limit the expression of a cell killing gene (e.g., thymidine kinase or ricin) to cancer cells can be assessed. The genomic regions that confer developmental and tissue specific expression can be identified. This could lead to the identification of proteins or other transcriptional transactivators that modulate gene, e.g., mTERT, expression. Proteins that modulate mTERT expression are attractive targets for therapeutic intervention either for inhibition of telomerase activity in cancer cells or for the extension of replicative lifespan in normal cells and other uses as described herein.

Transgenic animal or cells expressing mTERT proteins in an inappropriate manner can also be constructed. Promoters can be used that give constitutive expression in all tissues or developmental stages or limit expression to specific cell types or tissues. In this manner the biological consequences of an mTERT native or altered protein can be assessed in vivo or ex vivo.

Transgenic animals or cells expressing mutant (i.e., non-native) mTERT proteins can also be constructed. This will provide an in vivo or ex vivo model system to assess the structure and function of mTERT amino acid sequences on telomerase or telomere function.

iii. Telomerase Knockout Cells and Animal Models

The invention also includes "knockout" cells and animals, in which one or several units of the endogenous telomerase enzyme complex have been deleted, altered, or inhibited. These "knockout" cells and animals can serve as a model useful in drug discovery and development, and include modified cells or animals with increased amounts of endogenous, modified endogenous or exogenous telomerase enzyme activity. Reconstitution of telomerase activity can save the cell or animal from the inevitable cell death caused by inability to maintain telomeres.

Methods of altering the expression of endogenous genes are well known to those of skill in the art. Typically, such methods involve altering or replacing all or a portion of the regulatory sequences controlling expression of the particular gene to be regulated The regulatory sequences, e.g., the native promoter can be altered. One technique for targeted mutation of genes involves placing a genomic DNA fragment containing the gene of interest into a construct, i.e., a vector. An example of such a vector includes the cloning of two genomic regions flanking the gene of interest around a selectable neomycin-resistance cassette in a vector containing a thymidine kinase gene. See also Westphal (1997) *Curr.* *Biol.* 7:530–533. This "knock-out" construct is then transfected into the appropriate host cell, ie., a mouse embryonic stem (ES) cell, as discussed in detail above.

e. Quantitation of Telomerase Activity

Telomerase enzyme activity can be quantified in a variety of ways, depending on the method of measurement and convenience. Telomerase activity can be expressed in terms of the amount of mTERT, telomerase enzyme or telomerase-generated product in a sample, which can be expressed as standard units of weight per quantity of biological sample (e.g., picograms per gram tissue, picograms per number of cells, etc.), as a number of molecules per quantity of biological sample (e.g., molecules/cell, moles/cell, etc.) or some similar method, or may be expressed using arbitrary units (e.g., comparing a normal cells from an individual to indefinitely proliferating or immortal, cancer cells). The quantity of mTERT, telomerase enzyme or telomerase-generated product can also be expressed in relation to the quantity of another molecule, ie., the number of mTERT molecules (of gene, protein or mRNA transcript) per sample per number of 28S rRNA transcripts in sample; nanograms of mTERT protein per nanograms of actin, and the like.

When measuring mTERT, telomerase or telomerase-generated product in two (or more) different samples, it will sometimes be useful to have a common basis of comparison of the two samples. When comparing a sample of normal tissue and a sample of cancerous tissue, equal amounts of tissue (by weight, volume, number of cells, etc.) can be compared. Alternatively, equivalents of a marker molecule (e.g., 28S rRNA, mTERC, actin) may be used. For example, the amount of telomerase or telomerase-generated product in a healthy tissue sample containing 10 picograms of 28S rRNA can be compared to a sample of tissue containing the same amount of 28S rRNA.

In certain embodiments, assay formats are chosen that detect the abundance of an mTERT isoform, allele or homologue in each cell in a sample in situ. Examples of such formats include those that detect the intensity of a signal by immuno-histochemistry with nucleic acid signal-enhancing steps, such as in situ nucleic acid amplification followed by fluorescence-activated cell sorting (FACS-PCR). These formats are particularly advantageous when dealing with a highly heterogeneous cell population, e.g., containing multiple cells types or which only one or a few types have elevated mTERT levels. General methodology related to this technique is described in Cao (1995) "Identification of malignant cells in multiple myeloma bone marrow with immunoglobulin VH gene probes by fluorescent in situ hybridization and flow cytometry" *J. Clin. Invest.* 95:964–972.

It is not always necessary to quantify mTERT mRNA or protein or to detect a full or partial telomerase enzyme activity. Often the detection of an mTERT gene product will be sufficient for a diagnosis, as under assay conditions in which the telomerase activity or telomerase-generated product is not detectable in control, e.g., nonmalignant, normal cells. As another example, when the levels of product found in a test (e.g., tumor) and control (e.g., mortal cell) samples are directly compared, quantitation of mTERT is not necessary to make an accurate determination.

i. Quantitating Amounts of Nucleic Acid in a Sample to Determine Telomerase Activity: Methodologies Telomerase enzyme activity can be expressed in terms of the amount of telomerase-generated product in a sample, i.e., the amount of telomere DNA synthesized by the enzyme complex. Quantitation of RNA is also useful for determining the transcriptional efficiency of recombinant DNA in expression systems, such as with in vitro transcription, antisense RNA expression, transfection of mortal, indefinitely proliferating or immortal cells and transgenic animals. Evaluating levels of RNA is also useful in evaluating cis- or trans-transcriptional regulators.

General techniques for quantitating amount of nucleic acids in samples are well known in the art, as are described, e.g., see Diaco in Innis (1995) *PCR Strategies*, supra, "Practical Considerations for the design of quantitative PCR assays", pg. 84–108. Branched DNA signal amplification is described in Urdea (1994) *Bio/Tech.* 12:926, and U.S. Pat. No. 5,124,246.

f. Partial Activity Telomerase Assays

In one embodiment of the invention, a variety of partial activity telomerase assays are provided to identify a variety of different classes of modulators of telomerase activity. The "partial activity" assays of the invention allow identification of classes of telomerase activity modulators that might otherwise not be detected in a "full activity" telomerase assay. One partial activity assay involves the non-processive activity of mTERT and telomerase enzyme. The processive nature of telomerase activity is described by Morin (1989) supra; see also Prowse (1993) "Identification of a nonprocessive telomerase activity from mouse cells" *Proc. Natl. Acad. Sci. USA* 90:1493–1497. Another partial activity assay of the invention exploits the "reverse-transcriptase-like" activity of telomerase. In these assays, one assays the reverse transcriptase activity of the mTERT protein or telomerase enzyme. See Lingner (1997) "Reverse transcriptase motifs in the catalytic subunit of telomerase" *Science* 276:561–567. Another partial activity assay of the invention exploits the "nucleolytic activity" of mTERT and telomerase enzyme, involving the enzyme's removing of at least one guanine "G" residue from the 3' strand. This nucleolytic activity has been observed in the Tetrahymena telomerase by Collins (1993) "Tetrahymena telomerase catalyzes nucleolytic cleavage and nonprocessive elongation" *Genes Dev* 7:1364–1376. Another partial activity assay of the invention involves analyzing mTERT's and telomerase enzyme's ability to bind nucleotides as part of its enzymatically processive DNA polymerization activity. Another partial activity assay of the invention involves analyzing mTERT's or telomerase enzyme's ability to bind its RNA moiety, ie., mTERC, used as a template for telomere synthesis.

Additional partial activity assays of the invention involve analyzing mTERT's and telomerase enzymes's ability to bind chromosomes in vivo, or to bind oligonucleotide primers in vitro or in reconstituted systems, or to bind proteins associated with chromosomal structure (see, for an example of such a protein, Harrington (1995) *J Biol Chem* 270: 8893–8901). Chromosomal structures which bind mTERT include, for example, telomeric repeat DNA, histones, nuclear matrix protein, cell division/cell cycle control proteins and the like. One of skill in the art can use the methods of the invention to identify which portions (e.g., domains) of these telomerase-associating proteins contact telomerase. In one embodiment of the invention, these TERT-binding and telomerase-associating proteins or fragments thereof are used as modulators of telomerase activity.

4. Modulators of Telomerase Activity

The invention provides methods and reagents for screening for compositions or compounds capable of modifying the ability of mTERT and mTERT-containing telomerase enzyme to synthesize telomere DNA ("full activity"). The invention also screens for modulators of any or all of mTERT's "partial activities," some of which are described above. In various embodiments, the invention includes, but is not limited to, screening for antagonists that: bind to mTERT's active site; inhibit the association of its RNA moiety, telomerase-associated proteins, nucleotides, or telomeric DNA to the telomerase enzyme or mTERT protein; promote the disassociation of the enzyme complex; or inhibit any of the "partial activities" described above.

Screening for antagonist activity provides for compositions that decrease telomerase enzyme activity, thereby preventing unlimited cell division of cells exhibiting unregulated cell growth, such as cancer cells. Telomerase enzyme activity has been identified as an important cancer marker, one whose levels can diagnose, prognose, and predict the outcome or seriousness of disease, as described in U.S. Pat. Nos. 5,489,508; 5,648,125; and 5,639,613. The present invention provides mTERT antagonists which can also inhibit the activity of hTERT, or can serve as a structural basis for developing hTERT antagonists, thus providing useful reagents for treating cancer by modulating telomerase activity.

Screening for agonist activity provides for compositions that increase telomerase's activity in a cell. Such agonist compositions provide for methods of creating a state of continuous proliferation or immortalizing otherwise normal, untransformed cells, including cells which can express useful proteins, as discussed above. Such agonists also provide for methods of controlling or delaying cellular senescence. The present invention provides mTERT agonists which can also increase the activity of hTERT, or can serve as a structural basis for developing hTERT agonists.

The methods of the invention are amenable to adaptations from protocols described in the scientific and patent literature and known in the art. For example, when a telomerase enzyme or mTERT protein of this invention is used to identify compositions which act as modulators of telomerase enzyme activities, large numbers of potentially useful molecules can be screened in a single test. The modulators can have an inhibitory (antagonist) or potentiating (agonist) effect on telomerase activity. For example, if a panel of 1,000 inhibitors is to be screened, all 1,000 inhibitors can potentially be placed into one microtiter well and tested simultaneously. If such an inhibitor is discovered, then the pool of 1,000 can be subdivided into 10 pools of 100 and the process repeated until an individual inhibitor is identified.

a. Synthetic Small Molecule Modulators

Potential modifiers of telomerase activity, i.e., test compounds, preferably of molecular weight under about 10,000 daltons; more preferably, under about 5,000 daltons; and most preferably, under about 500 daltons, include synthetic molecules, which can be designed and produced for testing by any technique, many of which are described in the patent and scientific literature, and a few illustrative examples are described below.

i. Combinatorial Chemistry Methodology

The creation and simultaneous screening of large libraries of synthetic molecules can be carried out using well-known techniques in combinatorial chemistry, e.g., see van Breemen (1997) *Anal. Chem.* 69:2159–2164; Lam (1997) *Anticancer Drug Des.* 12:145–167 (1997); Shipps (1997) *Proc. Natl. Acad. Sci. USA* 94:11833–11838; Kaur (1997) *J. Protein Chem.* 16:505–511; Zhao (1997) *J. Med. Chem.* 40:4006–4012, for screening solution-phase combinatorial libraries using pulsed ultrafiltration/electrospray mass spectrometry.

ii. Rational Drug Design

Rational drug design involves an integrated set of methodologies that include structural analysis of target molecules, synthetic chemistries, and advanced computational tools. When used to design modulators, such as antagonists/inhibitors of protein targets, such as mTERT protein and mTERT-containing telomerase enzyme, the objective of rational drug design is to understand a molecule's three-dimensional shape and chemistry. Rational drug design is aided by X-ray crystallographic data or NMR data, which can now be determined for the mTERT protein and telomerase enzyme in accordance with the methods and using the reagents provided by the invention. Calculations on electrostatics, hydrophobicities and solvent accessibility are also helpful. See, e.g., Coldren (1997) *Proc. Natl. Acad. Sci. USA* 94:6635–6640.

b. Inhibitory (Antagonist) and Activator (Agonist) Peptide Modulators

Potential modulators of mTERT and telomerase enzyme activity also include peptides. For example, oligopeptides with randomly generated sequences can be screened to discover peptide modulators (agonists or inhibitors) of mTERT and/or telomerase activity. Such peptides can be used directly as drugs or to find the orientation or position of a functional group that can inhibit telomerase activity that, in turn, leads to design and testing of a small molecule inhibitor. Peptides can be structural mimetics, and one can use molecular modeling programs to design mimetics based on the characteristic secondary structure and/or tertiary structure of telomerase enzyme and mTERT protein. Such structural mimetics can also be used therapeutically, in vivo, as modulators of telomerase activity (agonists and antagonists). Structural mimetics can also be used as immunogens to elicit anti-mTERT protein antibodies.

c. Inhibitory Natural Compounds as Modulators of Telomerase Activity

In addition, a large number of potentially useful activity-modifying compounds can be screened in extracts from natural products as a source material. Sources of such extracts can be from a large number of species of fungi, actinomyces, algae, insects, protozoa, plants, and bacteria. Those extracts showing inhibitory activity can then be analyzed to isolate the active molecule. See, e.g., Nisbet (1997) *Curr. Opin. Biotechnol.* 8:708–712; Turner (1996) *J. Ethnopharmacol.* 51:3943; Borris (1996) *J. Ethnopharmacol.* 51:29–38; Suh (1995) *Anticancer Res.* 15:233–239.

d. Inhibitory Oligonucleotides

One particularly useful set of inhibitors provided by the present invention includes oligonucleotides that are able to either bind mRNA encoding mTERT protein or to the mTERT gene, in either case preventing or inhibiting the production of functional mTERT protein. Other oligonucleotides of the invention interact with mTERT's RNA moiety, or are able to prevent binding of telomerase enzyme or mTERT to its DNA/telomere target, or one telomerase component to another, or to a substrate. Such oligonucleotides can also bind the telomerase enzyme or mTERT protein and inhibit a partial activity, as described above (such as its processive activity, its reverse transcriptase activity, its nucleolytic activity, and the like). The association can be though sequence specific hybridization to another nucleic acid or by general binding, as in an aptamer.

Another useful class of inhibitors includes oligonucleotides which cause inactivation or cleavage of mTERT mRNA or mTERC. That is, the oligonucleotide is chemically modified or has enzyme activity which causes such cleavage, such as is the case with ribozymes. As noted above, one may screen a pool of many different such oligonucleotides for those with the desired activity.

Another useful class of inhibitors includes oligonucleotides which bind polypeptides. Double- or single-stranded DNA or single-stranded RNA molecules that bind to specific polypeptide targets are called "aptamers." The specific oligonucleotide-polypeptide association may be mediated by electrostatic interactions. For example, aptamers specifically bind to anion-binding exosites on thrombin, which physiologically binds to the polyanionic heparin (Bock (1992) *Nature* 355:564–566). Because mTERT protein binds both mTERC (or hTERC) and its DNA substrate, and because the present invention provides mTERT and other mTERT-associated proteins in isolated and purified forms in large quantities, those of skill in the art can readily screen for mTERT-binding aptamers using the methods of the invention.

Antagonists of telomerase-mediated DNA replication can also be based on inhibition of mTERC (Norton (1996) *Nature Biotechnology* 14:615–619) through complementary sequence recognition or cleavage, as through ribozymes.

Telomerase activity can be inhibited by targeting mTERT mRNA with antisense oligonucleotides capable of binding mTERT mRNA. In some situations, naturally occurring nucleic acids used as antisense oligonucleotides may need to be relatively long (18 to 40 nucleotides) and present at high concentrations, a wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. PNAs targeting hTERC have been described, as well as methods for internalizing such PNAs in cells. See, U.S. Ser. No. 08/630,019, filed Apr. 9, 1996, and U.S. Ser. No. 08/838,545 and PCT/US/97/05931, filed on Apr. 9, 1997 (also, see Norton (1996) supra). Antisense oligonucleotides having phosphorothioate linkages can also be used, as described in WO 97/03211; WO 96/39154; Mata (1997) *Toxicol Appl Pharmacol* 144:189–197; Antisense Therapeutics, ed. Sudhir Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, and other synthetic, non-naturally occurring nucleotide and oligonucleotide mimetics.

As noted above, combinatorial chemistry methodology can be used to create vast numbers of oligonucleotides that can be rapidly screened for specific oligonucleotides that have appropriate binding affinities and specificities toward any target, such as the mTERT proteins of the invention, can be utilized (see Gold (1995) *J. of Biol. Chem.* 270:13581–13584).

i. Inhibitory Ribozymes

Ribozymes act by binding to a target RNA through the target RNA binding portion of a ribozyme which is held in close proximity to an enzymatic portion of the ribozyme that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, due to the enzymatic nature of a ribozyme, ribozyme technology can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target, and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of an antisense oligonucleotide binding the same RNA site.

The enzymatic ribozyme RNA molecule has complementarity to the target, such as the mRNA encoding mTERT. The enzymatic ribozyme RNA molecule is able to cleave RNA and thereby inactivate a target RNA molecule. The complementarity functions to allow sufficient hybridization of the enzymatic ribozyme RNA molecule to the target RNA for cleavage to occur. One hundred percent complementarity is preferred, but complementarity as low as 50–75% may also be employed. The present invention provides ribozymes targeting any portion of the coding region for an mTERT gene or gene product, i.e., any ribozyme that can cleave a TERT mRNA or a TERT gene in a manner that will inhibit the translation or transcription of the mRNA and thus reduce telomerase activity. In addition, the invention provides ribozymes targeting the nascent, unspliced RNA transcript of the mTERT gene to reduce telomerase activity.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) *Aids Research and Human Retroviruses* 8:183; hairpin motifs by Hampel (1989) *Biochemistry* 28:4929, and Hampel (1990) *Nuc. Acids Res.* 18:299; the hepatitis delta virus motif by Perrotta (1992) *Biochemistry* 31:16; the RNaseP motif by Guerrier-Takada (1983) *Cell* 35:849; and the group I intron by Cech, et al., U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

ii. Delivery of mTERT Inhibitory Oligonucleotides

The mTERT-inhibitory oligonucleotides of the invention can be transferred into the cell using a variety of techniques well known in the art. For example, oligonucleotides can be delivered into the cytoplasm spontaneously, without specific modification. Alternatively, they can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. For example, a DNA binding protein, e.g., HBGF-1, is known to transport oligonucleotides into a cell. See, e.g., Tseng (1997) *J. Biol. Chem.* 272:25641–25647; Satoh (1997) *Biochem. Biophys. Res. Commun.* 238:795–799, describing efficient gene transduction by Epstein-Barr-virus-based vectors coupled with cationic liposome and HVJ-liposome.

The procedures for delivering the oligonucleotides of the invention to cells in vitro are useful in vivo. For example, by using liposomes, particularly where the liposome surface carries ligands specific for target cells, or are otherwise preferentially directed to a specific organ, one may provide for the introduction of the oligonucleotides into the target cells in vivo. See, e.g., Huwyler(1997) *J. Pharmacol. Exp. Ther.* 282:1541–1546, describing receptor mediated delivery using immunoliposomes.

Alternatively, the cells may be permeabilized to enhance transport of the oligonucleotides into the cell, without injuring the host cells. See, e.g., Verspohl (1997) *Cell. Biochem. Funct.* 15:127–134; Kang (1997) *Pharm. Res.* 14:706–712; Bashford (1994) *Methods Mol. Biol.* 27:295–305, describing use of bacterial toxins for membrane permeabilization; and for general principles of membrane permeabilization, see Hapala (1997) *Crit. Rev. Biotechnol.* 17:105–122.

e. Telomerase-associated Proteins as Dominant Negative Mutants

In one embodiment of the invention, telomerase-associated proteins are used as modulators of murine telomerase enzyme and mTERT activity. Telomerase-associated proteins include chromosomal structures, such as histones, nuclear matrix protein, cell division/cell cycle control proteins and the like. Other telomerase-associated proteins which can be used as modulators for the purpose of the invention include p80, p95, and human proteins, such as TP1 (Saito (1997) *Genomics* 46:46–50), TPC-2, TPC-3 (U.S. Ser. No. 08/710,249, filed Sep. 13, 1996) and PIN2 (Shen (1997) *Proc. Natl. Acad. Sci. USA* 94:13618–13623), TRF-1 and TRF-2 (Chong (1995) *Science* 270:1663–1667; Broccoli (1997) "Human telomeres contain two distinct Myb-related proteins, TRF1 and TRF2," *Nat. Genet.* 17:231–235). In addition, TERT binding fragments of these chromosomal telomerase-associated proteins can be identified by the skilled artisan in accordance with the methods of the invention and used as modulators of telomerase activity (see also, e.g., Lauber (1997) *J. Biol. Chem.* 272:24657–24665, to identify nuclear matrix DNA attachment sites).

i. Identifying Telomerase-associated Proteins for Use as Modulators

In one embodiment of the invention, mTERT and mTERT-containing telomerase enzyme are used to identify telomerase-associated proteins, i.e., telomerase accessory proteins which modulate or otherwise complement telomerase activity. As noted above, these proteins or fragments thereof can modulate function by causing the dissociation or prevention the association of the telomerase enzyme complex, prevent the assembly of the telomerase complex, prevent mTERT from binding to its nucleic acid complement or to its DNA template, prevent mTERT from binding nucleotides, or prevent, augment, or inhibit any one, several or all of the partial activities of telomerase enzyme or mTERT protein.

The skilled artisan can use a variety of well-known techniques to identify telomerase-associated proteins, including phage display (Katz (1997) *Annu. Rev. Biophys. Biomol. Struct.* 26:27–45), the two hybrid system (as in James (1996) *Genetics* 144:1425–1436; Adey (1997) *Biochem. J.* 324:523–528; Cowell (1997) "Yeast two-hybrid library screening," *Methods Mol. Biol.* 69:185–202), and disease correlation. Other well-known techniques include co-immunoprecipitation analysis, as used in Zhao (1994) *J.*

*Biol. Chem.* 269:15577–15582. Another well known technique for isolating co-associating proteins involves the use of chemical cross-linkers, including cleavable cross-linkers dithiobis (succinimidylpropionate) and 3,3'-dithiobis (sulfosuccinimidyl-propionate); see e.g., Tang (1996) *Biochemistry* 35:8216–8225. Photocross linking experiments implicated a 123 kd protein in the specific binding of telomeric DNA substrate in *Euplotes aediculatus* (Lingner (1996) *Proc. Natl. Aca. Sci. U.S.A.* 93:10712).

ii. Dominant-negative Mutants of mTERT

The present invention provides non-functional, "dominant-negative" mTERT mutants. Dominant-negative mutant forms of enzymes can be used to competitively substitute for endogenous forms of the enzyme to affect the function, structure (e.g., as as herterocomplex, a quaternary structure) location, half-life, or compartmentalization of the enzyme. The invention provides for mTERT telomerase mutant forms that can competitively interfere with or replace wild-type (native) form of mTERT. Such mutant mTERTs can, e.g., interfere with or replace native mTERT in the formation of the telomerase enzyme complex (i.e., mTERT with mTERC) or compete for mTERT-telomere binding sites. In this manner, the effective amounts of functional telomerase in the cell can be reduced or altered or a new function or form of telomerase can be created. This can be used, e.g., to have a therapeutic effect, by reducing the level of telomerase activity in a cancer cell, to modulate telomere length in a cell, study the consequence of a TERT mutation, or to elucidate biological functions of a TERT or its mutants.

Mutations creating dominant-negative forms of mTERT can be generated by, e.g., mutating any of the above-described TERT motifs or other codons of the mTERT gene. For example, codons for the conserved amino acid residues in each of any of the conserved TERT motifs can be changed to other codons, resulting in a variety of coding sequences which express a partially non-functional mTERT. Eight highly conserved motifs have been identified in TERTs of different species, including mouse and man, see Lingner (1997) supra. FIG. 3 shows the alignment of mTERT with hTERT, and positions of motifs are indicated. FIGS. 4 and 5 show mTERT motifs in relation to the sequence conservation between mTERT and other TERTs: human, *Euplotes aediculatus, Saccharomyces cerevisiae, Schizosaccharomyces pombe*. Thus, the present invention provides a wide variety of "mutated" telomerase enzymes and mTERT proteins which have a partial activity but not full activity of telomerase enzyme.

For example, one such telomerase is able to bind telomeric structures, but not bind telomerase-associated RNA (i.e., mTERC). If expressed at high enough levels, such a telomerase mutant can deplete a necessary telomerase component (e.g., the telomere binding site) and thereby function as an inhibitor of wild-type telomerase activity. A mutated telomerase acting in this manner is as an antagonist or a so-called "dominant negative" mutant.

Example 8 below describes three mutants of mTERT which are predicted to be deficient in a telomerase activity. These mutations change amino acids in the conserved RT motifs previously shown to be essential for RT function (Lingner (1997) supra). The predictions are based on similar results for analogous mutations in hTERT (Weinrich (1997) supra). The mutations are created using the procedures described in Weinrich (1997) supra.

5. Definitions

To facilitate understanding the invention, a number of terms are defined below.

The term "antibody" refers to a polypeptide substantially encoded by an immunoglobulin gene or immunoglobulin genes, or fragments or synthetic or recombinant analogues thereof which specifically bind and recognize analytes and antigens. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. Antibodies exist, e.g., as intact immunoglobulins or as a number of well characterized fragments produced by digestion with various peptidases, see, FUNDAMENTAL IMMUNOLOGY, 3RD ED., W. E. Paul, ed., Raven Press, N.Y. (1993). While various antibody fragments are defined in terms of the digestion of an intact antibody, one of skill will appreciate that such fragments may be synthesized de novo either chemically or by utilizing recombinant DNA methodologies, for example, recombinant single chain Fv or antibodies or fragments thereof displayed on the surface of a phage, virus or a cell. The term "immunologically reactive conditions" refers to an environment in which antibodies can bind to antigens, such as an mTERT of the invention. As discussed below, this can be an immunological binding assay. The phrase "specifically binds to an antibody" when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies specific for the mTERT protein of this invention or to any portion or the protein defined by the sequence of SEQ ID NO:2 can be selected to immunoreact specifically with all murine mTERT species of the invention or only a single mTERT specie (an allele, homologue, or isoform), and not with non-mouse TERT proteins or non-telomerase proteins. As described below, a variety of immunoassay formats may be used to select antibodies specifically immunoreactive with a particular protein, such as mTERT. For example, solid-phase ELISA immunoassays are routinely used to select monoclonal antibodies specifically immunoreactive with mTERT. See Harlow and Lane, supra, for a description of immunoassay formats and conditions that can be used to determine specific immunoreactivity, a specific or selective reaction is one which generates a signal at least twice (2×) over background signal or "noise."

The term "buffered aqueous solution compatible with telomerase activity" refers to conditions suitable for in vitro reactions, such as in vitro transcription and translation reactions, or activity assays, i.e., compatible physiological conditions. The term refers to temperature, pH, ionic strength, viscosity, and like biochemical parameters which can be compatible with a telomerase enzyme or mTERT activity, full or partial, e.g., such as those conditions that exist in a viable organism, e.g. conditions which typically exist intracellularly in a viable cultured eukaryotic cell, such as a yeast or a mammalian cell. Compatible physiologic conditions for mTERT and telomerase enzyme activity (conditions suitable for in vitro reactions), however, can be substantially different from conditions which typically exist intracellularly. For example, the intracellular conditions in a yeast cell grown under typical laboratory culture conditions are considered physiological conditions. In general, in vitro physiological conditions comprise 50–200 mM NaCl or KCl, pH 6.5–8.5, 20–45 EC and 0.001–10 mM divalent cation (e.g., $Mg^{++}$, $Ca^{++}$), preferably about 150 mM NaCl or KCl, pH 7.2–7.6, 5 mM divalent cation, and often include 0.01–1.0 percent nonspecific protein (e.g., BSA). In addition, a non-ionic detergent (Tween, NP40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions can be applicable: 10–250 mM NaCl, 5–50 mM Tris HCl, pH 5–8, with optional addition of divalent cation (s) and/or: metal chelators; nonionic detergents; membrane fractions; antifoam agents; and/or scintillants.

The term "conservative substitution" refers to a change in the amino acid composition of a protein, such as the mTERT of the invention, that does not substantially alter the protein's activity. This includes conservatively substituted variations of a particular amino acid sequence, ie., amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another: 1) Alanine (a), Serine (S), Threonine (T); 2) Aspartic acid (D), Glutamic acid (E); 3) Asparagine (N), Glutaine (Q); 4) Arginine (R), Lysine (K); 5) Isoleucine (1), Leucine (L), Methionine (M), Valine (V); and 6) Phenylalanine (F), Tyrosine (Y), Tryptophan (W) (see also, Creighton (1984) *Proteins*, W.H. Freeman and Company). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions which alter, add or delete a single amino acid or a small percentage of amino acids in an encoded sequence can also be considered "conservatively substituted variations." The term "conservative substitution" also refers to a change in a nucleic acid sequence such that the substitution does not substantially alter the contemplated activity of the nucleic acid, for example, as not changing the activity of the protein encoded by the nucleic acid, a nucleic acid sequence of the invention implicitly encompasses conservatively modified variants thereof (e.g. degenerate codon substitutions) and complementary sequences and not just the sequence explicitly indicated. Specifically, degenerate codon substitutions may be achieved by generating sequences in which the third position of one or more selected (or all) codons is substituted with mixed-base and/or deoxyinosine residues (Batzer (1991) *Nucleic Acid Res*. 19:5081; Ohtsuka (1985) *J. Biol. Chem*. 260:2605–2608; Rossolini (1994) *Mol. Cell. Probes* 8:91–98).

The term "expression vector" refers to any recombinant expression system for the purpose of expressing a nucleic acid sequence of the invention, as SEQ ID NO:1, in vitro or in vivo, constitutively or inducibly, in any cell, including prokaryotic, yeast, fungal, plant, insect or mammalian cells. The term includes linear or circular expression vectors. The term includes expression vectors that remain episomal or integrate into the host cell genome. The expression vectors can have the ability to self-replicate or not, i.e., drive only transient expression in a cell. The term includes recombinant expression vector "cassettes" which contain only the minimum elements needed for transcription of the recombinant nucleic acid. See, e.g., Arnaud (1997) *Genex* 199:149–156.

A "fusion protein" refers to a composition comprising at least one polypeptide or peptide domain which is associated with a second typically polypeptide or peptide domain. The polypeptide or peptide domain can comprise an mTERT or subsequence thereof. The second domain can be a polypeptide, peptide, polysaccharide, polynucleotide, or the like. The "fusion" can be an association generated by a chemical linking or by a charge (electrostatic attraction, i.e., salt bridges, H-bonding, etc.) interaction. If the polypeptides are recombinant, the "fusion protein" can be translated from a common message. Alternatively, the compositions of the domains can be linked by any chemical or electrostatic means. The invention includes compositions which are "fusion proteins" comprising mTERT and non-mTERT (exogenous) polypeptide sequences or compositions to aid in cell targeting, purification, expression and/or detection of mTERT and murine telomerase enzyme.

The terms "isoform," "allele," and "homologue" refer to a nucleic acid or polypeptide mTERT specie. The nucleic acid or protein can be considered an mTERT isoform, homologue or allele if it shares at least 40 percent to 50 percent sequence identity to any known mTERT specie, including but not limited to the mTERT identified by SEQ ID NO:1 or SEQ ID NO:2, respectively.

As used herein, "isolated," when referring to a molecule or composition, such as, e.g., an mTERT or a telomerase-associated nucleic acid or polypeptide, means that the molecule or composition is separated from at least one other compound, such as a protein, other nucleic acids (e.g., RNAs), or other contaminants with which it is associated in vivo or in its naturally occurring state. Thus, an mTERT is considered isolated when the mTERT has been isolated from any other component with which it is naturally associated, e.g., cell membrane, as in a cell extract. An isolated composition can, however, also be substantially pure. An isolated composition can be in a homogeneous state and can be in a dry or an aqueous solution. Purity and homogeneity can be determined, for example, using analytical chemistry techniques such as polyacrylamide gel electrophoresis (SDS-PAGE) or high performance liquid chromatography (HPLC).

The term "label" refers to a detectable composition, such as by spectroscopic, photochemical, biochemical, immunochemical, physical or chemical means. For example, useful labels include $^{32}P$, $^{35}S$, $^{3}H$, $^{14}C$, $^{125}I$, $^{131}I$, fluorescent dyes (e.g., FITC, rhodamine, lanthanide phosphors), electron-dense reagents, enzymes, e.g. as commonly used in an ELISA (e.g., horseradish peroxidase, beta-galactosidase, luciferase, alkaline phosphatase), biotin, dioxigenin, or haptens and proteins for which antisera or monoclonal antibodies are available. The label can be directly incorporated into the nucleic acid, peptide or other target compound to be detected, or it can be attached to a probe or antibody which hybridizes or binds to the target, a peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance or impact on other useful or desired properties. See e.g., Mansfield (1995) *Mol. Cell Probes* 9:145–156.

The term "modulator" refers to any synthetic or natural compound or composition that can change in any way either the "full" or any "partial activity" of a TERT or a telomerase enzyme, a modulator can be an agonist or an antagonist, a modulator can be, but is not limited to, any organic and inorganic compound; including, e.g., small molecules, peptides, proteins, sugars, nucleic acids, fatty acids and the like.

The term "murine" refers to any and all members of the family Muridae, including rats and mice. As used herein, the term "mouse" and "mice" encompass all members of the family Muridae. Thus, the term "mTERT," as defined below, "murine TERT" and "mouse TERT" are equivalent and encompass TERT species from all members of the family Muridae.

The term "nucleic acid molecule" or "nucleic acid sequence" refers to a deoxyribonucleotide or ribonucleotide oligonucleotide in either single- or double-stranded form. The term encompasses nucleic acids, i.e., oligonucleotides, containing known analogues of natural nucleotides which have similar or improved binding or other properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methyl-phosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923–1937; Antisense Research and Applications (1993, CRC Press) in its entirety and specifically Chapter 15, by Sanghvi, entitled "Heterocyclic base modifications in nucleic acids and their applications in antisense oligonucleotides." PNAs contain non-ionic backbones, such as N-(2-aminoethyl) glycine units, as described in U.S. Ser. No. 08/630,019, filed 9 Apr. 1996, and the US CIP U.S. Ser. No. 08/838,545 and PCT application PCT/US/97/0593 1, both filed on Apr. 9, 1997. Phosphorothioate linkages are described in WO 97/03211; WO 96/39154; Mata (1997) *Toxicol Appl Pharmacol* 144:189–197. Other synthetic backbones encompassed by the term include, e.g., methylphosphonate linkages or alternating methylphosphonate and phosphodiester linkages (Strauss-Soukup (1997) *Biochemistry* 36:8692–8698), and benzylphosphonate linkages, which, when compared with unmodified oligonucleotides and methylphosphonates, are more stable against nucleases and exhibit a higher lipophilicity (Samstag (1996) *Antisense Nucleic Acid Drug Dev* 6:153–156). The term nucleic acid is used interchangeably with gene, cDNA, mRNA, oligonucleotide primer, probe and amplification product. The terms "exogenous nucleic acid" and "heterologous nucleic acid" refer to a nucleic acid that has been isolated, synthesized, cloned, ligated, excised in conjunction with another nucleic acid, in a manner that is not found in nature, and/or introduced into and/or expressed in a cell or cellular environment other than or at levels or forms different than the cell or cellular environment in which said nucleic acid or protein is found in nature. The term encompasses both nucleic acids originally obtained from a different organism or cell type than the cell type in which it is expressed and also nucleic acids that are obtained from the same cell line as the cell line in which it is expressed.

The term "recombinant," when used with reference to a cell, or to a nucleic acid, protein or vector, refers to a material or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell or express native genes or gene products that are otherwise expressed at a different level, typically, under-expressed or not expressed at all. The term "recombinant means" encompasses all means of expressing, ie., transcription or translation of an isolated and/or cloned nucleic acid in vitro or in vivo. For example, the term "recombinant means" encompasses techniques where a recombinant nucleic acid, such as a cDNA encoding a protein, is inserted into an expression vector (including "expression cassettes"), the vector is introduced into a cell, i.e., the cell is "transfected" or "transformed" and the cell expresses the protein. "Recombinant means" also encompass the ligation of nucleic acids having coding or transcriptional regulatory (e.g., promoter) sequences from different sources into one expression cassette or vector for expression of a fusion protein, constitutive expression of a protein, or inducible expression of a protein, such as the mTERT protein of the invention.

The terms "homology," "sequence identity" and "sequence similarity" refers to a degree of complementarity or sequence identity. There may be partial homology or complete homology (ie., identity), a partially complementary sequence is one that at least partially inhibits a completely complementary sequence from hybridizing to a target nucleic acid and can be referred to using the functional term as "substantially homologous" to the completely complementary sequence. The inhibition of hybridization of the completely complementary sequence to the target sequence may be examined using a hybridization assay (Southern or Northern blot, solution hybridization and the like) under conditions of low stringency, a substantially homologous sequence or probe will compete for and inhibit the binding (i.e., the hybridization) of a completely homologous nucleic acid to a target nucleic acid under conditions of low stringency. This is not to say that conditions of low stringency are such that non-specific binding is permitted; low stringency conditions require that the binding of two sequences to one another be a specific (ie., selective) interaction. The absence of non-specific binding may be tested by the use of a second target which lacks even a partial degree of complementarity; in the complete absence of non-specific binding the probe will not hybridize to the second non-complementary target. The terms "sequence identity," "sequence similarity" and "homology" refer to two or more sequences, such as the diverse nucleic acid and amino acid sequences of the mTERT proteins of the telomerase of the invention, that, when optimally aligned, as with the programs BLAST, GAP, FASTA or BESTFIT, share at least 40 percent to 50 percent sequence identity, and preferably at least 60 percent or greater sequence identity. "Percentage amino acid sequence identity" refers to a comparison of the sequences of two TERT nucleic acids or polypeptides which, when optimally aligned, have approximately the designated percentage of the same nucleotides or amino acids, respectively. For example, "60% sequence identity" and "60% homology" refer to a comparison of the sequences of two nucleic acids or polypeptides which, when optimally aligned, have 60% identity.

The term "an mTERT" polypeptide comprising an amino acid sequence with significant sequence identity to a motif refers to mTERT proteins which are considered to have a statistically significant sequence identity, ie., have significant homology or be significantly identical, at the amino acid sequence level in a conserved region of a TERT protein, such as the motif sequences defined herein. Two TERT proteins are considered to have a statistically significant sequence identity in the conserved region if, after adjusting for deletions, additions and the like, the conserved regions have at least out 20% to 30% sequence identity or greater sequence identity, preferably higher, for example, about 40% to 50% or higher (ie., 80% to 90%) if the region of comparison is shorter, ie., a region of about ten consecutive amino acids.

The terms "stringent hybridization," "stringent conditions," or "specific hybridization conditions" refer to conditions under which an oligonucleotide (when used, for example, as a probe or primer) will hybridize to its target subsequence, such as an mTERT sequence of a nucleic acid in an expression vector of the invention but not to a non-telomerase sequence. Stringent conditions are sequence-dependent. Thus, in one set of stringent conditions an oligonucleotide probe will hybridize to only one specie mTERT of the invention. In another set of stringent conditions (less stringent) an oligonucleotide probe will hybridize to all species of mTERT but not to non-telomerase nucleic acids. Longer sequences hybridize specifically at higher temperatures. Stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium (if the target sequences are present in excess, at $T_m$, 50% of the probes are occupied at equilibrium). Typically, stringent conditions will be those in which the salt concentration is less than about 1.0 M sodium ion, ie., about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Often, high stringency wash conditions are preceded by low stringency wash conditions to remove background probe signal. An example of medium stringency wash conditions for a duplex of, e.g., more than 100 nucleotides, is 1×SSC at 45° C. for 15 minutes (see Sambrook for a description of SSC buffer). An example of a low stringency wash for a duplex of, e.g., more than 100 nucleotides, is 4–6×SSC at 40° C. for 15 minutes, a signal to noise ratio of 2× (or higher) than that observed for an unrelated probe in the particular hybridization assay indicates detection of a "specific hybridization." Nucleic acids which do not hybridize to each other under stringent conditions can still be substantially identical if the polypeptides which they encode are substantially identical. This can occur, e.g., when a nucleic acid is created that encodes for conservative substitutions. Stringent hybridization and stringent hybridization wash conditions are different under different environmental parameters, such as for Southern and Northern hybridizations. An extensive guide to the hybridization of nucleic acids is found in Tijssen (1993) supra.

The term "subsequence" refers to a sequence of a nucleic acid or protein or an amino acid that comprises a part of a longer sequence of a nucleic acid or a protein (e.g., polypeptide), respectively.

The term "test compound" refers to any synthetic or natural compound or composition. The term includes all organic and inorganic compounds; including, for example, small molecules, peptides, proteins, sugars, nucleic acids, fatty acids and the like.

The terms "transformed cell" and "transfected cell" refers to any cell into which a heterologous or exogenous nucleic acid has been inserted, either transiently or stably, by recombinant means, i.e., by human intervention.

The terms "TERT" and "telomerase reverse transcriptase" refer to a telomere-specific RNA-dependent DNA polymerase protein, the telomerase holoenzyme without an RNA component, the catalytic subunit of the telomerase enzyme complex. The term "telomerase," "telomerase enzyme" and "telomerase enzyme complex" refers to a TERT with at least one RNA component, i.e., an RNA moiety used as a template for DNA synthesis. The telomerase enzyme can also include other telomerase-associated compositions. The telomerase can utilize a portion of its RNA moiety as a template to specify the addition of telomeric DNA repeat sequences to chromosomal ends. The term "mTERT" and "murine TERT" refer to murine TERT nucleic acids and proteins with common structural and functional characteristics. mTERT nucleic acids can be characterized as an mTERT protein having a calculated molecular weight of between about 50 and 150 kDa and specifically binding to an antibody raised against a protein having a sequence of amino acids as in SEQ ID NO:2 or a subsequence thereof or having at least 60% amino acid sequence identity to a protein having a sequence of amino acids as in SEQ ID NO:2. mTERT nucleic acids also comprise nucleic acids which specifically hybridize to SEQ ID NO:1 under stringent conditions, and nucleic acids encoding a protein which specifically binds to an antibody directed against an mTERT protein having a sequence of amino acids as in SEQ ID NO:2. mTERT proteins can be characterized as having a calculated molecular weight of about 50 to 150 kDa and specifically binding to an antibody raised against a mTERT protein having a sequence of amino acids as in SEQ ID NO:2 or subsequence thereof or having 60% amino acid sequence identity to a mTERT protein having a sequence of amino acids as in SEQ ID NO:2. Isolated or recombinant mTERT proteins within the scope of the claimed invention encompass murine proteins comprising species with common structural characteristics, i.e., motifs, as discussed in detail herein. The mTERTs of the invention include: species capable of catalyzing the synthesis of telomeres when associated with an RNA moiety, such as mTERC or hTERC; species capable of one or several or all partial activities of mTERT and telomerase enzyme; and species such as mTERT isoforms, homologues, and alleles which are considered mTERT species of the invention because they contain requisite common structural mTERT characteristics (i.e., TERT motifs) or sufficient sequence identity with any other mTERT specie. mTERT species include mTERT from all murine or Muridae family species, including mice and rats, as defined above. The term "an endogenous mTERT gene which has been mutated by recombinant means" refers to a gene which has been altered by a change in coding or non-coding, transcribed or untranscribed, or mTERT transcriptional regulatory sequences. If such a mutated gene is in a cell that is placed in an animal, the resultant transgenic non-human animal can be referred to as an "mTERT knockout" cell or animal, as described, supra.

The terms "telomerase activity" and "telomerase reverse transcriptase activity" ("TERT activity") can refer to either "full" or any "partial activity" of a TERT or telomerase enzyme. TERT activity includes the ability to synthesize DNA, such as a telomere or telomeric DNA, using a nucleic acid template, such as the telomerase RNA, a TERT "partial activity" can include, but is not limited to, such functions as the ability of TERT to: bind substrate DNA; bind a telomerase RNA moiety, i.e., mTERC or hTERC; catalyze the addition of nucleotides to a DNA substrate; bind deoxynucleotide substrate; exhibit "nucleolytic activity" (see Collins (1993) *Genes Dev* 7:1364–1376); bind telomere-associated proteins or chromosomal structures; exhibit the "processive" or "non-processive" activity of telomerase (see Morin (1989) supra); exhibit "reverse-transcriptase-like activity" of telomerase (see Lingner (1997) supra); bind nucleotides as part of its processive enzymatic DNA polymerization activity; bind chromosomes in vivo; bind oligonucleotide primers in vitro (Harrington (1995) *J Biol Chem* 270: 8893–8901) or in reconstituted systems; and bind histones, nuclear matrix protein, cell division/cell cycle control proteins and the like.

The examples and embodiments described herein are for illustrative purposes only, and various modifications or changes in light thereof will be suggested to persons skilled in the art and thereby are to be included within the spirit and purview of this disclosure and scope of the appended claims.

EXAMPLES

The following examples are offered to illustrate, but not limit the claimed invention.

Example 1

Isolating, Cloning and Sequencing mTERT cDNA and Genomic DNA

The following example details the isolation, cloning and sequencing of mTERT cDNA and mTERT genomic DNA, including transcriptional control elements and intronic sequences.

Mouse cDNA and genomic clones of TERT are provided by the invention to, e.g., construct homozygous or heterozygous deletions or other modifications of mTERT (i.e., deletions in either one or both alleles), e.g., as in mTERT "knockout" cells or mice; construct recombinant nucleic acids encoding mTERT proteins differing in amino acid sequence at one or more positions relative to native mTERT; characterize mTERT biochemistry and biology; identify and isolate additional mTERT species (alleles, isoforms, homologues); express mTERT and mTERC or mTERT and hTERC in "knockout" animals, e.g., those unable to express endogenous TERT or telomerase enzyme; express mTERT and mTERC or hTERC in cell-free transcription/translation systems; and express mTERT in cells or organisms which have retained the ability to express endogenous telomerase and/or mTERC.

General Techniques for Cloning of mTERT cDNA and Genomic Sequences

To obtain a clone of an mTERT, a hybridization step is typically performed, a probe is constructed from a known mTERT provided by the invention, such as the nucleic acid sequence set forth in SEQ ID NO:1, or a TERT from another organism, such as hTERT. The probe can be synthetically generated or it can be generated by PCR. The probe can incorporate a synthetic fragment, a PCR fragment or a restriction fragment(s) of a nucleic acid comprising all or pat of the TERT gene or the TERT coding sequence, which is then hybridized to DNA or RNA from the target mouse cell.

The mouse DNA can be genomic DNA, a genomic DNA library, RNA, cDNA, a cDNA library, or other sources of nucleic acid. In one embodiment, a mouse cDNA library is screened to obtain a fragment of mTERT cDNA. This fragment or its sequence can be further used to identify a genomic clone or additional cDNA clones. Use of cDNA may have advantages in that it is typically free of introns. The source of the cDNA library is important; it is preferably from a tissue known to possess telomerase activity or TERT RNA. An embryonic stem cell cDNA library is a preferred source of mTERT mRNA, as telomerase enzyme is expressed in stem cells.

The invention provides TERT sequence-containing probes useful for such screening, including the full length mTERT cDNA (SEQ ID NO:1) and various fragments of mTERT cDNA. One such probe includes a portion of TERT encompassing approximately the first third of a TERT cDNA, such as the first third of mTERT (SEQ ID NO:1). This region is more GC rich than the rest of the protein and may be preferred for detecting additional mTERT species in some circumstances. Thus, one embodiment uses this subfragment of mTERT, or, analogously, the first third of hTERT, or any other known TERT, as probes in screening for additional species.

Another embodiment provides for a probe including a portion of TERT encompassing approximately the middle third of a TERT cDNA, such as mTERT cDNA (SEQ ID NO:1). This region encodes a subset of the RT motifs and is likely to be the most conserved region and so is preferred in some circumstances. Thus, a preferred embodiment uses this subfragment of mTERT, or, analogously, the middle third of hTERT, or any other known TERT, as probes in screening for additional species.

An additional embodiment provides for a probe that is a portion of TERT encompassing approximately the last third of a TERT cDNA, such as the mTERT cDNA (SEQ ID NO:1). An alternative embodiment uses this subfragment of TERT, or, analogously, the last third of hTERT, or any other known TERT, as probes in screening.

The screen can be performed with a mixture of the probes to ensure the detection of at least one clone. Once a clone is identified, it can be screened with each probe independently to identify the region it encompasses. Then, the probes can be used independently to find missing regions, if any. When an mTERT is identified, a screen of a mouse genomic library can be performed using the mTERT clone as a probe. If the initial hybridization uses a non-mouse probe, such as hTERT, it can be performed at reduced stringency. As isoforms, homologues, and alleles of mTERT genes are expected to be about 60–95% identical to other TERTs, such as hTERT, appropriate hybridization conditions can be readily calculated, see e.g., Sambrook.

The mouse genomic clone and genomic sequences can be used, e.g, to prepare constructs for making transgenic mice expressing TERT. The mTERT constructs of the invention can be used to create an mTERT knockout cell or mouse by homologous recombination, as discussed herein in relation to knockout procedures. To clone an entire genomic mTERT, multiple large genomic lambda clones can be used to span the entire mouse genomic sequence.

In one embodiment, a mouse ES library is used to identify a mouse TERT-encoding nucleic acid clone, a preferred library is the Mouse Embryonic Stem Cell 5'-STRETCH cDNA library, cat # ML1049a, Clontech, Palo Alto, Calif., average insert size 1.6 Kb (0.8–4.5 Kb range), vector=lgt10, oligo dT and random hexamer primed with EcoRI linkers, RNA source=D3 cell line (pluripotent ES cells) (Doetschman (1985) *J. Embryol. Exp. Morphol.* 87:27–45).

Cloning of the m TERT cDNA and mTERT Genomic Nucleic Acid

A conventionally constructed mouse embryonal stem cell cDNA lambda gt10 phage library (Clontech, Palo Alto, Calif.) was screened using three human hTERT nucleic acid probes. The probes were designated A, B, and C, each approximately the same size, encompassing almost the entire hTERT coding region, running 5' to 3', respectively. These probes were derived from the hTERT-containing plasmid pGRN121, ATCC Accession No. ATCC209016, deposited May 6, 1997, and described in U.S. Ser. No. 08/915,503, U.S. Ser. No. 08/912,951, and, U.S. Ser. No. 08/911,312, all filed Aug. 14, 1997; and in U.S. Ser. No. 08/974,549, and U.S. Ser. No. 08/974,584, both filed on Nov. 19, 1997. Probe A is an Eco47111/Eco47111, 1203 base pair long fragment encompassing residues 729 to 1932 of pGRN121; probe B is a Sph1/Xmn1, 1143 base pair long fragment encompassing residues 2278 to 3421 of pGRN121; and probe C is an Xmn1/Msc1, 760 base pair long fragment encompassing residues 3421 to 4181 of pGRN121. The probes were hybridized using a conventional, low stringency hybridization protocol, with prehybridization and hybridization solutions containing 35% formamide at 37° C. for 12 hours.

A recombinant phage cDNA clone which specifically hybridized to the hTERT probe was isolated. A TERT-encoding 2 kb long nucleic acid insert was isolated, subcloned into a plasmid, and sequenced. The plasmid with this insert is designated pGRN227. Analysis of this sequence, including its comparison to known TERT sequences, was performed. The analysis determined that the insert possessed extensive sequence homology with hTERT, matching about 70% of the DNA sequence of hTERT around positions 1870 to 2150 of plasmid pGRN121. The 2 kb insert was 2006 base pairs long. Sequence analysis indicated that it included 1977 base pairs of mTERT coding sequence, which is about half the mTERT protein's open reading frame. The insert included some 5' non-coding sequence and sufficient coding (open reading frame, or ORF) sequence to identify the TERT motifs 1 and 2, which, based on related TERT sequences, was determined to be about half of the ORF for the mTERT protein.

To isolate the remaining coding sequence, a PCR amplification reaction was carried out using cDNA prepared from mouse testis polyA+ mRNA (Clontech, Palo Alto, Calif.). PCR amplification primers were designed: the primer pair included a 5' primer with sequence from the above-described 2 kb insert (called mTRT.9) (5'-CTTTTACATCACAGAGAGCAC-3') (SEQ ID NO:15) and a 3' primer from a conserved region of hTERT (called hTRT.28) (5'-CTCGGACCAGGGTCCTGAGGAA-3') (SEQ ID NO:8), a conventional RT-PCR protocol was used. The resultant amplified segment was subcloned into a plasmid and sequenced. The plasmid with this insert is called mTRT Ra3' (pGRN230). Analysis of the sequence showed that this cDNA insert included further coding sequence of mTERT, including new coding sequence 3' to the initially characterized 2 kb segment. Analysis of this cDNA sequence indicated that this second amplification product included TERT motifs T, 1, 2, A, B', and C. This amplified sequence did not include the entire mTERT coding sequence. Approximately 800 base pairs of coding sequence and the 3' untranslated region remained to be isolated.

To isolate the remaining 3' end of the mTERT sequence, bacterial artificial chromosomes (BAC clones) containing genomic mouse DNA were screened by Southern hybridization using probes designed from hTERT, as described above. Conventional, low stringency hybridization protocols were used, together with the probes designated A, B and C, described above, a clone that positively hybridized to probe C, under selective conditions, was isolated. Genomic BAC clones (BAC 495-M5 and 145 K20) were isolated and the inserts subcloned as Pst1 fragments (called mTRT Pst1, mTRT Pst3, and mTRT 496-2A2). Sequence analysis of these clones indicated that they included the 3' one third of the mTERT coding sequence, including the 3' untranslated region (UTR). These inserts also were found to include mTERT intronic sequence (as noted above, the insert was derived from genomic BAC clones).

A RT-PCR product (called mTRT Ra-200) from the cDNA described above was obtained using primers mTRT.35 (from mTRT Ra3') (5'-CTTCCTCAGGACCCTGGTCCGAG-3') (SEQ ID NO:9) and mTRT.27 (from mTRT 495-2A2) (5'-ATTGAGGTCTGGGCATACCTGC-3') (SEQ ID NO:10). This reaction amplified a contaminating DNA encoding a portion of the mTERT gene and a non-coding region.

Another DNA containing the 3' end of the mTERT cDNA was obtained by RT-PCR The primer pair was a 3' primer including the sequence encoding the carboxy-terminus of hTERT cDNA (5'-TCAGCGTCGTCCCCGGGAGCTT-3') (SEQ ID NO:11) and a 5' primer from the above-described upstream mTERT amplification product (mTRT Ra-200) (5'-TCACCCTCTGAGGCTTCGGTGT-3') (SEQ ID NO:12). These two primers were reacted with cDNA from mouse poly A+ RNA. The product of this amplification was subcloned (into plasmid designated mTRT Ra-62) and sequenced. Analysis of the sequence showed that it included the carboxy-terminus encoding portion of the ORF and 3' UTR (from the transcribed, but untranslated cDNA sequence) and intronic sequences.

To construct a DNA spanning from pGRN227 to the 3' UTR, cDNA from mouse testis poly A+ mRNA (Clontech, Palo Alto, Calif.) was amplified using error-free, Pwo DNA polymerase (Boehringer Mannheim, Amersterdam, The Netherlands). cDNA was first made using a 3' oligo-dT primer in a 3' RACE amplification protocol, as generally described above. Subsequently, the primers mTRT.10 (5'-CGTCGATACTGGCAGATGCGG-3') (SEQ ID NO:13) and mTRT.53 (5'-GTGCTGAGGCTACAATGCCCATGT-3') (SEQ ID NO:14) were amplified at 94° C. for 30 min., 68° C. for 3 min., for 30 cycles; followed by 30 more cycles using primers mTRT.9 (5'-CTTTTACATCACAGAGAGCAC-3') (SEQ ID NO:15) and mTRT.52 (5'-CATGTTCATCTAGCGGAAGGAGACA-3') (SEQ ID NO:16). The PCR product (called mTRT Ra-52) was cloned into pCR II (Invitrogen, San Diego,CA), and 5 independent clones were isolated and the mTERT inserts sequenced (called mTRT Ra52). The DNA insert sequence was identical for all 5 clones and matched the sequence of the mTERT PCR amplification products described above, including the entire mTERT open reading frame. A unique NheI restriction site located in the region of the overlap between this RT-PCR product (called mTRT Ra 52.17 or pGRN189) and the 5' mTERT cDNA clone was utilized to construct the full length mTERT ORF. The plasmid with this fill-length ORF was designated pGRN18. The mTERT insert of pGRN188 (SEQ ID NO:1) has been submitted to Genbank as Accession No. AF051911 (and is incorporated by reference herein, as noted below).

FIG. 1 shows the complete sequence of the mTERT cDNA (SEQ ID NO:1). FIG. 2 shows the deduced translation (polypeptide) product (SEQ ID NO:2). FIG. 6 shows a preliminary sequencing of the genomic promoter region of mTERT (SEQ ID NO:4).

Cloning and Sequencing of Genomic mTERT DNA

A lambda phage (called lambda-mTERT1) with an approximately 23 kilobase pair (Kbp) insert containing the ATG initiator for mTERT was cloned from a mouse genomic 129SV phage library (Stratagene, San Diego, Calif.) using a mTERT cDNA probe (residues 1586 to 1970 from SEQ ID NO:1). Two subfragments of lambda-mTERT1 (an 8 Kbp HindIII and a 6 Kbp BglII fragment) were found to hybridize to portions of pGRN227 in a Southern hybridization experiment, see map, FIG. 7. The 8kb HindIII phage DNA fragment was subcloned into the HindIII site of Bluescript KS(+) (Stratagene, San Diego, Calif.) (called B2.18). The 6kb BglII fragment, which begins just downstream of the ATG initiator codon and extends in the 3' direction, was subcloned into the BamHI site of Bluescript KS(+) (called pmTERTgen-BglII). A preliminary DNA sequence of a portion of B2.18 containing the ATG initiator and extending upstream is shown in FIG. 8 (SEQ ID NO:5). Comparison of the genomic sequence (FIG. 8) versus the mTERT cDNA sequence (FIG. 1) indicates a probable 102 bp intron at position 2306 to 2407 (residues as numbered in FIG. 8). A 104 bp intron is in the analogous position in hTERT.

Cloning and Sequencing mTERT Species

The invention provides isolated, purified, and recombinant genes for mTERT, including mTERT alleles, homologues, and isoforms. The invention provides an example of an mTERT nucleic acid and polypeptide species, SEQ ID NO:1 and SEQ ID NO:2, respectively, and describes the structural features common to mTERT species that can be to detect and identify mTERT isoforms, alleles and homologs. The conservation of these intron sites between mouse and human TERTs predicts that the first exon constitutes a functional amino acid domain, the alteration or loss of this domain could effect a change in TERT function. The invention provides nucleic acid and protein reagents encoding or comprising this domain which can be used to restore a TERT function to TERT molecules missing this domain or to provide that function in vitro or in vivo.

mTERT nucleic acid sequence (from cDNA of SEQ ID NO:1) and protein sequence information (SEQ ID NO:2) can be used to prepare PCR primers and oligonucleotides for the identification of telomerase gene(s) and cDNA. PCR primers pairs that can amplify sequences conserved amongst mTERT species are preferred reagents of the invention and are useful to amplify directly new mTERT isoforms, homologues and alleles. Alternatively, such oligonucleotides are useful to detect mTERT-encoding nucleic acid using a variety of hybridization techniques and conditions. These oligonucleotides can be generated using any known technique, including PCR, enzymatic restriction digestion of isolated DNA or organic synthesis. These nucleic acids can be labeled for detection and hybridized to DNA or RNA by any known technique, as described above.

Total RNA can be extracted and enriched for mRNA using the QuickPrep Micro mRNA Purification Kit (Pharmacia, Piscataway, N.J.) according to the manufacturer's instructions. The mRNA can then be used to make cDNA templates by reverse transcription, using, e.g., the avian myeloblastosis virus (AMV) reverse transcriptase (Pharmacia), as described by Sambrook. PCR is performed on the cDNA using, for example, a Techne PHC-3 thermal cycler (Techne, Princeton, N.J.) with any set of primers with sequence complementary or identical to or based on a known mTERT, or other TERT, sequence. PCR can also be used to amplify telomerase sequences from murine genomic DNA. Alternative variations of traditional PCR can be used, such as RACE, as described above. As noted above, PCR amplification can use a variety of annealing conditions. For example, mTERT can be amplified using the following cycling protocol: denaturing at 94° C., 45 seconds; annealing at 60° C., 45 seconds; and extension at 72° C., 90 seconds. This can be repeated for a total of about 30 to 40 cycles, yielding a DNA product, which can be purified. The PCR product can be sequenced by any known technique, such as the dideoxy-chain termination method using a Dye Terminator Cycle Sequencing Kit™ Ready Reaction Kit (Applied Biosystems, Foster City, Calif.) and a Model 373A DNA Sequencer (Applied Biosystems). The PCR product, once identified as an mTERT sequence, can be further labeled and used as a hybridization probe, as described above.

Computer databases and programs can be used to analyze the resultant DNA sequence for its sequence identity, or homology, to known murine and other related TERT sequences, as described above. For example, PC/Gene™ software (IntelliGenetics Inc., Mountain View, Calif.) aligns sequences and displays open reading frames. BLAST N and BLAST D search algorithms can be employed to search the GenBank database (NIH, Bethesda, Md.) for any matches between the derived mTERT sequence and known mTERT and other TERT sequences.

Example 2

RNase Protection Assay for Detection and Quantitation of TERT mRNA

RNase protection assays can be used to detect, monitor, or diagnose the presence of an mTERT mRNA or a variant mRNA. An RNase protection assay is a reliable, sensitive, and quantifiable assay for detection of mTERT RNA. One illustrative RNase protection probe is an in vitro synthesized RNA comprised of sequences complementary to mTERT mRNA sequences and additional, non-complementary sequences. The latter sequences are included to distinguish the full-length probe containing these sequences from a probe that has only complementary sequences. In a positive assay, the complementary sequences of the probe are protected from RNase digestion, because they are hybridized to mTERT mRNA. The non-complementary sequences (single-stranded sequences) are digested away from the probe by the RNase.

The following illustrative example describes an RNase protection assay which can be used to detect and quantify mTERT mRNA. Also, see, e.g., Ma (1996) *Methods* 10:273–278 and Ausubel (1987) supra, chapter 4.7, for general details on RNase protection assay protocols; Kenrick (1997) *Nucleic Acids Res.* 25:2947–2948, describing a method to quantify mRNA levels using RNase protection and scintillation proximity assay technologies, a variety of mTERT protection probes can be designed for use with mouse RNA. The probes can differ in their sequence complementary to mTERT, but each may contain identical non-complementary sequences, i.e., derived from the SV40 late mRNA leader sequence. Probes designed for use in this exemplary RNase protection assay can be chimerical antisense RNA probes. They can comprise the initiator G from the T7 promoter, 32 nucleotides of the SV40 late leader (Chiou (1991) *J. Virol.* 65:6677–6685) and about 150 nucleotides to about 200 or more nucleotides of antisense mTERT. Using T7 RNA polymerase and radioactive guanosine, probes can be labeled to generate probes that are 800,000 cpm/pmol.

To conduct the assay, either probe can be hybridized to RNA, i.e., polyA+ RNA, from a test sample. T1 ribonuclease and RNase a are then added. After RNase digestion, probe RNA is purified and analyzed by gel electrophoresis.

RNAse protection probes can be generated by in vitro transcription using T7 RNA polymerase. Radioactive or otherwise labeled ribonucleotides can be included for synthesis of labeled probes. The templates for the in vitro transcription reaction to produce the RNA probes are PCR products. The illustrative probes described above can be synthesized using T7 polymerase following PCR amplification of mTERT DNA using primers that span the corresponding complementary region of the mTERT gene or mRNA. In addition, the downstream primer contains T7 RNA polymerase promoter sequences and the non-complementary sequences.

RNase protection probes are hybridized to poly a+ RNA, then digested with T1 Ribonuclease and RNase a, as described in Ausubel. The plasmid containing the TERT insert is linearized with restriction endonuclease. Transcription initiated with T7 RNA polymerase yields a runoff transcript. Transcripts are quantified by the inclusion of $^{35}$S UTP in the nucleotide pool (400 cpm/pmol uridine). Protected probes of the correct length are quantified by comparing them with known quantities of an in vitro generated standard.

Example 3

Expression of mTERT in Bacteria, Yeast, Insect and Mammalian Cells

The following example details the design of mTERT-expressing bacterial expression vectors to produce large quantities of full-length, biologically active mTERT (SEQ ID NO:2). Generation of biologically active mTERT in this manner is useful for telomerase enzyme reconstitution assays, assaying for telomerase activity modulators, analysis of the activity of newly isolated species of telomerase, identifying and isolating compounds which specifically associate with telomerase, analysis of the activity of telomerase which has been site-specifically mutated, as described above, to analyze the secondary, tertiary or quaternary structure of mTERT and telomerase enzyme, as by crystallization and diffraction analysis or NMR, and as an immunogen, for example.

pThioHis a/hTERT Bacterial Expression Vector

To produce large quantities of full-length or subfragments of mTERT (SEQ ID NO:2), the bacterial expression vector pThioHis a (Invitrogen, San Diego, Calif.) can be used. In one embodiment, the vector incorporates an mTERT-coding insert including the full-length or partial sequence encoding mTERT (SEQ ID NO:2). This expression vector is designed for inducible expression in bacteria.

The vector can be also induced to express, in *E. coli*, high levels of a fusion protein composed of a cleavable, HIS tagged thioredoxin moiety and the full length or subfragment of the mTERT protein.

pGEX-2TK wth mTERT, with HIS-8 Tag

To produce large quantities of a full length of a fragment of mTERT, another *E. coli* expression vector pGEX-2TK (Pharmacia Biotech, Piscataway N.J.) construct can be used. This construct can contain a subsequence or all of the mTERT coding sequence (SEQ ID NO:1) and a sequence encoding eight consecutive histidine residues (HIS-8 Tag). Vectors with mTERT cDNA Lacking 5'-non-coding Sequence As described above, in one embodiment, the invention provides for an mTERT that is modified in such a site-specific manner to facilitate cloning into bacterial, mammalian, yeast and insect expression vectors without any 5' untranslated mTERT sequence. In some circumstances, minimizing the amount of non-protein encoding sequence allows for improved protein production (yield) and increases mRNA stability. In this embodiment of the invention, the 5' non-coding region is removed before cloning into the bacterial expression vector.

This is effected by engineering an additional restriction endonuclease site just upstream (5') to the start (ATG) codon of mTERT cDNA. The creation of a restriction site just 5' to the coding region of the protein allows for design and production of fusion proteins, including labels and peptide TAGs, for immunodetection and purification.

Plasmids with mTERT cDNA Lacking 3'-non-coding Sequence

As discussed above, the invention provides expression vectors containing TERT-encoding nucleic acids in which some or all non-coding sequences have been deleted. In some circumstances, minimizing the amount of non-protein encoding sequence allows for improved protein production (yield) and increased mRNA stability. In this embodiment, the 3' untranslated region of mTERT is deleted before cloning into the bacterial expression plasmid.

MPSV-mTERT Expression Plasmids

The invention also provides for a method of expressing mTERT in mammalian cells that can give the highest possible expression of recombinant mTERT without actually modifying the coding sequence (e.g. optimizing codon usage). In one embodiment, the invention provides MPSV mammalian expression plasmids (described by Lin J-H (1994) *Gene* 47:287–292) capable of expressing the mTERTs of the invention. The MPSV plasmids can be expressed either as stable or transient clones.

In this expression method, while the mTERT coding sequence (SEQ ID NO:1) itself is unchanged, exogenous transcriptional control elements are incorporated into the vector. The myeloproliferative sarcoma virus (MPSV) LTR (MPSV-LTR) promoter, enhanced by the cytomegalovirus (CMV) enhancer, is incorporated for transcriptional initiation. This promoter consistently shows higher expression levels in cell lines (see Lin J-H (1994) supra), a Kozak consensus sequence can be incorporated for translation initiation (see Kozak (1996) *Mamm. Genome* 7:563–574. All extraneous 5' and 3' untranslated mTERT sequences can be removed to insure that these sequences do not interfere with expression, as discussed above.

The invention also provides for an mTERT "antisense" sequence containing plasmid. This vector is identical to that described above except that the mTERT insert is the antisense sequence of mTERT SEQ ID NO:1.

Two selection markers, PAC (Puromycin-N-acetyl-transferase=Puromycin resistance) and HyB (Hygromycin B=Hygromycin resistance) are present for selection of the plasmids after transfection (see discussion referring to selectable markers, above). Double selection using markers on both sides of the vector polylinker can ensure the stable maintenance of the mTERT coding sequence, a DHFR (dihydrofolate reductase) encoding sequence can be included to allow amplification of the expression cassette after stable clones are made. Other means of gene amplification can also be used to increase recombinant protein yields.

The invention also provides MPSV mammalian expression plasmids containing mTERT fusion proteins. In one embodiment, the mTERT sequence, while retaining its 5' untranslated region, is linked to an epitope flag, such as the IBI FLAG (International Biotechnologies Inc. (IBI), Kodak, New Haven, Conn.) and inserted into the MPSV expression plasmid. This particular construct contains a Kozak translation initiation site. The expressed fusion protein can be purified using the M-1 anti-FLAG octapeptide monoclonal antibody (IBI, Kodak, supra).

Bacterial Expression Vectors Using Antibiotic Selection Markers

The invention also provides bacterial expression vectors that can contain selection markers to confer a selectable phenotype on transformed cells and sequences coding for episomal maintenance and replication such that integration into the host genome is not required. For example, the marker may encode antibiotic resistance, particularly resistance to chloramphenicol (see Harrod (1997) *Nucleic Acids Res.* 25: 1720–1726), kanamycin, G418, bleomycin and hygromycin, to permit selection of those cells transformed with the desired DNA sequences, see for example, Blondelet-Rouault (1997) supra; Mahan (1995) *Proc. Natl. Acad. Sci. USA* 92:669–673. In one embodiment, the full length mTERT (SEQ ID NO:1) is cloned into a modified Bluescript plasmid vector. The mTERT ORF is oriented in the opposite orientation of the Lac promoter. This makes a plasmid that is suitable for mutagenesis of plasmid inserts, such as mTERT nucleic acids of the invention. mTERT can be site-specifically altered, e.g., in motif regions, to create, e.g., dominant negative mTERT mutants, as described above. This plasmid can also be used for in vitro transcription of mTERT using the T7 promoter and in vitro transcription of antisense mTERT using the T3 promoter.

Expression of mTERT Telomerase in Yeast

The invention provides mTERT-expressing yeast expression vectors to produce large quantities of full-length, biologically active mTERT, or fragments thereof including the mTERT polypeptide comprising a sequence as set forth in SEQ ID NO:2.

*Pichia pastoris* Expression Vector

To produce large quantities of full-length, biologically active mTERT (SEQ ID NO:2), or a fragment thereof, the *Picha pastoris* expression vector pPICZ B (Invitrogen, San Diego, Calif.) can be used. The mTERT-coding insert is derived from SEQ ID NO:1. This nucleotide sequence encodes a polypeptide comprising the full-length sequence of mTERT as set forth in SEQ ID NO:2. This expression vector is designed for inducible expression in *P. pastoris* of high levels of full-length, unmodified mTERT protein, or a fragment thereof (SEQ ID NO:2). Expression is driven by a yeast promoter, but the expressed sequence utilizes the mTERT initiation and termination codons. The pPICZ B/hTERT vector (Invitrogen, San Diego, Calif.) is used to transform the yeast.

Expression of mTERT in Insect Cells

The following example details the design of TERT-expressing insect cell expression vectors to produce large quantities of full-length, biologically active TERT, such as mTERT (SEQ ID NO:2), or subfragments thereof.

Baculovirus Expression Vector pBlueBacHis2 B mTERT coding sequence can be cloned into the baculovirus expression vector pVL1393 (Invitrogen, San Diego, Calif.). This construct is subsequently cotransfected into *Spodoptera fungupeida* (sf-9) cells with linearized DNA from Autograph California nuclear polyhidrosis virus (Baculogold-AcMNPV). The recombinant baculoviruses obtained are subsequently plaque purified and expanded following published protocols, as discussed above. This expression vector is designed for expression in insect cells of high levels of full-length mTERT protein, or subfragments thereof. Expression is driven by a baculoviral polyhedrin gene promoter, but the expressed sequence utilizes the mTERT initiation and termination codons.

To produce large quantities of full-length, biologically active mTERT (SEQ ID NO:2), or subfragments thereof, the baculovirus expression vector pBlueBacHis2 B (Invitrogen, San Diego, Calif.) can be used. The mTERT-coding insert can comprise nucleotides as set forth in SEQ ID NO:1. This nucleotide sequence includes the full-length sequence encoding mTERT (SEQ ID NO:2).

Another embodiment provides for a full length mTERT with 6HIS and Anti-Xpress tags. This vector also contains an insert consisting of all or a subsequence of SEQ ID NO:1. The vector directs expression in insect cells of high levels of full length mTERT, or fragments thereof, fused to cleavable 6-histidine and an Anti-Xpress tags with an enterokinase cleavage site.

Baculovirus Expression Vector pBlueBac4.5

To further produce large quantities of full-length, biologically active mTERT (SEQ ID NO:2), or subfragments thereof, a second baculovirus expression vector, pBlueBac4.5 (Invitrogen, San Diego, Calif.) can be used. The mTERT-coding insert can also consist of nucleotides comprising all or a subsequence of SEQ ID NO:1.

Baculovirus Expression Vector pMelBacB

To further produce large quantities of full-length, biologically active mTERT (SEQ ID NO:2), or sub fragments thereof, a third baculovirus expression vector, pMelBacB (Invitrogen, San Diego, Calif.) can be selected. The mTERT-coding insert can also consist of nucleotides comprising all or a subsequence of SEQ ID NO:1.

pMelBacB can direct expression of full length mTERT, or subfragments thereof (SEQ ID NO:2), in insect cells to the extracellular medium through the secretory pathway using the melittin signal sequence. High levels full length mTERT (SEQ ID NO:2) are thus secreted. The melittin signal sequence is cleaved upon excretion, but is part of the protein pool that remains intracellular.

Expression of mTERT in Mammalian Cells

The recombinant mTERT of the invention can be produced in large quantities as full-length, biologically active mTERT, or subfragments thereof (SEQ ID NO:2), in a variety of mammalian cell lines.

mTERT Expressed in 293 Cells using Episomal Vector pEBVHis

In one embodiment, an episomal vector, pEBVHis (Invitrogen, San Diego, Calif.) engineered to express an mTERT (SEQ ID NO:2) fusion protein comprising mTERT fused to an N-terminal extension epitope tag, the Xpress epitope (Invitrogen, San Diego, Calif.). The mTERT open reading frame (ORF) is cloned so that the mTERT ORF, or subfragments thereof, are in the same orientation as the Rous Sarcoma virus (RSV) promoter. In this orientation, the His6 flag is relatively closer to the N-terminus of mTERT, a control vector can also be constructed to contain as an insert the antisense sequence of the fusion protein (mTERT and the epitope tag), for co-transfection, to be used as a negative control.

The vectors are transfected into mammalian cells, and translated mTERT is identified and isolated using an antibody specific for the Xpress epitope. pEBVHis is a hygromycin resistant EBV episomal vector that expresses the protein of interest fused to an N-terminal peptide. Cells carrying the vector are selected and expanded, then nuclear and cytoplasmic extracts prepared. These and control extracts are immunoprecipitated with anti-Xpress antibody, and the immunoprecipitated beads are tested for mTERT and/or telomerase enzyme expression and activity by the various assays described above.

Expression of Recombinant mTERT in Mortal, Normal Diploid Human or Mouse Cells

In one embodiment of the invention, recombinant mTERT and necessary telomerase enzyme complex components can be expressed in normal, diploid mortal cells to create an indefinitely proliferating cell line, to directly immortalize the cells, or to facilitate immortalizing them. This allows one to obtain diploid immortal cells with an otherwise normal phenotype and karyotype.

Sense mTERT (SEQ ID NO:1) and antisense mTERT (complementary to SEQ ID NO:1) are cloned into a CMV vector. These vectors are purified and transiently transfected into two normal, mortal, diploid mammalian cell clones. Analysis of telomerase enzyme activity can be done using a TRAP assay, as described above, e.g., utilizing the TRAPezc Kit (Oncor, Inc., Gaithersburg, Md.). Transfection of sense mTERT—but not antisense mTERT—generates telomerase enzyme activity.

Vectors for Regulated Expression of mTERT in Mammalian Cells: Inducible and Repressible Expression of mTERT The invention provides vectors which can be manipulated to induce or repress the expression of the mTERT of the invention. For example, mTERT (SEQ ID NO:1) is cloned into the Ecdysone-Inducible Expression System from Invitrogen (San Diego, Calif.) and the Tet-On and Tet-off tetracycline regulated systems from Clontech Laboratories, Inc. (Palo Alto, Calif.). Such inducible expression systems are provided for use in the methods of the invention where it is important to control the level or rate of transcription of transfected mTERT. For example, the invention provides cell lines made indefinitely proliferating or immortalized through the expression of mTERT; such cells can be rendered "mortal" by inhibition of mTERT expression by the vector through its transcriptional controls, such as the Tet-Off system. The invention also provides methods of expressing mTERT only transiently to avoid the constitutive expression of mTERT, which may lead to unwanted "immortalization" of transfected cells, as discussed above.

The Ecdysone-Inducible Mammalian Expression System is designed to allow regulated expression of the gene of interest, such as mTERT, in mammalian cells. The system is distinguished by its tight regulation that allows almost no detectable basal expression and greater than 200-fold inducibility in mammalian cells. The expression system is based on the heterodimeric ecdysone receptor of Drosophila. The Ecdysone-Inducible Expression System uses a steroid hormone ecdysone analog, muristerone a, to activate expression of mTERT via a heterodimeric nuclear receptor. Expression levels have been reported to exceed 200-fold over basal levels with no effect on mammalian cell physiology (No (1996) "Ecdysone-Inducible Gene Expression in Mammalian Cells and Transgenic Mice" Proc. Natl. Acad. Sci. USA 93, 3346–3351). Once the receptor binds ecdysone or muristerone, an analog of ecdysone, the receptor activates an ecdysone-responsive promoter to give controlled expression of the gene of interest, as mTERT. In the Ecdysone-Inducible Mammalian Expression System, both monomers of the heterodimeric receptor are constitutively expressed from the same vector, pVgRXR. The ecdysone-responsive promoter, which ultimately drives expression of the gene of interest, is located on a second vector, pIND, which drives the transcription of the gene of interest. In one embodiment, mTERT is cloned in the pIND vector (Clontech Laboratories, Inc, Palo Alto, Calif.) containing five modified ecdysone response elements (E/GREs) upstream of a minimal heat shock promoter and the multiple cloning site. The construct is then transfected in cell lines which have been pre-engineered to stably express the ecdysone receptor. After transfection, cells are treated with muristerone a to induce intracellular expression of the gene of interest from pIND.

The Tet-on and Tet-off expression systems (Clontech, Palo Alto, Calif.) give access to the regulated, high-level gene expression systems described by Gossen (1992) "Tight control of gene expression in mammalian cells by tetracycline responsive promoters" Proc. Natl. Acad. Sci. USA 89:5547–5551, for the Tet-Off transcription repression system; and Gossen (1995) "Transcriptional activation by tetracycline in mammalian cells" Science 268:1766–1769, for the Tet-On inducible transcriptional system. In "Tet-Off" transformed cell lines, gene expression is turned on when tetracycline (Tc) or doxycycline ("Dox;" a Tc derivative) is removed from the culture medium. In contrast, expression is turned on in Tet-On cell lines by the addition of Tc or Dox to the medium. Both methods permit expression of cloned genes to be regulated closely in response to varying concentrations of Tc or Dox. This method uses the "pTRE" as a response plasmid that can be used to express a gene of interest, such as mTERT. pTRE contains a multiple cloning site (MCS) immediately downstream of the Tet-responsive PhCMV*–1 promoter. cDNAs or genes of interest inserted into one of the sites in the MCS will be responsive to the tTA and rtTA regulatory proteins in the Tet-Off and Tet-On systems, respectively. PhCMV*–1 contains the Tet-responsive element (TRE), which consists of seven copies of the 42-bp tet operator sequence (tetO). The TRE element is just upstream of the minimal CMV promoter (PminCMV), which lacks the enhancer that is part of the complete CMV promoter in the pTet plasmids. Consequently, PhCMV*–1 is silent in the absence of binding of regulatory proteins to the tetO sequences. The cloned insert must have an initiation codon. In some cases, addition of a Kozak consensus ribosome binding site may improve expression levels; however, many cDNAs have been efficiently expressed in Tet systems without the addition of a Kozak sequence. pTRE-Gene X plasmids are cotransfected with pTK-Hyg to permit selection of stable transfectants.

Setting up a Tet-Off or Tet-On expression system generally requires two consecutive stable transfections to create a "double-stable" cell line that contains integrated copies of genes encoding the appropriate regulatory protein and TERT under the control of a tet-responsive element (TRE). In the first transfection, the appropriate regulatory protein is introduced into the cell line of choice by transfection of a "regulator plasmid" such as pTet-Off or pTet-On vector, which express the appropriate regulatory proteins. mTERT cloned in the pTRE "response plasmid" is then introduced in the second transfection to create the double-stable Tet-Off or Tet-On cell line. Both methods give very tight on/off control of gene expression, regulated dose-dependent induction, and high absolute levels of gene expression.

Expression of Recombinant mTERT with DHFR and Adenovirus Sequences

In one embodiment, a plasmid construct is prepared for transient expression of mTERT cDNA in mammalian cells, a Kozak consensus is inserted at the 5' end of mTERT coding sequence. The mTERT insert can be designed to contain no 3' or 5' UTR. The mTERT cDNA is inserted into the EcoRI site of p91023(B) (Wong (1985) Science 228:810–815). The mTERT insert is in the same orientation as the DHFR ORF. The expression vector is useful for transient expression.

The selected plasmid contains an SV40 origin and enhancer just upstream of an adenovirus promoter, a tetracycline resistance gene, an E. coli origin and an adenovirus VAI and VAII gene region. This expression cassette contains, in the following order: the adenovirus major late promoter, the adenovirus tripartite leader, a hybrid intron consisting of a 5' splice site from the first exon of the tripartite leader and a 3' splice site from the mouse immunoglobulin gene; the mTERT cDNA; the mouse DHFR coding sequence; and the SV40 polyadenylation signal.

The adenovirus tripartite leader and the VA RNAs have been reported to increase the efficiency with which polycistronic mRNAs are translated. DHFR sequences have been reported to enhance the stability of hybrid mRNA. DHFR sequences also can provide a marker for selection and amplification of vector sequences. See Logan (1984) Proc. Natl. Acad. Sci. USA 81:3655); Kaufman (1985) Proc. Natl. Acad. Sci. USA 82: 689; and Kaufman (1988) Focus (Life Technologies, Inc.) Vol. 10, no. 3).

Example 4 mTERT Transgenic Mice and mTERT "Knock Out" Mice

The invention provides transgenic cells and animals which can express an introduced recombinant mTERT. The recombinant mTERT can be wild-type (native) or modified. An exogenous mTERT endogenous mTERT can remain function. The methods of the invention include screening for mTERT modulators in animals by reconstituting an mTERT and/or murine telomerase enzyme in an animal, e.g., a transgenic animal.

The in vivo assays methods include "knockout" models, in which one or several units of the endogenous telomerase, telomerase RNA moiety and/or telomerase-associated proteins have first been deleted or inhibited before an exogenous murine telomerase activity (full or partial) is reconstituted. The transgenic animals of the invention also provide methods of expressing the mTERT and murine telomerase compositions of the invention and providing indefinitely proliferating and immortalized, otherwise normal cells which can be used to express compositions of interest.

The mTERT gene can be "knocked out" using conventional techniques, usually involving homologous recombination, as discussed above. Thus, the invention provides for a unique targeting vector comprising the mTERT nucleic acid sequences of the invention, including at least part of SEQ ID NO:1, for use in homologous recombination to create a mouse that cannot express its endogenous mTERT. The targeting vector is usually inserted in a pluripotential embryonic cell or cell line, such as mouse embryonic stem (ES) cells, to disrupt the complementary endogenous gene by homologous recombination. Animals with the targeted and disrupted gene of interest, lacking or having impaired ability to express that gene, are bred.

Means of constructing such vectors, inserting them into the cells of interest, breeding animals, and the like, to construct these "knock-out" animals are described herein, and generally well described in the scientific and patent literature, see also, e.g., U.S. Ser. No. 08/623,166, filed 28 Mar. 1996, describing construction of hTERC (hTR) knockout mice. See also, e.g., for further illustrative examples of construction of "knockout mice," Ma (1997) J. Clin. Invest. 100:957–962; Schwindinger (1997) Endocrinology 138:4058–4063; Stenbit (1997) Nat. Med. 3:1096–1101; Moreadith (1997) J. Mol. Med. 75:208–216; Udy (1997) Exp. Cell Res. 231:296301, describing use of isogenic lines to support homologous recombination events; Taghian (1997) Mol. Cell. Biol. 17:638&6393, on use of chromosomal double-strand breaks to induce gene conversion, chromosomal and extrachromosomal recombination, and gene targeting at high frequency in mammalian cells; Templeton (1997) Gene Ther. 4:700–709, for methods to improve the efficiency of gene correction in mouse embryonic stem cells using homologous recombination; Araki (1997) Nucleic Acids Res. 25:868–872; describing targeted, site-directed integration of DNA using mutant lox sites in embryonic stem cells; and, Kühn (1997) Curr. Opin. Immunol. 9:183–188, describing methods for site-specific and homologous DNA recombination expanding the potential of gene targeting in embryonic stem cells.

Plasmid Construction and Production of Transgenic Mice

The construction and use of transgenic mice that express introduced mTERT, hTERT, or TERT genes is described below.

EcoRI cDNA fragments containing the full length ORF for mTERT (from pGRN188), hTERT (from pGRN121), and hTERT-D868A (from pGRN202) were ligated into the pCAGGS expression vector containing the chicken beta-actin promoter, cytomegalovirus enhancer element, beta-actin intron and bovine globin poly-adenylation signal (Niwa (1991) Gene 108:193–199). The entirety of each insert with promoter, coding, and polyadenylation sequences were liberated with HinDIII and SalI restriction digests, gel purified, and then injected into C57 BL/6×FVB fertilized eggs (general procedure described in Morgenbesser (1995) EMBO J. 14:743–746). The DNA injected eggs were then transplanted to pseudopregnant female mice resulting in 26 newborns. Incorporation of the transgene was identified by Southern and slot blot analysis using mTERT cDNA fragment probes. Three transgene positive founder lines were identified.

Construction of mTERT Gene Knockout Mice

The construction of a transgenic mouse line homozygous for an mTERT deletion is described below, this mouse line is also called a "knockout" mouse line in that it is missing functional copies of both mTERT alleles (the invention also provides for mice in which mTERT expression is modified, or in which only one allele of mTERT is deleted or modified, as discussed above). The mTERT –/– mouse knockout line can be used to assess mTERT, hTERT, telomerase, and telomere maintenance and function in vivo or ex vivo. Mutated or deleted forms of TERT genes can be also introduced into the mTERT –/– cells or mice to create new transgenic mice or cells that can assess the functional consequences of the alterations. In this manner functional domains of TERT can be identified and their functions assigned. The restoration or loss of functions associated with TERT alterations could identify TERT- or telomerase-interacting proteins.

In another embodiment, the mTERT −/− mice are used to assess in vivo or ex vivo effects of telomerase inhibitory compounds on animals, tissues and cells in the absence of telomerase enzyme activity. This is a useful biological model method to assess the pharmacokinetics and potential for adverse side effects of telomerase enzyme modulators (e.g., mTERT inhibitory compounds). Transgenic knockout mTERT −/− lines with introduced mutant TERTs could be used to assess the in vivo or ex vivo mode of action of telomerase enzyme modulating compounds and to improve their agonist, inhibitory or interaction properties.

The invention also provides cells and mouse lines in which a recombinant TERT gene with alterations to a transcriptional regulatory region (e.g., the promoter or other region) in place of a TERT genomic sequence (e.g., optionally mTERT or hTERT) is reintroduced into the mTERT −/− mice to assess cis-acting (e.g., promoter) or other regulatory regions. These mouse lines can also be used to assess the biological consequences of regulatory region alterations or the inappropriate expression of the introduced TERT under the control of the modified regulatory region. These methods can also be used to assess, alter, or improve the in vivo or ex vivo actions of TERT affecting trans-activating transcriptional regulatory agents. Such a method can modulate the expression of the TERT promoter in order to, e.g., assert a therapeutic effect.

Figure 9:
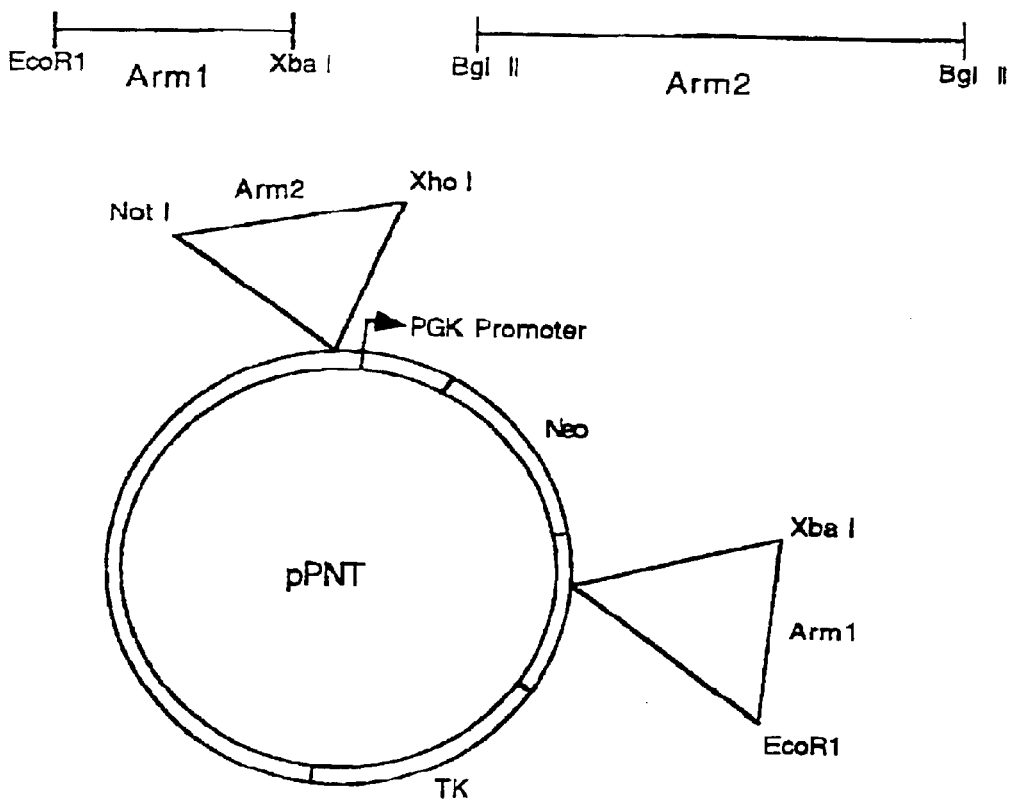
FIG. 9 presents a schematic illustration of the mouse gene "knockout" targeting construct pmTERTKO.

The mouse mTERT 5' genomic region described above was isolated by screening a 129/Sv mouse genomic library (Stratagene, San Diego, Calif.) with a fragment spanning nucleotides 1585–1970 of the mTERT cDNA (SEQ ID NO:1). The targeting construct, pmTERTKO, utilized the mutant neomycin-resistance and HSV thymidine kinase genes under the control of the PKG promoter, and was constructed as generally described in Serrano (1996) *Cell* 85:27–37. FIG. 9 presents a schematic illustration of the targeting construct (vector) pmTERTKO.

To construct the targeting construct (vector) an approximately 2.8 Kbp EcoRI to XbaI fragment of B2.18 (discussed above), designated Arm1, was ligated into pPNT (described by Serrano (1996) supra) downstream of the Neo gene and upstream of the thymidine kinase gene (FIG. 9). The 6 Kbp BglII fragment, designated Arm2 (FIG. 9), was excised from pmTERTgen-BglII with NotI and XhoI and ligated into these sites in pPNT upstream of the Neo gene.

The pmTERTKO vector was linearized by NotI prior to being electroporated into WW6 ES cells (Ioffe (1995) *Proc. Natl. Acad. Sci. USA* 144:500–510). Homologous recombination of the targeting construct pmTERTKO into the mTERT gene results in replacement of approximately 600 base pairs (bp) of the mTERT genomic sequence encompassing the ORF initiating methionine by the construct's neomycin resistance gene.

Upon transfection into the mouse ES cells and homologous recombination of the construct, the initiator methionine of mTERT was replaced by a portion of the pmTERTKO vector sequence, resulting in a "null" or "knocked-out" allele construct. Clones in which homologous recombination has occurred are selected for with G418 (150 mg/ml active component) and 2 mM gancyclovir. mTERT heterozygous ES clones were identified by Southern blot analysis for the presence of integrated pmTERTKO vector sequence (the null allele). Positive clones were subsequently injected into C57BL/6 blastocysts. Resultant male chimeras with greater than 50% ES contribution, as judged by coat color, were mated with C57BL/6 females. Germline transmission to agouti offspring was confirmed by both Southern blot and PCR analysis of tail DNA for the presence of the integrated vector sequence (the null allele).

The utility of a mTERT knockout mouse line results from the loss or modification of telomerase activity associated with the gene deletions or modifications. Homozygous deletion knockout mice and progeny will have no telomerase activity since no functional mTERT protein will be produced. The telomeres of these homozygous mTERT-mice will progressively shorten, placing an upper limit on the replicative lifespan of its cells, dependent on their telomere length and telomere shortening rate. As observed with the mTERC (mTR) knockout mice (Blasco (1997) *Cell* 91:25–34) the first generation mice will be fertile. Subsequent generations will have shorter and shorter telomeres. Eventually the progressive shortening will result in functional impairment of chromosomes, leading to infertility. Impairment of tissues with high proliferative capacity to replace their cells through cell division is also seen. The rate of telomere shortening in mTERC −/− mice (lacking telomerase enzyme activity) resulted in fertility and cell replacement problems in 4 to 6 generations. mTERT −/− mice, also lacking telomerase enzyme activity, will also have similar defects. The mTERT −/− mice are distinguishable from mTERC −/− mice in that mTERC −/− mice retain the ability to express a potentially active mTERT protein which can interact with telomere proteins, chromosomal structures, other nucleic acid moieties, regulatory proteins, and the like. Thus, even in the absence of mTERC, mTERT can modulate telomere structure and function outside of its telomere addition function. Loss of these functions in the mTERT −/− mice could, in some circumstances, lead to more rapid telomere loss, altered telomere or chromosome function, altered cell cycle regulation, and the like. This could lead to the inviability of the first generation of mTERT −/− mice, a more rapid occurrence of the phenotypes observed in the mTR −/− mice, or new phenotypes.

In one embodiment, the mTERT −/− mice are mated with the mTR −/− mice to create a double knockout line missing both mTERT protein and the mouse telomerase RNA, mTERC. This is a mouse line or cell line with a "clean" background useful for the simultaneous assessment of TERT and telomerase RNA functions. Altered mTERTs, hTERTs, mTERCs, and hTERCs are introduced to assess the functional in vivo and ex vivo affects of the alterations. These lines are particularly useful for assessing the structure and function of hTERT and hTERC since a similar in vivo or ex vivo model method in humans or human cells is technically difficult or ethically impossible. Regions of TERT and TERC interactions can be identified and assigned functions. These lines also provide means to determine how telomerase or TERT modulators affect hTERT and hTERC in vivo. The method is used to improve the telomerase modulatory (e.g., inhibitory) properties of compounds affecting human telomerase. The method can also be used to assess, and reduce, unwanted or secondary (side) effects of modulatory compounds in the context of a whole animal.

Example 5

Antibodies Directed to mTERT and Mouse Telomerase

The antibodies of the invention can be used in several embodiments of the invention as described above, including, e.g.: the isolation of mTERT, murine telomerase enzyme, telomerase-associated proteins; inhibition of telomerase activity by binding to telomerase; identifying the location of telomerase in situ.

mTERT protein fragments to be used as immunogens are generated using expression vectors, typically bacterial expression vectors. Specifically, in one embodiment, an *E. coli* expression vector pGEX-2TK (Pharmacia Biotech, Piscataway N.J.) construct is used containing various subfragments of mTERT-encoding nucleic acid sequences (cDNA, SEQ ID NO:1). The isolated or purified fusion proteins are used in conventional protocols, as described above, to generate rabbit polyclonal antisera and mouse polyclonal antisera and monoclonal antibodies, or to screen phage display libraries, as discussed above.

Example 6 mTERT Telomerase Promoter Expression Constructs

The present invention also provides methods and reagents relating to cis-acting transcriptional and translational mTERT regulatory elements. Examples of cis-acting transcriptional regulatory elements include promoters and enhancers of the mTERT gene. The identification and isolation of cis- and trans-acting regulatory agents provide further methods and reagents for identifying additional agents that modulate transcription and translation of mTERT.

The present invention also provides recombinant vectors in which an mTERT promoter is operably linked to a reporter gene. Such constructs are useful, inter alia, in screens to find agents that modulate the activity of the promoter of the TERT gene. In one illustrative embodiment, the reporter gene is alkaline phosphatase and is derived from the well known pSEAP2 reporter gene system (marketed by Clontech, Palo Alto, Calif.). In one embodiment, to assess the ability of the mTERT promoter to drive transcription, the mTERT promoter is fused to the coding sequence of the human secreted alkaline phosphatase (SEAP).

SEAP is a secreted form of human placental alkaline phosphatase (Berger (1988) "Secreted placental alkaline phosphatase: a powerful new quantitative indicator of gene expression in eukaryotic cells" *Gene* 66: 1–10; Bronstein (1996) *Clin. Chem.* 42:1542–1546). This fusion protein-expressing construct can be inserted into any mammalian expression vector for transient transfection into cells. The SEAP reporter gene encodes a truncated form of the placental enzyme which lacks the membrane anchoring domain, thereby allowing the protein to be secreted efficiently from transfected cells. Levels of SEAP activity detected in the culture medium have been shown to be directly proportional to changes in intracellular concentrations of SEAP mRNA and protein (Berger (1988) *Gene*, supra; Cullen (1992) "Secreted placental alkaline phosphatase as a eukaryotic reporter gene" *Methods Enzymol.* 216:362–368). Thus, there is a direct correlation between levels of SEAP secreted and the activity of the mTERT promoter using such constructs of the invention.

Other embodiments include additional mTERT promoter/reporter protein constructs to evaluate mTERT promoter activity in different cells under varying conditions. Such reporter proteins include, e.g., firefly luciferase, beta-glucuronidase, beta-galactosidase, cloramphenicol acetyl-transferase, and GFP.

Example 7

In Vitro Reconstitution of Telomerase Activity with mTERT

To demonstrate that mTERT cDNA (SEQ ID NO:1) encodes mTERT catalytic activity, in vitro telomerase enzyme reconstitution assays can be performed, as described, e.g., by Weinrich (1997) supra. mTERT was expressed alone or in combination with hTERC, i.e., the mTERT-containing telomerase enzyme was reconstituted using hTERC as the RNA moiety. Resultant telomerase activity was measured by a modified version of the TRAP assay, as described by Kim (1994) supra. As a positive control, parallel assays were performed with hTERT and hTERC. An RNase sensitive 6 bp ladder was generated by mTERT in the presence of hTERC, but not in its absence, indicating that the recombinant mTERT was transcribed and translated, and telomerase enzyme activity was reconstituted, and an RNA moiety was necessary for reconstitution of telomerase enzymatic activity.

TRAP activity was not seen with the mTERT mutant, mTERTDT, which lacks the telomerase specific T motif. These in vitro reconstitution studies demonstrate that the mTERT cDNA encodes telomerase RNA-dependent catalytic activity and, similar to the human enzyme, the presence of the T motif is essential for enzymatic catalysis.

These studies also demonstrate that mTERT and hTERC can form a functional ribonucleoprotein complex despite species differences in the telomerase enzyme RNA moieties, including a longer template for hTERC (see Feng (1995) *Science* 269:1236–41; Blasco (1995) *Science* 269:1267–70). This result suggests that, within the context of this in vitro assay, these primary nucleotide sequence differences in these telomerase RNA moieties do not impact on higher order RNA structure and mTERT protein-RNA interactions.

Example 8

Dominant-negative Mutations of mTERT

This example describes three mutants of mTERT which are predicted to be deficient in a telomerase activity. These mutations change amino acids in the conserved RT motifs previously shown to be essential for RT function (Lingner (1997) supra). The mutations are created using the procedures described in Weinrich (1997) supra.

Four point mutants are generated in mTERT using pGRN190 as the mutagenesis vector. Plasmid pGRN190 is a mammalian expression vector comprising the entire cDNA insert from pGRN188, such that mTERT mRNA is transcribed from the MPSV (myeloproliferative sarcoma virus) promoter. The construction of pGRN190 was similar to that used to construct plasmid pGRN145, described by Bodner, et al., *Science*, January 1998, vol. 279:349–352.

Mutants (1) to (3) are predicted to be deficient in a telomerase enzyme activity. Oligonucleotide (oligo) sequences for generating these point mutants are listed below with the position (based on SEQ ID NO:1 residue numbering) and restriction enzyme sites generated indicated in standard form:

(1) mF550A (5'-ACAGCTGCTTAGATCTTTCGCTTACATCACAGA-3') (SEQ ID NO:17). This oligo generates a point mutation that changes the second phenylalanine in motif T to an alanine (analogous to the F651A in hTERT). This mutation is predicted to greatly or completely reduce a telomerase activity. A BglII restriction site is also introduced.

(2) mD701A (5'-TTGTTAAGGCAGCTGTGACCGGTGCCTATGATGCC-3') (SEQ ID NO:18). This oligo generates a point mutation that changes the aspartate to an alanine in motif A (analogous to the D712A in hTERT). This mutation is predicted to greatly or completely reduce a telomerase activity. PvuII and AgeI restriction sites are also introduced.

(3) mD860A (5'-TACGTTTTGTTGCTGACTTTCTACTAGTGACGCCTCAC-3') (SEQ ID NO:19). This oligo generates a point mutation that changes the aspartate to an alanine in motif C (analogous to the D868A in hTERT). This mutation is predicted to greatly or completely reduce a telomerase activity. A SpeI restriction site is also introduced.

(4) mD600A (5'-GGCATCACCAGGCCACGTGGCTGGCCATGCCCATC-3') (SEQ ID NO:20). This oligo generates a point mutation that changes an aspartate to an alanine upstream of motif 1. This aspartate residue is not conserved between mTERT and hTERT making a good control base change. No or little phenotypic result is expected. A PmlI restriction site is also introduced and a NheI restriction site is deleted.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and GenBank sequences cited herein are hereby incorporated by reference for all purposes.

What is claimed is:

1. An isolated, purified or recombinant polynucleotide encoding a telomerase reverse transcriptase protein, wherein said protein:

(i) has at least 90% sequence identity to SEQ. ID NO:2;

(ii) has telomerase catalytic activity when associated with telomerase RNA component; and (iii) contains at least one of the following amino acid motifs;

Motif T: $W-X_{12}-FFY-X_1-TE-X_{11}-R-X_3-W$;
   Motif 1: $LR-X_1-IPK$;
   Motif 2: $R-X_1-I-X_{15}-K$;
   Motif A: $P-X_3-F-X_3-D-X_4-YD$;
   Motif B: $Y-X_4-G-X_2-QG-X_3-S$;
   Motif C: $DD-X_1-L$; or
   Motif D: $A-X_2-F-X_{18}-K$;

wherein $X_n$ is a sequence of unspecified amino acids of length "n".

2. An isolated, purified or recombinant polynucleotide encoding a telomerase reverse transcriptase protein having the amino acid sequence of SEQ. ID NO:2.

3. An isolated, purified or recombinant polynucleotide comprising the sequence of SEQ. ID NO:1, or fragment thereof that encodes a protein having telomerase activity when associated with telomerase RNA component; wherein the protein contains at least one of the following amino acid motifs;

Motif T: $W-X_{12}-FFY-X_1-TE-X_{11}-R-X_3-W$;
   Motif 1: $LR-X_1-IPK$;
   Motif 2: $R-X_1-I-X_{15}-K$;
   Motif A: $P-X_3-F-X_3-D-X_4-YD$;
   Motif B: $Y-X_4-G-X_2-QG-X_3-S$;
   Motif C: $DD-X_1-L$; or
   Motif D: $A-X_2-F-X_{18}-K$;

wherein $X_n$ is a sequence of unspecified amino acids of length "n".

4. An isolated cell transfected with the polynucleotide of claim 1, or progeny thereof.

5. An isolated cell transfected with the polynucleotide of claim 2, or progeny thereof.

6. An isolated cell transfected with the polynucleotide of claim 3, or progeny thereof.

7. An expression vector comprising the polynucleotide of claim 1.

8. An expression vector comprising the polynucleotide of claim 2.

9. The polynucleotide of claim 1, encoding a protein that is between about 50 and 150 kDa.

10. The polynucleotide of claim 1, encoding a protein that contains Motif T.

11. The polynucleotide of claim 1, encoding a protein that contains Motif 1 and Motif 2.

12. The polynucleotide of claim 1, encoding a protein that contains Motif A, Motif B, Motif C, and Motif D.

13. The polynucleotide of claim 1, encoding a protein that contains at least two of said motifs.

14. The polynucleotide of claim 1, encoding a protein that contains at least four of said motifs.

15. The polynucleotide of claim 1, encoding a protein that contains all of said motifs.

16. The polynucleotide of claim 15, wherein the motifs occur in the order indicated in claim 1.

17. The polynucleotide of claim 1, which hybridizes to a nucleic acid having the mTERT cDNA sequence in SEQ ID NO:1 at 5° C. below $T_m$ in 1 M sodium ion concentration, wherein $T_m$ is the melting temperature under the same conditions of said nuleic acid hybridized to a complementary polynucleotide.

18. An isolated, purified or recombinant polynucleotide encoding a protein that contains SEQ. ID NO:2, or a fragment thereof that has telomerase reverse transcriptase activity when associated with telomerase RNA component.

19. A method of producing a telomerase protein, comprising expressing the polynucleotide of claim 1 in a host cell.

20. A method of producing a telomerase protein, comprising expressing the polynucleotide of claim 17 in a host cell.

21. A method of producing a telomerase protein, comprising expressing the polynucleotide of claim 18 in a host cell.

* * * * *

SEQUENCE LISTING (1) GENERAL INFORMATION:

(iii) NUMBER OF SEQUENCES: 101

(2) INFORMATION FOR SEQ ID NO:1:

(i) SEQUENCE CHARACTERISTICS:
      (A) LENGTH: 3496 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: -
      (B) LOCATION: 1..3496
      (D) OTHER INFORMATION: /note= "mouse telomerase reverse
         trascriptase (mTRT) cDNA clone"

(ix) FEATURE:
      (A) NAME/KEY: misc_feature
      (B) LOCATION: 10..3435
      (D) OTHER INFORMATION: /note= "mouse telomerase reverse
         transcriptase (mTRT) cDNA"

(ix) FEATURE:
      (A) NAME/KEY: CDS
      (B) LOCATION: 39..3404
      (D) OTHER INFORMATION: /product= "mouse telomerase reverse
         transcriptase (mTRT)"

(xi) SEQUENCE DESCRIPTION: SEQ ID NO:1:

```
GAATTCCGGG TGGGAGGCCC ATCCCGGCCT TGAGCACA ATG ACC CGC GCT CCT             53
                                          Met Thr Arg Ala Pro
                                            1               5

CGT TGC CCC GCG GTG CGC TCT CTG CTG CGC AGC CGA TAC CGG GAG GTG          101
Arg Cys Pro Ala Val Arg Ser Leu Leu Arg Ser Arg Tyr Arg Glu Val
                  10                  15                  20

TGG CCG CTG GCA ACC TTT GTG CGG CGC CTG GGG CCC GAG GGC AGG CGG          149
Trp Pro Leu Ala Thr Phe Val Arg Arg Leu Gly Pro Glu Gly Arg Arg
              25                  30                  35

CTT GTG CAA CCC GGG GAC CCG AAG ATC TAC CGC ACT TTG GTT GCC CAA          197
Leu Val Gln Pro Gly Asp Pro Lys Ile Tyr Arg Thr Leu Val Ala Gln
          40                  45                  50

TGC CTA GTG TGC ATG CAC TGG GGC TCA CAG CCT CCA CCT GCC GAC CTT          245
Cys Leu Val Cys Met His Trp Gly Ser Gln Pro Pro Pro Ala Asp Leu
      55                  60                  65

TCC TTC CAC CAG GTG TCA TCC CTG AAA GAG CTG GTG GCC AGG GTT GTG          293
Ser Phe His Gln Val Ser Ser Leu Lys Glu Leu Val Ala Arg Val Val
  70                  75                  80                  85

CAG AGA CTC TGC GAG CGC AAC GAG AGA AAC GTG CTG GCT TTT GGC TTT          341
```

```
                                                          -continued

Gln Arg Leu Cys Glu Arg Asn Glu Arg Asn Val Leu Ala Phe Gly Phe
             90                  95                 100

GAG CTG CTT AAC GAG GCC AGA GGC GGG CCT CCC ATG GCC TTC ACT AGT         389
Glu Leu Leu Asn Glu Ala Arg Gly Gly Pro Pro Met Ala Phe Thr Ser
            105                 110                 115

AGC GTG CGT AGC TAC TTG CCC AAC ACT GTT ATT GAG ACC CTG CGT GTC         437
Ser Val Arg Ser Tyr Leu Pro Asn Thr Val Ile Glu Thr Leu Arg Val
            120                 125                 130

AGT GGT GCA TGG ATG CTA CTG TTG AGC CGA GTG GGC GAC GAC CTG CTG         485
Ser Gly Ala Trp Met Leu Leu Leu Ser Arg Val Gly Asp Asp Leu Leu
            135                 140                 145

GTC TAC CTG CTG GCA CAC TGT GCT CTT TAT CTT CTG GTG CCC CCC AGC         533
Val Tyr Leu Leu Ala His Cys Ala Leu Tyr Leu Leu Val Pro Pro Ser
150                 155                 160                 165

TGT GCC TAC CAG GTG TGT GGG TCT CCC CTG TAC CAA ATT TGT GCC ACC         581
Cys Ala Tyr Gln Val Cys Gly Ser Pro Leu Tyr Gln Ile Cys Ala Thr
                170                 175                 180

ACG GAT ATC TGG CCC TCT GTG TCC GCT AGT TAC AGG CCC ACC CGA CCC         629
Thr Asp Ile Trp Pro Ser Val Ser Ala Ser Tyr Arg Pro Thr Arg Pro
            185                 190                 195

GTG GGC AGG AAT TTC ACT AAC CTT AGG TTC TTA CAA CAG ATC AAG AGC         677
Val Gly Arg Asn Phe Thr Asn Leu Arg Phe Leu Gln Gln Ile Lys Ser
            200                 205                 210

AGT AGT CGC CAG GAA GCA CCG AAA CCC CTG GCC TTG CCA TCT CGA GGT         725
Ser Ser Arg Gln Glu Ala Pro Lys Pro Leu Ala Leu Pro Ser Arg Gly
            215                 220                 225

ACA AAG AGG CAT CTG AGT CTC ACC AGT ACA AGT GTG CCT TCA GCT AAG         773
Thr Lys Arg His Leu Ser Leu Thr Ser Thr Ser Val Pro Ser Ala Lys
230                 235                 240                 245

AAG GCC AGA TGC TAT CCT GTC CCG AGA GTG GAG GAG GGA CCC CAC AGG         821
Lys Ala Arg Cys Tyr Pro Val Pro Arg Val Glu Glu Gly Pro His Arg
                250                 255                 260

CAG GTG CTA CCA ACC CCA TCA GGC AAA TCA TGG GTG CCA AGT CCT GCT         869
Gln Val Leu Pro Thr Pro Ser Gly Lys Ser Trp Val Pro Ser Pro Ala
            265                 270                 275

CGG TCC CCC GAG GTG CCT ACT GCA GAG AAA GAT TTG TCT TCT AAA GGA         917
Arg Ser Pro Glu Val Pro Thr Ala Glu Lys Asp Leu Ser Ser Lys Gly
            280                 285                 290

AAG GTG TCT GAC CTG AGT CTC TCT GGG TCG GTG TGC TGT AAA CAC AAG         965
Lys Val Ser Asp Leu Ser Leu Ser Gly Ser Val Cys Cys Lys His Lys
            295                 300                 305

CCC AGC TCC ACA TCT CTG CTG TCA CCA CCC CGC CAA AAT GCC TTT CAG        1013
Pro Ser Ser Thr Ser Leu Leu Ser Pro Pro Arg Gln Asn Ala Phe Gln
310                 315                 320                 325

CTC AGG CCA TTT ATT GAG ACC AGA CAT TTC CTT TAC TCC AGG GGA GAT        1061
Leu Arg Pro Phe Ile Glu Thr Arg His Phe Leu Tyr Ser Arg Gly Asp
                330                 335                 340

GGC CAA GAG CGT CTA AAC CCC TCA TTC CTA CTC AGC AAC CTC CAG CCT        1109
Gly Gln Glu Arg Leu Asn Pro Ser Phe Leu Leu Ser Asn Leu Gln Pro
            345                 350                 355

AAC TTG ACT GGG GCC AGG AGA CTG GTG GAG ATC ATC TTT CTG GGC TCA        1157
Asn Leu Thr Gly Ala Arg Arg Leu Val Glu Ile Ile Phe Leu Gly Ser
            360                 365                 370

AGG CCT AGG ACA TCA GGA CCA CTC TGC AGG ACA CAC CGT CTA TCG CGT        1205
Arg Pro Arg Thr Ser Gly Pro Leu Cys Arg Thr His Arg Leu Ser Arg
            375                 380                 385

CGA TAC TGG CAG ATG CGG CCC CTG TTC CAA CAG CTG CTG GTG AAC CAT        1253
Arg Tyr Trp Gln Met Arg Pro Leu Phe Gln Gln Leu Leu Val Asn His
390                 395                 400                 405
```

-continued

| | |
|---|---|
| GCA GAG TGC CAA TAT GTC AGA CTC CTC AGG TCA CAT TGC AGG TTT CGA<br>Ala Glu Cys Gln Tyr Val Arg Leu Leu Arg Ser His Cys Arg Phe Arg<br>410                             415                       420 | 1301 |
| ACA GCA AAC CAA CAG GTG ACA GAT GCC TTG AAC ACC AGC CCA CCG CAC<br>Thr Ala Asn Gln Gln Val Thr Asp Ala Leu Asn Thr Ser Pro Pro His<br>               425                       430                       435 | 1349 |
| CTC ATG GAT TTG CTC CGC CTG CAC AGC AGT CCC TGG CAG GTA TAT GGT<br>Leu Met Asp Leu Leu Arg Leu His Ser Ser Pro Trp Gln Val Tyr Gly<br>               440                       445                       450 | 1397 |
| TTT CTT CGG GCC TGT CTC TGC AAG GTG GTG TCT GCT AGT CTC TGG GGT<br>Phe Leu Arg Ala Cys Leu Cys Lys Val Val Ser Ala Ser Leu Trp Gly<br>455                             460                       465 | 1445 |
| ACC AGG CAC AAT GAG CGC CGC TTC TTT AAG AAC TTA AAG AAG TTC ATC<br>Thr Arg His Asn Glu Arg Arg Phe Phe Lys Asn Leu Lys Lys Phe Ile<br>470                       475                       480                       485 | 1493 |
| TCG TTG GGG AAA TAC GGC AAG CTA TCA CTG CAG GAA CTG ATG TGG AAG<br>Ser Leu Gly Lys Tyr Gly Lys Leu Ser Leu Gln Glu Leu Met Trp Lys<br>               490                       495                       500 | 1541 |
| ATG AAA GTA GAG GAT TGC CAC TGG CTC CGC AGC AGC CCG GGG AAG GAC<br>Met Lys Val Glu Asp Cys His Trp Leu Arg Ser Ser Pro Gly Lys Asp<br>               505                       510                       515 | 1589 |
| CGT GTC CCC GCT GCA GAG CAC CGT CTG AGG GAG AGG ATC CTG GCT ACG<br>Arg Val Pro Ala Ala Glu His Arg Leu Arg Glu Arg Ile Leu Ala Thr<br>             520                       525                       530 | 1637 |
| TTC CTG TTC TGG CTG ATG GAC ACA TAC GTG GTA CAG CTG CTT AGG TCA<br>Phe Leu Phe Trp Leu Met Asp Thr Tyr Val Val Gln Leu Leu Arg Ser<br>535                             540                       545 | 1685 |
| TTC TTT TAC ATC ACA GAG AGC ACA TTC CAG AAG AAC AGG CTC TTC TTC<br>Phe Phe Tyr Ile Thr Glu Ser Thr Phe Gln Lys Asn Arg Leu Phe Phe<br>550                       555                       560                       565 | 1733 |
| TAC CGT AAG AGT GTG TGG AGC AAG CTG CAG AGC ATT GGA GTC AGG CAA<br>Tyr Arg Lys Ser Val Trp Ser Lys Leu Gln Ser Ile Gly Val Arg Gln<br>               570                       575                       580 | 1781 |
| CAC CTT GAG AGA GTG CGG CTA CGG GAG CTG TCA CAA GAG GAG GTC AGG<br>His Leu Glu Arg Val Arg Leu Arg Glu Leu Ser Gln Glu Glu Val Arg<br>             585                       590                       595 | 1829 |
| CAT CAC CAG GAC ACC TGG CTA GCC ATG CCC ATC TGC AGA CTG CGC TTC<br>His His Gln Asp Thr Trp Leu Ala Met Pro Ile Cys Arg Leu Arg Phe<br>             600                       605                       610 | 1877 |
| ATC CCC AAG CCC AAC GGC CTG CGG CCC ATT GTG AAC ATG AGT TAT AGC<br>Ile Pro Lys Pro Asn Gly Leu Arg Pro Ile Val Asn Met Ser Tyr Ser<br>615                             620                       625 | 1925 |
| ATG GGT ACC AGA GCT TTG GGC AGA AGG AAG CAG GCC CAG CAT TTC ACC<br>Met Gly Thr Arg Ala Leu Gly Arg Arg Lys Gln Ala Gln His Phe Thr<br>630                       635                       640                       645 | 1973 |
| CAG CGT CTC AAG ACT CTC TTC AGC ATG CTC AAC TAT GAG CGG ACA AAA<br>Gln Arg Leu Lys Thr Leu Phe Ser Met Leu Asn Tyr Glu Arg Thr Lys<br>               650                       655                       660 | 2021 |
| CAT CCT CAC CTT ATG GGG TCT TCT GTA CTG GGT ATG AAT GAC ATC TAC<br>His Pro His Leu Met Gly Ser Ser Val Leu Gly Met Asn Asp Ile Tyr<br>             665                       670                       675 | 2069 |
| AGG ACC TGG CGG GCC TTT GTG CTG CGT GTG CGT GCT CTG GAC CAG ACA<br>Arg Thr Trp Arg Ala Phe Val Leu Arg Val Arg Ala Leu Asp Gln Thr<br>             680                       685                       690 | 2117 |
| CCC AGG ATG TAC TTT GTT AAG GCA GAT GTG ACC GGG GCC TAT GAT GCC<br>Pro Arg Met Tyr Phe Val Lys Ala Asp Val Thr Gly Ala Tyr Asp Ala<br>695                             700                       705 | 2165 |
| ATC CCC CAG GGT AAG CTG GTG GAG GTT GTT GCC AAT ATG ATC AGG CAC<br>Ile Pro Gln Gly Lys Leu Val Glu Val Val Ala Asn Met Ile Arg His<br>710                       715                       720                       725 | 2213 |

```
TCG GAG AGC ACG TAC TGT ATC CGC CAG TAT GCA GTG GTC CGG AGA GAT      2261
Ser Glu Ser Thr Tyr Cys Ile Arg Gln Tyr Ala Val Val Arg Arg Asp
            730                 735                 740

AGC CAA GGC CAA GTC CAC AAG TCC TTT AGG AGA CAG GTC ACC ACC CTC      2309
Ser Gln Gly Gln Val His Lys Ser Phe Arg Arg Gln Val Thr Thr Leu
            745                 750                 755

TCT GAC CTC CAG CCA TAC ATG GGC CAG TTC CTT AAG CAT CTG CAG GAT      2357
Ser Asp Leu Gln Pro Tyr Met Gly Gln Phe Leu Lys His Leu Gln Asp
            760                 765                 770

TCA GAT GCC AGT GCA CTG AGG AAC TCC GTT GTC ATC GAG CAG AGC ATC      2405
Ser Asp Ala Ser Ala Leu Arg Asn Ser Val Val Ile Glu Gln Ser Ile
            775                 780                 785

TCT ATG AAT GAG AGC AGC AGC CTG TTT GAC TTC TTC CTG CAC TTC          2453
Ser Met Asn Glu Ser Ser Ser Leu Phe Asp Phe Phe Leu His Phe
790                 795                 800                 805

CTG CGT CAC AGT GTC GTA AAG ATT GGT GAC AGG TGC TAT ACG CAG TGC      2501
Leu Arg His Ser Val Val Lys Ile Gly Asp Arg Cys Tyr Thr Gln Cys
            810                 815                 820

CAG GGC ATC CCC CAG GGC TCC AGC CTA TCC ACC CTG CTC TGC AGT CTG      2549
Gln Gly Ile Pro Gln Gly Ser Ser Leu Ser Thr Leu Leu Cys Ser Leu
            825                 830                 835

TGT TTC GGA GAC ATG GAG AAC AAG CTG TTT GCT GAG GTG CAG CGG GAT      2597
Cys Phe Gly Asp Met Glu Asn Lys Leu Phe Ala Glu Val Gln Arg Asp
            840                 845                 850

GGG TTG CTT TTA CGT TTT GTT GAT GAC TTT CTG TTG GTG ACG CCT CAC      2645
Gly Leu Leu Leu Arg Phe Val Asp Asp Phe Leu Leu Val Thr Pro His
            855                 860                 865

TTG GAC CAA GCA AAA ACC TTC CTC AGC ACC CTG GTC CAT GGC GTT CCT      2693
Leu Asp Gln Ala Lys Thr Phe Leu Ser Thr Leu Val His Gly Val Pro
870                 875                 880                 885

GAG TAT GGG TGC ATG ATA AAC TTG CAG AAG ACA GTG GTG AAC TTC CCT      2741
Glu Tyr Gly Cys Met Ile Asn Leu Gln Lys Thr Val Val Asn Phe Pro
                890                 895                 900

GTG GAG CCT GGT ACC CTG GGT GGT GCA GCT CCA TAC CAG CTG CCT GCT      2789
Val Glu Pro Gly Thr Leu Gly Gly Ala Ala Pro Tyr Gln Leu Pro Ala
            905                 910                 915

CAC TGC CTG TTT CCC TGG TGT GGC TTG CTG CTG GAC ACT CAG ACT TTG      2837
His Cys Leu Phe Pro Trp Cys Gly Leu Leu Leu Asp Thr Gln Thr Leu
            920                 925                 930

GAG GTG TTC TGT GAC TAC TCA GGT TAT GCC CAG ACC TCA ATT AAG ACG      2885
Glu Val Phe Cys Asp Tyr Ser Gly Tyr Ala Gln Thr Ser Ile Lys Thr
            935                 940                 945

AGC CTC ACC TTC CAG AGT GTC TTC AAA GCT GGG AAG ACC ATG CGG AAC      2933
Ser Leu Thr Phe Gln Ser Val Phe Lys Ala Gly Lys Thr Met Arg Asn
950                 955                 960                 965

AAG CTC CTG TCG GTC TTG CGG TTG AAG TGT CAC GGT CTA TTT CTA GAC      2981
Lys Leu Leu Ser Val Leu Arg Leu Lys Cys His Gly Leu Phe Leu Asp
            970                 975                 980

TTG CAG GTG AAC AGC CTC CAG ACA GTC TGC ATC AAT ATA TAC AAG ATC      3029
Leu Gln Val Asn Ser Leu Gln Thr Val Cys Ile Asn Ile Tyr Lys Ile
            985                 990                 995

TTC CTG CTT CAG GCC TAC AGG TTC CAT GCA TGT GTG ATT CAG CTT CCC      3077
Phe Leu Leu Gln Ala Tyr Arg Phe His Ala Cys Val Ile Gln Leu Pro
            1000                1005                1010

TTT GAC CAG CGT GTT AGG AAG AAC CTC ACA TTC TTT CTG GGC ATC ATC      3125
Phe Asp Gln Arg Val Arg Lys Asn Leu Thr Phe Phe Leu Gly Ile Ile
            1015                1020                1025

TCC AGC CAA GCA TCC TGC TGC TAT GCT ATC CTG AAG GTC AAG AAT CCA      3173
Ser Ser Gln Ala Ser Cys Cys Tyr Ala Ile Leu Lys Val Lys Asn Pro
```

```
                                                       -continued
1030              1035              1040              1045

GGA ATG ACA CTA AAG GCC TCT GGC TCC TTT CCT CCT GAA GCC GCA CAT     3221
Gly Met Thr Leu Lys Ala Ser Gly Ser Phe Pro Pro Glu Ala Ala His
            1050                1055                1060

TGG CTC TGC TAC CAG GCC TTC CTG CTC AAG CTG GCT GCT CAT TCT GTC     3269
Trp Leu Cys Tyr Gln Ala Phe Leu Leu Lys Leu Ala Ala His Ser Val
            1065                1070                1075

ATC TAC AAA TGT CTC CTG GGA CCT CTG AGG ACA GCC CAA AAA CTG CTG     3317
Ile Tyr Lys Cys Leu Leu Gly Pro Leu Arg Thr Ala Gln Lys Leu Leu
            1080                1085                1090

TGC CGG AAG CTC CCA GAG GCG ACA ATG ACC ATC CTT AAA GCT GCA GCT     3365
Cys Arg Lys Leu Pro Glu Ala Thr Met Thr Ile Leu Lys Ala Ala Ala
            1095                1100                1105

GAC CCA GCC CTA AGC ACA GAC TTT CAG ACC ATT TTG GAC TAACCCTGTC      3414
Asp Pro Ala Leu Ser Thr Asp Phe Gln Thr Ile Leu Asp
1110                1115                1120

TCCTTCCGCT AGATGAACAT GAAGGGCGAA TTCCAGCACA CTGGCGGCCG TTACTAGTGG    3474

ATCCGAGCTC GGTACCAAGC TT                                             3496

(2) INFORMATION FOR SEQ ID NO:2:

(i) SEQUENCE CHARACTERISTICS:
        (A) LENGTH: 1122 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Arg Ala Pro Arg Cys Pro Ala Val Arg Ser Leu Leu Arg Ser
 1               5                  10                  15

Arg Tyr Arg Glu Val Trp Pro Leu Ala Thr Phe Val Arg Arg Leu Gly
                20                  25                  30

Pro Glu Gly Arg Arg Leu Val Gln Pro Gly Asp Pro Lys Ile Tyr Arg
            35                  40                  45

Thr Leu Val Ala Gln Cys Leu Val Cys Met His Trp Gly Ser Gln Pro
    50                  55                  60

Pro Pro Ala Asp Leu Ser Phe His Gln Val Ser Leu Lys Glu Leu
65                  70                  75                  80

Val Ala Arg Val Val Gln Arg Leu Cys Glu Arg Asn Glu Arg Asn Val
                85                  90                  95

Leu Ala Phe Gly Phe Glu Leu Leu Asn Glu Ala Arg Gly Gly Pro Pro
            100                 105                 110

Met Ala Phe Thr Ser Ser Val Arg Ser Tyr Leu Pro Asn Thr Val Ile
        115                 120                 125

Glu Thr Leu Arg Val Ser Gly Ala Trp Met Leu Leu Leu Ser Arg Val
    130                 135                 140

Gly Asp Asp Leu Leu Val Tyr Leu Leu Ala His Cys Ala Leu Tyr Leu
145                 150                 155                 160

Leu Val Pro Pro Ser Cys Ala Tyr Gln Val Cys Gly Ser Pro Leu Tyr
                165                 170                 175

Gln Ile Cys Ala Thr Thr Asp Ile Trp Pro Ser Val Ser Ala Ser Tyr
            180                 185                 190

Arg Pro Thr Arg Pro Val Gly Arg Asn Phe Thr Asn Leu Arg Phe Leu
        195                 200                 205

Gln Gln Ile Lys Ser Ser Arg Gln Glu Ala Pro Lys Pro Leu Ala
    210                 215                 220
```

-continued

```
Leu Pro Ser Arg Gly Thr Lys Arg His Leu Ser Leu Thr Ser Thr Ser
225                 230                 235                 240

Val Pro Ser Ala Lys Lys Ala Arg Cys Tyr Pro Val Pro Arg Val Glu
            245                 250                 255

Glu Gly Pro His Arg Gln Val Leu Pro Thr Pro Ser Gly Lys Ser Trp
            260                 265                 270

Val Pro Ser Pro Ala Arg Ser Pro Glu Val Pro Thr Ala Glu Lys Asp
        275                 280                 285

Leu Ser Ser Lys Gly Lys Val Ser Asp Leu Ser Leu Ser Gly Ser Val
        290                 295                 300

Cys Cys Lys His Lys Pro Ser Thr Ser Leu Leu Ser Pro Pro Arg
305                 310                 315                 320

Gln Asn Ala Phe Gln Leu Arg Pro Phe Ile Glu Thr Arg His Phe Leu
                325                 330                 335

Tyr Ser Arg Gly Asp Gly Gln Glu Arg Leu Asn Pro Ser Phe Leu Leu
                340                 345                 350

Ser Asn Leu Gln Pro Asn Leu Thr Gly Ala Arg Arg Leu Val Glu Ile
            355                 360                 365

Ile Phe Leu Gly Ser Arg Pro Arg Thr Ser Gly Pro Leu Cys Arg Thr
        370                 375                 380

His Arg Leu Ser Arg Arg Tyr Trp Gln Met Arg Pro Leu Phe Gln Gln
385                 390                 395                 400

Leu Leu Val Asn His Ala Glu Cys Gln Tyr Val Arg Leu Leu Arg Ser
                405                 410                 415

His Cys Arg Phe Arg Thr Ala Asn Gln Gln Val Thr Asp Ala Leu Asn
                420                 425                 430

Thr Ser Pro Pro His Leu Met Asp Leu Leu Arg Leu His Ser Ser Pro
            435                 440                 445

Trp Gln Val Tyr Gly Phe Leu Arg Ala Cys Leu Cys Lys Val Val Ser
        450                 455                 460

Ala Ser Leu Trp Gly Thr Arg His Asn Glu Arg Arg Phe Phe Lys Asn
465                 470                 475                 480

Leu Lys Lys Phe Ile Ser Leu Gly Lys Tyr Gly Lys Leu Ser Leu Gln
                485                 490                 495

Glu Leu Met Trp Lys Met Lys Val Glu Asp Cys His Trp Leu Arg Ser
            500                 505                 510

Ser Pro Gly Lys Asp Arg Val Pro Ala Ala Glu His Arg Leu Arg Glu
        515                 520                 525

Arg Ile Leu Ala Thr Phe Leu Phe Trp Leu Met Asp Thr Tyr Val Val
530                 535                 540

Gln Leu Leu Arg Ser Phe Phe Tyr Ile Thr Glu Ser Thr Phe Gln Lys
545                 550                 555                 560

Asn Arg Leu Phe Phe Tyr Arg Lys Ser Val Trp Ser Lys Leu Gln Ser
                565                 570                 575

Ile Gly Val Arg Gln His Leu Glu Arg Val Arg Leu Arg Glu Leu Ser
            580                 585                 590

Gln Glu Glu Val Arg His His Gln Asp Thr Trp Leu Ala Met Pro Ile
        595                 600                 605

Cys Arg Leu Arg Phe Ile Pro Lys Pro Asn Gly Leu Arg Pro Ile Val
    610                 615                 620

Asn Met Ser Tyr Ser Met Gly Thr Arg Ala Leu Gly Arg Arg Lys Gln
625                 630                 635                 640
```

```
                          -continued

Ala Gln His Phe Thr Gln Arg Leu Lys Thr Leu Phe Ser Met Leu Asn
            645                 650                 655

Tyr Glu Arg Thr Lys His Pro His Leu Met Gly Ser Ser Val Leu Gly
                660                 665                 670

Met Asn Asp Ile Tyr Arg Thr Trp Arg Ala Phe Val Leu Arg Val Arg
            675                 680                 685

Ala Leu Asp Gln Thr Pro Arg Met Tyr Phe Val Lys Ala Asp Val Thr
        690                 695                 700

Gly Ala Tyr Asp Ala Ile Pro Gln Gly Lys Leu Val Glu Val Val Ala
705                 710                 715                 720

Asn Met Ile Arg His Ser Glu Ser Thr Tyr Cys Ile Arg Gln Tyr Ala
                725                 730                 735

Val Val Arg Arg Asp Ser Gln Gly Gln Val His Lys Ser Phe Arg Arg
                740                 745                 750

Gln Val Thr Thr Leu Ser Asp Leu Gln Pro Tyr Met Gly Gln Phe Leu
            755                 760                 765

Lys His Leu Gln Asp Ser Asp Ala Ser Ala Leu Arg Asn Ser Val Val
            770                 775                 780

Ile Glu Gln Ser Ile Ser Met Asn Glu Ser Ser Ser Leu Phe Asp
785                 790                 795                 800

Phe Phe Leu His Phe Leu Arg His Ser Val Val Lys Ile Gly Asp Arg
                805                 810                 815

Cys Tyr Thr Gln Cys Gln Gly Ile Pro Gln Gly Ser Ser Leu Ser Thr
            820                 825                 830

Leu Leu Cys Ser Leu Cys Phe Gly Asp Met Glu Asn Lys Leu Phe Ala
            835                 840                 845

Glu Val Gln Arg Asp Gly Leu Leu Leu Arg Phe Val Asp Asp Phe Leu
        850                 855                 860

Leu Val Thr Pro His Leu Asp Gln Ala Lys Thr Phe Leu Ser Thr Leu
865                 870                 875                 880

Val His Gly Val Pro Glu Tyr Gly Cys Met Ile Asn Leu Gln Lys Thr
                885                 890                 895

Val Val Asn Phe Pro Val Glu Pro Gly Thr Leu Gly Gly Ala Ala Pro
            900                 905                 910

Tyr Gln Leu Pro Ala His Cys Leu Phe Pro Trp Cys Gly Leu Leu Leu
            915                 920                 925

Asp Thr Gln Thr Leu Glu Val Phe Cys Asp Tyr Ser Gly Tyr Ala Gln
930                 935                 940

Thr Ser Ile Lys Thr Ser Leu Thr Phe Gln Ser Val Phe Lys Ala Gly
945                 950                 955                 960

Lys Thr Met Arg Asn Lys Leu Leu Ser Val Leu Arg Leu Lys Cys His
                965                 970                 975

Gly Leu Phe Leu Asp Leu Gln Val Asn Ser Leu Gln Thr Val Cys Ile
            980                 985                 990

Asn Ile Tyr Lys Ile Phe Leu Leu Gln Ala Tyr Arg Phe His Ala Cys
            995                1000                1005

Val Ile Gln Leu Pro Phe Asp Gln Arg Val Arg Lys Asn Leu Thr Phe
        1010                1015                1020

Phe Leu Gly Ile Ile Ser Ser Gln Ala Ser Cys Cys Tyr Ala Ile Leu
1025                1030                1035                1040

Lys Val Lys Asn Pro Gly Met Thr Leu Lys Ala Ser Gly Ser Phe Pro
                1045                1050                1055

Pro Glu Ala Ala His Trp Leu Cys Tyr Gln Ala Phe Leu Leu Lys Leu
```

1060                1065                1070
Ala Ala His Ser Val Ile Tyr Lys Cys Leu Leu Gly Pro Leu Arg Thr
            1075                1080                1085

Ala Gln Lys Leu Leu Cys Arg Lys Leu Pro Glu Ala Thr Met Thr Ile
    1090                1095                1100

Leu Lys Ala Ala Ala Asp Pro Ala Leu Ser Thr Asp Phe Gln Thr Ile
1105                1110                1115                1120

Leu Asp (2) INFORMATION FOR SEQ ID NO:3:

(i) SEQUENCE CHARACTERISTICS:
        (A) LENGTH: 1132 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..1132
        (D) OTHER INFORMATION: /note= "human telomerase reverse
            transcriptase (hTRT)"

(xi) SEQUENCE DESCRIPTION: SEQ ID NO:3:

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
            85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
            165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
            245                 250                 255

```
Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
            290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
            370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
            435                 440                 445

Val Gln Leu Leu Arg Gln His Ser Ser Pro Trp Gln Val Tyr Gly Phe
            450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
            530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
            610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670
```

```
Pro Gly Leu Leu Gly Ala Ser Val Gly Leu Asp Asp Ile His Arg
        675                 680                 685

Ala Trp Arg Thr Phe Val Leu Arg Val Arg Ala Gln Asp Pro Pro
        690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
            915                 920                 925

Pro Trp Cys Gly Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Ala Gly Pro Leu Pro Ser Glu Ala Val Gln Trp
            1060                1065                1070

Leu Cys His Gln Ala Phe Leu Leu Lys Leu Thr Arg His Arg Val Thr
        1075                1080                1085

Tyr Val Pro Leu Leu Gly Ser Leu Arg Thr Ala Gln Thr Gln Leu Ser
```

```
         1090               1095              1100
Arg Lys Leu Pro Gly Thr Thr Leu Thr Ala Leu Glu Ala Ala Ala Asn
1105              1110              1115              1120

Pro Ala Leu Pro Ser Asp Phe Lys Thr Ile Leu Asp
              1125              1130
```

(2) INFORMATION FOR SEQ ID NO:4:

(i) SEQUENCE CHARACTERISTICS:
        (A) LENGTH: 1808 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..1808
        (D) OTHER INFORMATION: /note= "preliminary sequence of genomic
            mouse telomerase reverse transcriptase
            (mTRT) promoter region"

(ix) FEATURE:
        (A) NAME/KEY: misc_feature
        (B) LOCATION: 1680
        (D) OTHER INFORMATION: /note= "mouse telomerase reverse
            transcriptase (mTRT) cDNA start site"

(ix) FEATURE:
        (A) NAME/KEY: misc_feature
        (B) LOCATION: 1709
        (D) OTHER INFORMATION: /note= "mouse telomerase reverse
            transcriptase (mTRT) ORF start site"

(xi) SEQUENCE DESCRIPTION: SEQ ID NO:4:

```
AAAGCAGGCC TGTAACACAA AGGTCCTTTT TCCTGGTTTA TCGTGGCTGG TAGACAATTT      60

CCACTTGTTT TCCACTTCAG TTTTTTCTAC TCGGTTGTTA TTGGATTCTG ATGCTTGAAC     120

CCAGGTTGGT AGTCAGCAAG TGCACCCCTT CCTTCTTTTT CTTGGTTTTT TTGAGGCAGG     180

TCTCATTTTG CCCAAGTGGA CCTAAATTTC AGCATGTAGT GGCTGGTTTN GAATGCTTTT     240

TCATCCTGCT NTACTTCCCA AGAGTAGCTA ACAAGTGTGC ACCACCATGC CCCGCGATAT     300

TTTTATTTTT GAGACTGTTT TCTATGCTGG TTTCTTTGGG GAACTACACT AAGGTAGCTT     360

ACAAGTGTGC ACCACCATGC CCCGCGATAT TCTTATTTTT GAGACTGTTT TCTATGCTGG     420

TTTCTTTGGG GAACTACACT AAGGTAGCTT CATTGTTGGC ATAAATTTCT CAGTTCAGGC     480

CCATATCTCT TAAGTAGCAG AACTAAGCCA AATCTTCAAA CAAACCCCTT CAAAAAGACT     540

GATGTCCACT AAACGGACTT CTAAAATAGC TCCCTGTAAT CCTGAGCATT TACCAAGGCG     600

GCAGACTTCC TATAAGGGAG TAAATATGAA AACGCGCCTG TTCAAATGCT AGGTCGGTGG     660

ATAGAAGCAA TTTCCTCAGA AAGCTGAAGG CACCAAAGGT TATATTTGTT AGCATTTCAG     720

TGTTTGCCAA ACTCAGCTAC AGTAGAGATC ACAGATTCCC TATTTCCCAG AGATTCAAAA     780

TTCAGCAGCC CCTCTCTAAC TATGGCTCAG AGTCGTGTCA TTACATATGC CCCAACAACA     840

ACCCCCACCC CTATCCTACC CCCGCCTCAC ACGTGCAAGT ACTATCACAG TTGCCAACCT     900

AGCAGAGCTG CCATCCTAAG GTCGAGGTCG CCGCTTTGGC TGTGTGCACA GGCAAGCGCC     960

CTCACCCAAT GGCCCTGGCC TTGCTATGGG TGCGTGAGTT GAGATGATGC TCTGGACTCT    1020

GAGGTGAAGG CCACTGGAAC AGTGAAAAAA GCTAACGCAG GGCTTTTACC TAGGTCCCCT    1080

TCCTTTGGTG GTGGGTGTTT ACGGAACATA TTTGGGATCT GGAGTGTATG GTCGCACCAC    1140

AATAAAGCCT TAACCTATAT AGTAGAATGT TCAGCTGTAA TCATTAAGAA CTGAGATTGC    1200
```

```
CACCACCCAC CTCACTGTCT GTGTCAACCA CAGCAGGCTG GAGCAGTCAG CTCAGGAACA    1260

GGCAAAACCT TAGGTCCTCC GCCTACCTAA CCTTCAATAC ATCAAGGATA GGCTTCTTTG    1320

CTTGCCCAAA CCTCGCCCCA GTCTAGACCA CCTGGGGATT CCCAGCTCAG GGCGAAAAGG    1380

AAGCCCGAGA AGCATTCTGT AGAGGGAAAT CCTGCATGAG TGCGCCCCCT TTCGTTACTC    1440

CAACACATCC AGCAACCACT GAACTTGGCC GGGGAACACA CCTGGTCCTC ATGCACCAGC    1500

ATTGTGACCA TCAACGGAAA AGTACTATTG CTGCGACCCC GCCCCTTCCG CTACAACGCT    1560

TGGTCCGCCT GAATCCCGCC CCTTCCTCCG TTCCCAGCCT CATCTTTTTC GTCGTGGACT    1620

CTCAGTGGCC TGGGTCCTGG CTGTTTTCTA AGCACACCCT TGCATCTTGG TTCCCGCACG    1680

TGGGAGGCCC ATCCCGGCCT TGAGCACAAT GACCCGCGCT CCTCGTTGCC CCGCGGTGCG    1740

CTCTCTGCTG CGCAGCCGAT ACCGGGAGGT GTGGCCGCTG GCAACCTTTG TGCGGCGCCT    1800

GGGGCCCG                                                            1808
```

(2) INFORMATION FOR SEQ ID NO:5:

(i) SEQUENCE CHARACTERISTICS:
        (A) LENGTH: 2651 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..2651
        (D) OTHER INFORMATION: /note= "preliminary sequence of B2.18
            containing the genomic promoter region
            of mouse telomerase reverse
            transcriptase (mTRT)"

(ix) FEATURE:
        (A) NAME/KEY: misc_feature
        (B) LOCATION: 2057
        (D) OTHER INFORMATION: /note= "mouse telomerase reverse
            transcriptase (mTRT) cDNA start site"

(ix) FEATURE:
        (A) NAME/KEY: misc_feature
        (B) LOCATION: 2087
        (D) OTHER INFORMATION: /note= "mouse telomerase reverse
            transcriptase (mTRT) ORF start site"

(xi) SEQUENCE DESCRIPTION: SEQ ID NO:5:

```
AAACAAAGTC AATGAGGAAT GGCTGTGTTC CATCTTGACC ACTGAGAAGT AAAACCGGGT     60

GCAGTGATGT CCAAAAAGGC AAGGTGACAG CAGAGCGGAG GCCCCAATCT AGAGCAGGGC    120

CTTCGGTTTG AATGGGGGAG ATCAAACGGG AGTTGGTTTC TGCCAGCACG TTGGGGTAGA    180

AGGTGGAACA TGAAAGGTCC CCGAGGATTT CGAGAGTCCA TAGGGGTAGC GACACCCGAG    240

GTCTTCTTTT TCACCTCCTT CCCTGCAGGG GAGATGACTT TTACCACAGT CGTTTATGGG    300

AAAGTTCCTA GGGGCAGCCC CTCCCCAAAA AGGCTCTCCC TGGCCTCATG TTTCAAAGCA    360

CAGCTTTTTA AAGCAGGCCT GTTAAGCACA AAGGATCCCG AATCCTGGCT TCATCGTTGG    420

CTGGTAGACA ACTTCCACTC GTTTTCCACT TCAGTTTCTT CTAACTCTGT TGTTATTTGA    480

TTCTGATGCT TGAACCCAGG GTTGTGTAGT CAGCAAGTGC TACCCCCTCC TCCTCTTCTT    540

TGTTTTTTTG AGGCAGGGTC TCATTTTGCC CAAGTGGACC TAAATTTCAG CATGTAGCTG    600

GCCTGGTTTT GAATGCCTTC TCATCCTGCC TCTACTTCCC AAGAGTAGCT TACAAGTGTG    660

CACCACCATG CCCCGCGATA TTCTTATTTT TGAGACTGTT TTCTATGCTG GTTTCTTTGG    720
```

-continued

```
GGAACTACAC TAAGGTAGCT TACAAGTGTG CACCACCATG CCCCGCGATA TTCTTATTTT      780

TGAGACTGTT TTCTATGCTG GTTTCTTTGG GGAACTACAC TAAGGTAGCT TCATTGTTGG      840

CATAAATTTC TCAGTTCAGG CCCATATCTC CTAAGTAGCA GAACTAAGCA AATCTCAAAC      900

AAACCCCTCA AAAAGACTGA TGTCCACTAA ACGGACTTCT AAAATAGCTC CCTGTAATCC      960

TGAGCATTTA CAAGGCGGCA GACCTCCTAT AAGGGAGTAA ATATGAAAAC GCGCCTGTTC     1020

AAATGCTAGG TCGGTGGATA GAAGCAATTT CCTCAGAAAG CTGAAGGCAC CAAAGGTTAT     1080

ATTTGTTAGC ATTTCAGTGT TTGCCAAACT CAGCTACAGT AGAGATCACA GATTCCCTAT     1140

TTCCCAGAGA TTCAAAATTC AGCAGCCCCT CTCTAACTAT GGCTCAGAGT CGTGTCATTA     1200

CATATGCCCC AACAACAACC CCCACCCCTA TCCTACCCCC GCCTCACACG TGCAAGTACT     1260

ATCACAGTTG CCAACCTAGC AGAGCTGCCA TCCTAAGGTC GAGGTCGCCG CTTTGGCTGT     1320

GTGCACAGGA AAGCGCCCTC ACCCAATGGC CCTGGCCTTG CTATGGGTGC GTGAGTTGAG     1380

ATGATGCTCT GGACTCTGAG GTGAAGGCCA CTGGAACAGT GAAAAAAGCT AACGCAGGGC     1440

TTTTACCTAG GTCCCCTTCC TTTGGTGGTG GGTGTTTACG GAACATATTT GGGATCTGGA     1500

GTGTATGGTC GCACCACAAT AAAGCCTTAA CCTATATAGT AGAATTTCAG CTGTAATCAT     1560

TAAGAACTGA GATTGCCACC ACCCACCTCA CTGTCTGTGT CAACCACAGC AGGCTGGAGC     1620

AGTCAGCTCA GGAACAGGCA AAACCTTAGG TCCCTCCGCC TACCTAACCT TCAATACATC     1680

AAGGATAGGC TTCTTTGCTT GCCCAAACCT CGCCCCAGTC TAGACCACCT GGGGATTCCC     1740

AGCTCAGGGC GAAAAGGAAG CCCGAGAAGC ATTCTGTAGA GGGAAATCCT GCATGAGTGC     1800

GCCCCCTTTC GTTACTCCAA CACATCCAGC AACCACTGAA CTTGGCCGGG GAACACACCT     1860

GGTCCTCATG CACCAGCATT GTGACCATCA ACGGAAAAGT ACTATTGCTG CGACCCCGCC     1920

CCTTCCGCTA CAACGCTTGG TCCGCCTGAA TCCCGCCCCT TCCTCCGTTC CCAGCCTCAT     1980

CTTTTTCGTC GTGGACTCTC AGTGGCCTGG GTCCTGGCTG TTTTCTAAGC ACACCCTTGC     2040

ATCTTGGTTC CCGCACGTGG GAAGGCCCAT CCCGGCCTTG AGCACAATGA CCCGCGCTCC     2100

TCGTTGCCCC GCGGTGCGCT CTCTGCTGCG CAGCCGATAC CGGGAGGTGT GGCCGCTGGC     2160

AACCTTTGTG CGGCGCCTGG GGCCCGAGGG CAGGCGGCTT GTGCAACCCG GGACCGAAG      2220

ATCTACCGCA CTTTGGGTTG CCCAATGCCT AGTGTGCATG CACTGGGCT CACAGCCTCC      2280

ACCTGCCGAC CTTTCCTTCC ACCAGGTGGG CCTCCAGGCG GGATCCCCAT GGGTCAGGGG     2340

CGGAAAGCCG GGAGGACGTG GGATAGTGCG TCTAGCTCAT GTGTCAAGAC CCTCTTCTCC     2400

TTACCAGGTG TCATCCCTGA AAAGAGCTGG TGGCCAGGGT TGTGCAGAGA CTCTGCGAGC     2460

GCAACGAGAG AAACGTGCTG GCTTTTGGCT TTGAGCTGCT TAACGAAGCC AGAAGCGGGC     2520

CTCCCATGGC CTTCACTAAT TAGCGTGCGT AAGCTACTTG CCCAACACTG TTATTGAAAA     2580

CCTGCGTGTC AGTGGTGCAT GGATGCTACT GTTGAGCCGA ATGGGCGACA CCTGCTGGTC     2640

TACCTGCTGG C                                                        2651
```

(2) INFORMATION FOR SEQ ID NO:6:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(ix) FEATURE:

(A) NAME/KEY: -
        (B) LOCATION: 1..18
        (D) OTHER INFORMATION: /note= "human telomerase reverse
            transcriptase (hTRT) substrate oligonucleotide "TS""

(xi) SEQUENCE DESCRIPTION: SEQ ID NO:6:

AATCCGTCGA GCAGAGTT                                                        18

(2) INFORMATION FOR SEQ ID NO:7:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..6
        (D) OTHER INFORMATION: /note= "human telomeric repeat"

(xi) SEQUENCE DESCRIPTION: SEQ ID NO:7:

TTAGGG                                                                      6

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "3' primer hTRT.28"

(xi) SEQUENCE DESCRIPTION: SEQ ID NO:8:

CTCGGACCAG GGTCCTGAGG AA                                                   22

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..23
        (D) OTHER INFORMATION: /note= "primer mTRT.35"

(xi) SEQUENCE DESCRIPTION: SEQ ID NO:9:

CTTCCTCAGG ACCCTGGTCC GAG                                                  23

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "primer mTRT.27"

(xi) SEQUENCE DESCRIPTION: SEQ ID NO:10:

ATTGAGGTCT GGGCATACCT GC                                              22

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "3' primer encoding
            carboxy-terminus of hTRT"

(xi) SEQUENCE DESCRIPTION: SEQ ID NO:11:

TCAGCGTCGT CCCCGGGAGC TT                                              22

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "5' primer from upstream
            mTRT Ra-200"

(xi) SEQUENCE DESCRIPTION: SEQ ID NO:12:

TCACCCTCTG AGGCTTCGGT GT                                              22

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "primer mTRT.10"

(xi) SEQUENCE DESCRIPTION: SEQ ID NO:13:

CGTCGATACT GGCAGATGCG G                                               21

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single -continued

```
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "primer mTRT.53"

(xi) SEQUENCE DESCRIPTION: SEQ ID NO:14:

GTGCTGAGGC TACAATGCCC ATGT                                              24

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "5' primer mTRT.9"

(xi) SEQUENCE DESCRIPTION: SEQ ID NO:15:

CTTTTACATC ACAGAGAGCA C                                                 21

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= "primer mTRT.52"

(xi) SEQUENCE DESCRIPTION: SEQ ID NO:16:

CATGTTCATC TAGCGGAAGG AGACA                                             25

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "mF550A oligo"

(xi) SEQUENCE DESCRIPTION: SEQ ID NO:17:

ACAGCTGCTT AGATCTTTCG CTTACATCAC AGA                                    33

(2) INFORMATION FOR SEQ ID NO:18:

(i) SEQUENCE CHARACTERISTICS:
        (A) LENGTH: 35 base pairs
        (B) TYPE: nucleic acid
```

```
        (C) STRANDEDNESS: single
        (D) TOPOLOGY: linear (ii) MOLECULE TYPE: DNA (ix) FEATURE:
        (A) NAME/KEY: -
        (B) LOCATION: 1..35
        (D) OTHER INFORMATION: /note= "mD701A oligo"

(xi) SEQUENCE DESCRIPTION: SEQ ID NO:18:

TTGTTAAGGC AGCTGTGACC GGTGCCTATG ATGCC                                    35

(2) INFORMATION FOR SEQ ID NO:19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..38
        (D) OTHER INFORMATION: /note= "mD860A oligo"

(xi) SEQUENCE DESCRIPTION: SEQ ID NO:19:

TACGTTTTGT TGCTGACTTT CTACTAGTGA CGCCTCAC                                 38

(2) INFORMATION FOR SEQ ID NO:20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..38
        (D) OTHER INFORMATION: /note= "mD600A oligo"

(xi) SEQUENCE DESCRIPTION: SEQ ID NO:20:

GGCATCACCA GGCCACGTGG CTGGCCATGC CCATC                                    35

(2) INFORMATION FOR SEQ ID NO:21:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Trp Leu Met Ser Val Tyr Val Val Glu Leu Leu Arg Ser Phe Phe Tyr
1               5                   10                  15

Val Thr Glu Thr Thr Phe Gln Lys Asn Arg Leu Phe Phe Tyr Arg Lys
            20                  25                  30

Ser Val Trp Ser Lys Leu Gln Ser Ile Gly Ile Arg Gln His Leu Lys
            35                  40                  45

(2) INFORMATION FOR SEQ ID NO:22:
```

```
        (i) SEQUENCE CHARACTERISTICS:
            (A) LENGTH: 54 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:22:

Glu Val Arg Gln His Arg Glu Ala Arg Pro Ala Leu Leu Thr Ser Arg
1               5                  10                  15

Leu Arg Phe Ile Pro Lys Pro Asp Gly Leu Arg Pro Ile Val Asn Met
            20                  25                  30

Asp Tyr Val Val Gly Ala Arg Thr Phe Arg Arg Glu Lys Arg Ala Glu
        35                  40                  45

Arg Leu Thr Ser Arg Val
    50

(2) INFORMATION FOR SEQ ID NO:23:

(i) SEQUENCE CHARACTERISTICS:
            (A) LENGTH: 34 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:23:

Pro Pro Pro Glu Leu Tyr Phe Val Lys Val Asp Val Thr Gly Ala Tyr
1               5                  10                  15

Asp Thr Ile Pro Gln Asp Arg Leu Thr Glu Val Ile Ala Ser Ile Ile
            20                  25                  30

Lys Pro (2) INFORMATION FOR SEQ ID NO:24:

(i) SEQUENCE CHARACTERISTICS:
            (A) LENGTH: 35 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:24:

Lys Ser Tyr Val Gln Cys Gln Gly Ile Pro Gln Gly Ser Ile Leu Ser
1               5                  10                  15

Thr Leu Leu Cys Ser Leu Cys Tyr Gly Asp Met Glu Asn Lys Leu Phe
            20                  25                  30

Ala Gly Ile
        35

(2) INFORMATION FOR SEQ ID NO:25:

(i) SEQUENCE CHARACTERISTICS:
            (A) LENGTH: 17 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:25:

Leu Leu Arg Leu Val Asp Asp Phe Leu Leu Val Thr Pro His Leu Thr
```

```
1               5                  10                 15
His (2) INFORMATION FOR SEQ ID NO:26:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Ala Lys Thr Phe Leu Arg Thr Leu Val Arg Gly Val Pro Glu Tyr Gly
1               5                  10                 15

Cys Val Val Asn Leu Arg Lys Thr Val Val
            20                 25

(2) INFORMATION FOR SEQ ID NO:27:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

His Gly Leu Phe Pro Trp Cys Gly Leu Leu Leu
1               5                  10

(2) INFORMATION FOR SEQ ID NO:28:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Trp Leu Met Asp Thr Tyr Val Val Gln Leu Leu Arg Ser Phe Phe Tyr
1               5                  10                 15

Ile Thr Glu Ser Thr Phe Gln Lys Asn Arg Leu Phe Phe Tyr Arg Lys
            20                 25                 30

Ser Val Trp Ser Lys Leu Gln Ser Ile Gly Val Arg Gln His Leu Glu
        35                 40                 45

(2) INFORMATION FOR SEQ ID NO:29:

(i) SEQUENCE CHARACTERISTICS:
        (A) LENGTH: 54 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Glu Val Arg His His Gln Asp Thr Trp Leu Ala Met Pro Ile Cys Arg
1               5                  10                 15

Leu Arg Phe Ile Pro Lys Pro Asn Gly Leu Arg Pro Ile Val Asn Met
            20                 25                 30
```

```
Ser Tyr Ser Met Gly Thr Arg Ala Leu Gly Arg Arg Lys Gln Ala Gln
        35                  40                  45

His Phe Thr Gln Arg Leu
    50

(2) INFORMATION FOR SEQ ID NO:30:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

Gln Thr Pro Arg Met Tyr Phe Val Lys Ala Asp Val Thr Gly Ala Tyr
1               5                   10                  15

Asp Ala Ile Pro Gln Gly Lys Leu Val Glu Val Val Ala Asn Met Ile
            20                  25                  30

Arg His (2) INFORMATION FOR SEQ ID NO:31:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Arg Cys Tyr Thr Gln Cys Gln Gly Ile Pro Gln Gly Ser Ser Leu Ser
1               5                   10                  15

Thr Leu Leu Cys Ser Leu Cys Phe Gly Asp Met Glu Asn Lys Leu Phe
            20                  25                  30

Ala Glu Val
        35

(2) INFORMATION FOR SEQ ID NO:32:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Leu Leu Arg Phe Val Asp Asp Phe Leu Leu Val Thr Pro His Leu Asp
1               5                   10                  15

Gln (2) INFORMATION FOR SEQ ID NO:33:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide
```

-continued (xi) SEQUENCE DESCRIPTION: SEQ ID NO:33:

Ala Lys Thr Phe Leu Ser Thr Leu Val His Gly Val Pro Glu Tyr Gly
1               5                  10                  15

Cys Met Ile Asn Leu Gln Lys Thr Val Val
            20                  25

(2) INFORMATION FOR SEQ ID NO:34:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

His Cys Leu Phe Pro Trp Cys Gly Leu Leu Leu
1               5                  10

(2) INFORMATION FOR SEQ ID NO:35:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

Trp Ile Phe Glu Asp Leu Val Val Ser Leu Ile Arg Cys Phe Phe Tyr
1               5                  10                  15

Val Thr Glu Gln Gln Lys Ser Tyr Ser Lys Thr Tyr Tyr Tyr Arg Lys
            20                  25                  30

Asn Ile Trp Asp Val Ile Met Lys Met Ser Ile Ala Asp Leu Lys Lys
            35                  40                  45

(2) INFORMATION FOR SEQ ID NO:36:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Lys Glu Val Glu Glu Trp Lys Lys Ser Leu Gly Phe Ala Pro Gly Lys
1               5                  10                  15

Leu Arg Leu Ile Pro Lys Lys Thr Thr
            20                  25

(2) INFORMATION FOR SEQ ID NO:37:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

Phe Arg Pro Ile Met Thr Phe Asn Lys Lys Ile Val Asn Ser Asp Arg

```
                  1               5                  10                 15
Lys Thr Thr Lys Leu Thr Thr Asn Thr Lys Leu Leu Asn
                 20                 25
```

(2) INFORMATION FOR SEQ ID NO:38:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
Gly Gln Pro Lys Leu Phe Phe Ala Thr Met Asp Ile Glu Lys Cys Tyr
1               5                  10                 15
Asp Ser Val Asn Arg Glu Lys Leu Ser Thr Phe Leu Lys Thr Thr Lys
                20                  25                 30
Leu Leu
```

(2) INFORMATION FOR SEQ ID NO:39:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

```
Lys Phe Tyr Lys Gln Thr Lys Gly Ile Pro Gln Gly Leu Cys Val Ser
1               5                  10                 15
Ser Ile Leu Ser Ser Phe Tyr Tyr Ala Thr Leu Glu Glu Ser Ser Leu
                20                  25                 30
Gly Phe Leu
        35
```

(2) INFORMATION FOR SEQ ID NO:40:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

```
Leu Met Arg Leu Thr Asp Asp Tyr Leu Leu Ile Thr Thr Gln Glu Asn
1               5                  10                 15
Asn
```

(2) INFORMATION FOR SEQ ID NO:41:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

```
Ala Val Leu Phe Ile Glu Lys Leu Ile Asn Val Ser Arg Glu Asn Gly
1               5                   10                  15

Phe Lys Phe Asn Met Lys Lys Leu Gln Thr
            20                  25
```

(2) INFORMATION FOR SEQ ID NO:42:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Gln Asp Tyr Cys Asp Trp Ile Gly Ile Ser Ile
1               5                   10
```

(2) INFORMATION FOR SEQ ID NO:43:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Trp Leu Phe Arg Gln Leu Ile Pro Lys Ile Ile Gln Thr Phe Phe Tyr
1               5                   10                  15

Cys Thr Glu Ile Ser Ser Thr Val Thr Ile Val Tyr Phe Arg His Asp
            20                  25                  30

Thr Trp Asn Lys Leu Ile Thr Pro Phe Ile Val Glu Tyr Phe Lys
            35                  40                  45
```

(2) INFORMATION FOR SEQ ID NO:44:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

```
Cys Arg Asn His Asn Ser Tyr Thr Leu Ser Asn Phe Asn His Ser Lys
1               5                   10                  15

Met Arg Ile Ile Pro Lys Lys Ser Asn Asn
            20                  25
```

(2) INFORMATION FOR SEQ ID NO:45:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

```
Phe Arg Ile Ile Ala Ile Pro Cys Arg Gly Ala Asp Glu Glu Glu Phe
1               5                   10                  15
```

```
Thr Ile Tyr Lys Glu Asn His Lys Asn Ala Ile Gln Pro
            20                  25
```

(2) INFORMATION FOR SEQ ID NO:46:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

```
Val Leu Pro Glu Leu Tyr Phe Met Lys Phe Asp Val Lys Ser Cys Tyr
1               5                   10                  15
Asp Ser Ile Pro Arg Met Glu Cys Met Arg Ile Leu Lys Asp Ala Leu
            20                  25                  30
Lys Asn
```

(2) INFORMATION FOR SEQ ID NO:47:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:47:

```
Lys Cys Tyr Ile Arg Glu Asp Gly Leu Phe Gln Gly Ser Ser Leu Ser
1               5                   10                  15
Ala Pro Ile Val Asp Leu Val Tyr Asp Asp Leu Leu Glu Phe Tyr Ser
            20                  25                  30
Glu Phe Lys
        35
```

(2) INFORMATION FOR SEQ ID NO:48:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:48:

```
Ile Leu Lys Leu Ala Asp Asp Phe Leu Ile Ile Ser Thr Asp Gln Gln
1               5                   10                  15
Gln
```

(2) INFORMATION FOR SEQ ID NO:49:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:49:

```
Val Ile Asn Ile Lys Lys Leu Ala Met Gly Gly Phe Gln Lys Tyr Asn
1               5                   10                  15
```

```
Ala Lys Ala Asn Arg Asp Lys Ile Leu Ala
            20                  25
```

(2) INFORMATION FOR SEQ ID NO:50:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:50:

```
Lys Glu Leu Glu Val Trp Lys His Ser Ser Thr
1               5                   10
```

(2) INFORMATION FOR SEQ ID NO:51:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:51:

```
Trp Leu Tyr Asn Ser Phe Ile Ile Pro Ile Leu Gln Ser Phe Phe Tyr
1               5                   10                  15

Ile Thr Glu Ser Ser Asp Leu Arg Asn Arg Thr Val Tyr Phe Arg Lys
            20                  25                  30

Asp Ile Trp Lys Leu Leu Cys Arg Pro Phe Ile Thr Ser Met Lys Met
            35                  40                  45
```

(2) INFORMATION FOR SEQ ID NO:52:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

```
Asn Asn Val Arg Met Asp Thr Gln Lys Thr Thr Leu Pro Pro Ala Val
1               5                   10                  15

Ile Arg Leu Leu Pro Lys Lys Asn Thr
            20                  25
```

(2) INFORMATION FOR SEQ ID NO:53:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

```
Phe Arg Leu Ile Thr Asn Leu Arg Lys Arg Phe Leu Ile Lys Met Gly
1               5                   10                  15

Ser Asn Lys Lys Met Leu Val Ser Thr Asn Gln Thr Leu
            20                  25
```

(2) INFORMATION FOR SEQ ID NO:54:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

```
Phe Gly Arg Lys Lys Tyr Phe Val Arg Ile Asp Ile Lys Ser Cys Tyr
 1               5                  10                  15
Asp Arg Ile Lys Gln Asp Leu Met Phe Arg Ile Val Lys Lys Lys Leu
            20                  25                  30
Lys Asp
```

(2) INFORMATION FOR SEQ ID NO:55:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:55:

```
Ser Gln Tyr Leu Gln Lys Val Gly Ile Pro Gln Gly Ser Ile Leu Ser
 1               5                  10                  15
Ser Phe Leu Cys His Phe Tyr Met Glu Asp Leu Ile Asp Glu Tyr Leu
            20                  25                  30
Ser Phe Thr
        35
```

(2) INFORMATION FOR SEQ ID NO:56:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:56:

```
Leu Leu Arg Val Val Asp Asp Phe Leu Phe Ile Thr Val Asn Lys Lys
 1               5                  10                  15
Asp
```

(2) INFORMATION FOR SEQ ID NO:57:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:57:

```
Ala Lys Lys Phe Leu Asn Leu Ser Leu Arg Gly Phe Glu Lys His Asn
 1               5                  10                  15
Phe Ser Thr Ser Leu Glu Lys Thr Val Ile
```

```
                     20                  25

(2) INFORMATION FOR SEQ ID NO:58:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:58:

Lys Lys Arg Met Pro Phe Phe Gly Phe Ser Val
1               5                   10

(2) INFORMATION FOR SEQ ID NO:59:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:59:

Tyr Tyr Arg Lys
1

(2) INFORMATION FOR SEQ ID NO:60:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:60:

Gly Ile Pro Gln
1

(2) INFORMATION FOR SEQ ID NO:61:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:61:

Asp Asp Phe Leu Leu
1               5

(2) INFORMATION FOR SEQ ID NO:62:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
```

-continued

```
        (B) LOCATION: 2
        (D) OTHER INFORMATION: /product= "OTHER"
            /note= "Xaa = Ile or Leu"

(ix) FEATURE:
        (A) NAME/KEY: Modified-site
        (B) LOCATION: 7
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 8
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 10
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 11
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 12
        (D) OTHER INFORMATION: /product= "OTHER"
            /note= "Xaa = Arg or Gln"

(ix) FEATURE:
        (A) NAME/KEY: Modified-site
        (B) LOCATION: 13
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
        (A) NAME/KEY: Modified-site
        (B) LOCATION: 21
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
        (A) NAME/KEY: Modified-site
        (B) LOCATION: 25
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
        (A) NAME/KEY: Modified-site
        (B) LOCATION: 28
        (D) OTHER INFORMATION: /product= "OTHER"
            /note= "Xaa = Tyr or Phe"

(ix) FEATURE:
        (A) NAME/KEY: Modified-site
        (B) LOCATION: 29
        (D) OTHER INFORMATION: /product= "OTHER"
            /note= "Xaa = Tyr or Phe"

(ix) FEATURE:
```

(A) NAME/KEY: Modified-site
            (B) LOCATION: 31
            (D) OTHER INFORMATION: /product= "OTHER"
                /note= "Xaa = Lys or His"

(xi) SEQUENCE DESCRIPTION: SEQ ID NO:62:

Trp Xaa Xaa Xaa Xaa Xaa Xaa Xaa Xaa Xaa Xaa Xaa Xaa Phe Phe Tyr
1               5                   10                  15

Xaa Thr Glu Xaa Xaa Xaa Xaa Xaa Xaa Xaa Xaa Xaa Arg Xaa Xaa
            20                  25                  30

Xaa Trp (2) INFORMATION FOR SEQ ID NO:63:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Ile or Leu"

(ix) FEATURE:
        (A) NAME/KEY: Modified-site
        (B) LOCATION: 7
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 8
        (D) OTHER INFORMATION: /product= "OTHER"
            /note= "Xaa = hydrophobic amino acid
            selected from Ala, Leu, Ile, Val, Pro,
            Phe or Trp or Met"

(ix) FEATURE:
        (A) NAME/KEY: Modified-site
        (B) LOCATION: 10
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 11
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 12
        (D) OTHER INFORMATION: /product= "OTHER"
            /note= "Xaa = Arg or Gln"

(ix) FEATURE:
        (A) NAME/KEY: Modified-site
        (B) LOCATION: 13
        (D) OTHER INFORMATION: /product= "OTHER"
            /note= "Xaa = polar amino acid
            selected from Gly, Ser, Thr, Tyr, Cys,
            Asn or Gln"

(ix) FEATURE:

```
            (A) NAME/KEY: Modified-site
            (B) LOCATION: 21
            (D) OTHER INFORMATION: /product= "OTHER"
                /note= "Xaa = polar amino acid
                selected from Gly, Ser, Thr, Tyr, Cys,
                Asn or Gln"

(ix) FEATURE:
            (A) NAME/KEY: Modified-site
            (B) LOCATION: 25
            (D) OTHER INFORMATION: /product= "OTHER"
                /note= "Xaa = polar amino acid
                selected from Gly, Ser, Thr, Tyr, Cys,
                Asn or Gln"

(ix) FEATURE:
            (A) NAME/KEY: Modified-site
            (B) LOCATION: 29
            (D) OTHER INFORMATION: /product= "OTHER"
                /note= "Xaa = Tyr or Phe"

(ix) FEATURE:
            (A) NAME/KEY: Modified-site
            (B) LOCATION: 30
            (D) OTHER INFORMATION: /product= "OTHER"
                /note= "Xaa = Tyr or Phe"

(ix) FEATURE:
            (A) NAME/KEY: Modified-site
            (B) LOCATION: 32
            (D) OTHER INFORMATION: /product= "OTHER"
                /note= "Xaa = Lys or His"

(xi) SEQUENCE DESCRIPTION: SEQ ID NO:63:

Trp Xaa Xaa Xaa Xaa Xaa Xaa Xaa Xaa Xaa Xaa Xaa Xaa Phe Phe Tyr
1               5                   10                  15

Xaa Thr Glu Xaa Xaa Xaa Xaa Xaa Xaa Xaa Xaa Xaa Xaa Xaa Arg Xaa
            20                  25                  30

Xaa Xaa Trp
        35

(2) INFORMATION FOR SEQ ID NO:64:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = hydrophobic amino acid
                selected from Ala, Leu, Ile, Val, Pro,
                Phe, Trp or Met"

(ix) FEATURE:
            (A) NAME/KEY: Modified-site
            (B) LOCATION: 3
            (D) OTHER INFORMATION: /product= "OTHER"
                /note= "Xaa = hydrophobic amino acid
                selected from Ala, Leu, Ile, Val, Pro,
                Phe, Trp or Met"

(ix) FEATURE:
            (A) NAME/KEY: Modified-site
            (B) LOCATION: 4
            (D) OTHER INFORMATION: /product= "OTHER"
                /note= "Xaa = Ile or Leu"

(ix) FEATURE:
            (A) NAME/KEY: Modified-site
```

```
       (B) LOCATION: 9
       (D) OTHER INFORMATION: /product= "OTHER"
           /note= "Xaa = polar amino acid
           selected from Gly, Ser, Thr, Tyr, Cys,
           Asn or Gln"

(xi) SEQUENCE DESCRIPTION: SEQ ID NO:64:

Xaa Arg Xaa Xaa Pro Lys Xaa Xaa Xaa
1               5

(2) INFORMATION FOR SEQ ID NO:65:

(i) SEQUENCE CHARACTERISTICS:
       (A) LENGTH: 7 amino acids
       (B) TYPE: amino acid
       (C) STRANDEDNESS:
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /product= "OTHER"
           /note= "Xaa = Phe or Leu"

(ix) FEATURE:
       (A) NAME/KEY: Modified-site
       (B) LOCATION: 3
       (D) OTHER INFORMATION: /product= "OTHER"
           /note= "Xaa = hydrophobic amino acid
           selected from Ala, Leu, Ile, Val, Pro,
           Phe, Trp or Met"

(ix) FEATURE:
       (A) NAME/KEY: Modified-site
       (B) LOCATION: 7
       (D) OTHER INFORMATION: /product= "OTHER"
           /note= "Xaa = hydrophobic amino acid
           selected from Ala, Leu, Ile, Val, Pro,
           Phe, Trp or Met"

(xi) SEQUENCE DESCRIPTION: SEQ ID NO:65:

Xaa Arg Xaa Ile Xaa Xaa Xaa
1               5

(2) INFORMATION FOR SEQ ID NO:66:

(i) SEQUENCE CHARACTERISTICS:
       (A) LENGTH: 17 amino acids
       (B) TYPE: amino acid
       (C) STRANDEDNESS:
       (D) TOPOLOGY: linear (ii) MOLECULE TYPE: peptide (ix) FEATURE:
       (A) NAME/KEY: Modified-site
       (B) LOCATION: 2
       (D) OTHER INFORMATION: /product= "OTHER"
           /note= "Xaa = charged amino acid
           selected from Asp, Glu, His, Lys or Arg"

(ix) FEATURE:
       (A) NAME/KEY: Modified-site
       (B) LOCATION: 4
       (D) OTHER INFORMATION: /product= "OTHER"
           /note= "Xaa = Tyr or Phe"

(ix) FEATURE:
       (A) NAME/KEY: Modified-site
       (B) LOCATION: 6
       (D) OTHER INFORMATION: /product= "OTHER"
           /note= "Xaa = hydrophobic amino acid
           selected from Ala, Leu, Ile, Val, Pro,
```

```
                   Phe, Trp or Met"

(ix) FEATURE:
          (A) NAME/KEY: Modified-site
          (B) LOCATION: 8
          (D) OTHER INFORMATION: /product= "OTHER"
              /note= "Xaa = hydrophobic amino acid
                 selected fron Ala, Leu, Ile, Val, Pro,
                 Phe, Trp or Met"

(ix) FEATURE:
          (A) NAME/KEY: Modified-site
          (B) LOCATION: 10
          (D) OTHER INFORMATION: /product= "OTHER"
              /note= "Xaa = hydrophobic amino acid
                 selected from Ala, Leu, Ile, Val, Pro,
                 Phe, Trp or Met"

(ix) FEATURE:
          (A) NAME/KEY: Modified-site
          (B) LOCATION: 13
          (D) OTHER INFORMATION: /product= "OTHER"
              /note= "Xaa = Cys or Ala"

(ix) FEATURE:
          (A) NAME/KEY: Modified-site
          (B) LOCATION: 17
          (D) OTHER INFORMATION: /product= "OTHER"
              /note= "Xaa = Ile or Val"

(xi) SEQUENCE DESCRIPTION: SEQ ID NO:66:

Pro Xaa Xaa Xaa Phe Xaa Xaa Xaa Asp Xaa Xaa Xaa Xaa Tyr Asp Xaa
 1               5                  10                  15

Xaa (2) INFORMATION FOR SEQ ID NO:67:

(i) SEQUENCE CHARACTERISTICS:
          (A) LENGTH: 17 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 3
          (D) OTHER INFORMATION: /product= "OTHER"
              /note= "Xaa = Arg or Gln"

(ix) FEATURE:
          (A) NAME/KEY: Modified-site
          (B) LOCATION: 7
          (D) OTHER INFORMATION: /product= "OTHER"
              /note= "Xaa = Ile or Leu"

(ix) FEATURE:
          (A) NAME/KEY: Modified-site
          (B) LOCATION: 8
          (D) OTHER INFORMATION: /product= "OTHER"
              /note= "Xaa = Pro or Phe"

(ix) FEATURE:
          (A) NAME/KEY: Modified-site
          (B) LOCATION: 11
          (D) OTHER INFORMATION: /product= "OTHER"
              /note= "Xaa = Ser or Leu"

(ix) FEATURE:
          (A) NAME/KEY: Modified-site
          (B) LOCATION: 13
          (D) OTHER INFORMATION: /product= "OTHER"
              /note= "Xaa = Leu or Val"

(ix) FEATURE:
```

(A) NAME/KEY: Modified-site
        (B) LOCATION: 16
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 17
        (D) OTHER INFORMATION: /product= "OTHER"
            /note= "Xaa = Ile or Leu"

(xi) SEQUENCE DESCRIPTION: SEQ ID NO:67:

Tyr Xaa Xaa Xaa Xaa Gly Xaa Xaa Gln Gly Xaa Xaa Xaa Ser Xaa Xaa
1               5                   10                  15

Xaa (2) INFORMATION FOR SEQ ID NO:68:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Ile or Leu"

(ix) FEATURE:
        (A) NAME/KEY: Modified-site
        (B) LOCATION: 2
        (D) OTHER INFORMATION: /product= "OTHER"
            /note= "Xaa = Leu or Met"

(ix) FEATURE:
        (A) NAME/KEY: Modified-site
        (B) LOCATION: 3
        (D) OTHER INFORMATION: /product= "OTHER"
            /note= "Xaa = Arg or Lys"

(ix) FEATURE:
        (A) NAME/KEY: Modified-site
        (B) LOCATION: 4
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 8
        (D) OTHER INFORMATION: /product= "OTHER"
            /note= "Xaa = Tyr or Phe"

(ix) FEATURE:
        (A) NAME/KEY: Modified-site
        (B) LOCATION: 10
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 11
        (D) OTHER INFORMATION: /product= "OTHER"
            /note= "Xaa = Ile or Val"

(ix) FEATURE:
        (A) NAME/KEY: Modified-site (B) LOCATION: 12
            (D) OTHER INFORMATION: /product= "OTHER"
                /note= "Xaa = Thr or Ser"

(xi) SEQUENCE DESCRIPTION: SEQ ID NO:68:

Xaa Xaa Xaa Xaa Xaa Asp Asp Xaa Leu Xaa Xaa Xaa
1               5                   10

(2) INFORMATION FOR SEQ ID NO:69:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Gly or Val"

(ix) FEATURE:
        (A) NAME/KEY: Modified-site
        (B) LOCATION: 4
        (D) OTHER INFORMATION: /product= "OTHER"
            /note= "Xaa = charged amino acid
            selected from Asp, Glu, His, Lys or Arg"

(ix) FEATURE:
        (A) NAME/KEY: Modified-site
        (B) LOCATION: 6
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
        (A) NAME/KEY: Modified-site
        (B) LOCATION: 10
        (D) OTHER INFORMATION: /product= "OTHER"
            /note= "Xaa = Asn or Ser"

(xi) SEQUENCE DESCRIPTION: SEQ ID NO:69:

Xaa Xaa Xaa Xaa Xaa Xaa Xaa Xaa Xaa Xaa Xaa Xaa Lys Xaa Xaa Xaa
1               5                   10                  15

(2) INFORMATION FOR SEQ ID NO:70:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Trp or Phe"

(ix) FEATURE:
        (A) NAME/KEY: Modified-site
        (B) LOCATION: 3
        (D) OTHER INFORMATION: /product= "OTHER"
            /note= "Xaa = Gly or His"

(ix) FEATURE:
        (A) NAME/KEY: Modified-site
        (B) LOCATION: 5
        (D) OTHER INFORMATION: /product= "OTHER"

```
            /note= "Xaa = Ser or Leu"

(xi) SEQUENCE DESCRIPTION: SEQ ID NO:70:

Xaa Xaa Xaa Xaa Xaa Xaa
1               5

(2) INFORMATION FOR SEQ ID NO:71:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Ile or Leu"

(ix) FEATURE:
        (A) NAME/KEY: Modified-site
        (B) LOCATION: 7
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 8
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 10
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 11
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 12
        (D) OTHER INFORMATION: /product= "OTHER"
            /note= "Xaa = Arg or Gln"

(ix) FEATURE:
        (A) NAME/KEY: Modified-site
        (B) LOCATION: 13
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
        (A) NAME/KEY: Modified-site
        (B) LOCATION: 21
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
```

(A) NAME/KEY: Modified-site
            (B) LOCATION: 25
            (D) OTHER INFORMATION: /product= "OTHER"
                /note= "Xaa = polar amino acid
                selected from Gly, Ser, Thr, Tyr, Cys,
                Asn or Gln"

(ix) FEATURE:
            (A) NAME/KEY: Modified-site
            (B) LOCATION: 28
            (D) OTHER INFORMATION: /product= "OTHER"
                /note= "Xaa = Tyr or Phe"

(ix) FEATURE:
            (A) NAME/KEY: Modified-site
            (B) LOCATION: 29
            (D) OTHER INFORMATION: /product= "OTHER"
                /note= "Xaa = Tyr or Phe"

(ix) FEATURE:
            (A) NAME/KEY: Modified-site
            (B) LOCATION: 31
            (D) OTHER INFORMATION: /product= "OTHER"
                /note= "Xaa = Lys or His"

(xi) SEQUENCE DESCRIPTION: SEQ ID NO:71:

Trp Xaa Xaa Xaa Xaa Xaa Xaa Xaa Xaa Xaa Xaa Xaa Xaa Phe Phe Tyr
1               5                   10                  15

Val Thr Glu Xaa Xaa Xaa Xaa Xaa Xaa Xaa Xaa Xaa Xaa Arg Xaa Xaa
            20                  25                  30

Xaa Trp (2) INFORMATION FOR SEQ ID NO:72:

(i) SEQUENCE CHARACTERISTICS:
            (A) LENGTH: 35 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /note= "Xaa = Ile or Leu"

(ix) FEATURE:
            (A) NAME/KEY: Modified-site
            (B) LOCATION: 7
            (D) OTHER INFORMATION: /product= "OTHER"
                /note= "Xaa = hydrophobic amino acid
                selected from Ala, Leu, Ile, Val, Pro,
                Phe, Trp or Met"

(ix) FEATURE:
            (A) NAME/KEY: Modified-site
            (B) LOCATION: 8
            (D) OTHER INFORMATION: /product= "OTHER"
                /note= "Xaa = hydrophobic amino acid
                selected from Ala, Leu, Ile, Val, Pro,
                Phe, Trp or Met"

(ix) FEATURE:
            (A) NAME/KEY: Modified-site
            (B) LOCATION: 10
            (D) OTHER INFORMATION: /product= "OTHER"
                /note= "Xaa = hydrophobic amino acid
                selected from Ala, Leu, Ile, Val, Pro,
                Phe, Trp or Met"

(ix) FEATURE:
            (A) NAME/KEY: Modified-site
            (B) LOCATION: 11

-continued (D) OTHER INFORMATION: /product= "OTHER"
                    /note= "Xaa = hydrophobic amino acid
                    selected from Ala, Leu, Ile, Val, Pro,
                    Phe, Trp or Met"

(ix) FEATURE:
                (A) NAME/KEY: Modified-site
                (B) LOCATION: 12
                (D) OTHER INFORMATION: /product= "OTHER"
                    /note= "Xaa = Arg or Gln"

(ix) FEATURE:
                (A) NAME/KEY: Modified-site
                (B) LOCATION: 13
                (D) OTHER INFORMATION: /product= "OTHER"
                    /note= "Xaa = polar amino acid
                    selected from Gly, Ser, Thr, Tyr, Cys,
                    Asn or Gln"

(ix) FEATURE:
                (A) NAME/KEY: Modified-site
                (B) LOCATION: 21
                (D) OTHER INFORMATION: /product= "OTHER"
                    /note= "Xaa = polar amino acid
                    selected from Gly, Ser, Thr, Tyr, Cys,
                    Asn or Gln"

(ix) FEATURE:
                (A) NAME/KEY: Modified-site
                (B) LOCATION: 25
                (D) OTHER INFORMATION: /product= "OTHER"
                    /note= "Xaa = polar amino acid
                    selected from Gly, Ser, Thr, Tyr, Cys,
                    Asn or Gln"

(ix) FEATURE:
                (A) NAME/KEY: Modified-site
                (B) LOCATION: 29
                (D) OTHER INFORMATION: /product= "OTHER"
                    /note= "Xaa = Tyr or Phe"

(ix) FEATURE:
                (A) NAME/KEY: Modified-site
                (B) LOCATION: 30
                (D) OTHER INFORMATION: /product= "OTHER"
                    /note= "Xaa = Tyr or Phe"

(ix) FEATURE:
                (A) NAME/KEY: Modified-site
                (B) LOCATION: 32
                (D) OTHER INFORMATION: /product= "OTHER"
                    /note= "Xaa = Lys or His"

(xi) SEQUENCE DESCRIPTION: SEQ ID NO:72:

Trp Xaa Xaa Xaa Xaa Xaa Xaa Xaa Xaa Xaa Xaa Xaa Xaa Phe Phe Tyr
1               5                   10                  15

Val Thr Glu Xaa Xaa Xaa Xaa Xaa Xaa Xaa Xaa Xaa Xaa Xaa Arg Xaa
            20                  25                  30

Xaa Xaa Trp
        35

(2) INFORMATION FOR SEQ ID NO:73:

(i) SEQUENCE CHARACTERISTICS:
                (A) LENGTH: 9 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /product= "OTHER"

```
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 3
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 4
        (D) OTHER INFORMATION: /product= "OTHER"
            /note= "Xaa = Ile or Leu"

(ix) FEATURE:
        (A) NAME/KEY: Modified-site
        (B) LOCATION: 9
        (D) OTHER INFORMATION: /product= "OTHER"
            /note= "Xaa = polar amino acid
            selected from Gly, Ser, Thr, Tyr, Cys,
            Asn or Gln"

(xi) SEQUENCE DESCRIPTION: SEQ ID NO:73:

Xaa Arg Xaa Xaa Pro Lys Xaa Asp Xaa
1               5

(2) INFORMATION FOR SEQ ID NO:74:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /note= "Xaa = Tyr or Phe"

(ix) FEATURE:
        (A) NAME/KEY: Modified-site
        (B) LOCATION: 6
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 10
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 13
        (D) OTHER INFORMATION: /product= "OTHER"
            /note= "Xaa = Cys or Ala"

(ix) FEATURE:
        (A) NAME/KEY: Modified-site
        (B) LOCATION: 17
        (D) OTHER INFORMATION: /product= "OTHER"
            /note= "Xaa = Ile or Val"

(xi) SEQUENCE DESCRIPTION: SEQ ID NO:74:

Pro Glu Xaa Xaa Phe Xaa Xaa Val Asp Xaa Xaa Xaa Xaa Tyr Asp Xaa
```

```
1               5                  10                 15
Xaa (2) INFORMATION FOR SEQ ID NO:75:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = Arg or Gln"

(ix) FEATURE:
        (A) NAME/KEY: Modified-site
        (B) LOCATION: 7
        (D) OTHER INFORMATION: /product= "OTHER"
            /note= "Xaa = Ile or Leu"

(ix) FEATURE:
        (A) NAME/KEY: Modified-site
        (B) LOCATION: 8
        (D) OTHER INFORMATION: /product= "OTHER"
            /note= "Xaa = Pro or Phe"

(ix) FEATURE:
        (A) NAME/KEY: Modified-site
        (B) LOCATION: 11
        (D) OTHER INFORMATION: /product= "OTHER"
            /note= "Xaa = Ser or Leu"

(ix) FEATURE:
        (A) NAME/KEY: Modified-site
        (B) LOCATION: 13
        (D) OTHER INFORMATION: /product= "OTHER"
            /note= "Xaa = Leu or Val"

(ix) FEATURE:
        (A) NAME/KEY: Modified-site
        (B) LOCATION: 16
        (D) OTHER INFORMATION: /product= "OTHER"
            /note= "Xaa = hydrophobic amino acid
                selected from Ala, Leu, Ile, Val, Pro,
                Phe, Trp or Met"

(ix) FEATURE:
        (A) NAME/KEY: Modified-site
        (B) LOCATION: 17
        (D) OTHER INFORMATION: /product= "OTHER"
            /note= "Xaa = Ile or Leu"

(xi) SEQUENCE DESCRIPTION: SEQ ID NO:75:

Tyr Xaa Xaa Xaa Xaa Gly Xaa Xaa Gln Gly Xaa Ile Xaa Ser Xaa Xaa
1               5                  10                 15

Xaa (2) INFORMATION FOR SEQ ID NO:76:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
```

(B) LOCATION: 1
            (D) OTHER INFORMATION: /product= "OTHER"
                /note= "Xaa = Ile or Leu"

(ix) FEATURE:
            (A) NAME/KEY: Modified-site
            (B) LOCATION: 2
            (D) OTHER INFORMATION: /product= "OTHER"
                /note= "Xaa = Leu or Met"

(ix) FEATURE:
            (A) NAME/KEY: Modified-site
            (B) LOCATION: 3
            (D) OTHER INFORMATION: /product= "OTHER"
                /note= "Xaa = Arg or Lys"

(ix) FEATURE:
            (A) NAME/KEY: Modified-site
            (B) LOCATION: 8
            (D) OTHER INFORMATION: /product= "OTHER"
                /note= "Xaa = Tyr or Phe"

(ix) FEATURE:
            (A) NAME/KEY: Modified-site
            (B) LOCATION: 10
            (D) OTHER INFORMATION: /product= "OTHER"
                /note= "Xaa = hydrophobic amino acid
                selected from Ala, Leu, Ile, Val, Pro,
                Phe, Trp or Met"

(ix) FEATURE:
            (A) NAME/KEY: Modified-site
            (B) LOCATION: 11
            (D) OTHER INFORMATION: /product= "OTHER"
                /note= "Xaa = Ile or Val"

(ix) FEATURE:
            (A) NAME/KEY: Modified-site
            (B) LOCATION: 12
            (D) OTHER INFORMATION: /product= "OTHER"
                /note= "Xaa = Thr or Ser"

(xi) SEQUENCE DESCRIPTION: SEQ ID NO:76:

Xaa Xaa Xaa Leu Xaa Asp Asp Xaa Leu Xaa Xaa Xaa
1               5                   10

(2) INFORMATION FOR SEQ ID NO:77:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = Gly or Val"

(ix) FEATURE:
            (A) NAME/KEY: Modified-site
            (B) LOCATION: 4
            (D) OTHER INFORMATION: /product= "OTHER"
                /note= "Xaa = charged amino acid
                selected from Asp, Glu, His, Lys or Arg"

(ix) FEATURE:
            (A) NAME/KEY: Modified-site
            (B) LOCATION: 6
            (D) OTHER INFORMATION: /product= "OTHER"
                /note= "Xaa = polar amino acid
                selected from Gly, Ser, Thr, Tyr, Cys,
                Asn or Gln"

(ix) FEATURE:
         (A) NAME/KEY: Modified-site
         (B) LOCATION: 10
         (D) OTHER INFORMATION: /product= "OTHER"
             /note= "Xaa = Asn or Ser"

(xi) SEQUENCE DESCRIPTION: SEQ ID NO:77:

Xaa Xaa Xaa Xaa Xaa Xaa Xaa Xaa Xaa Xaa Xaa Arg Lys Xaa Xaa Xaa
1               5                   10                  15

(2) INFORMATION FOR SEQ ID NO:78:

(i) SEQUENCE CHARACTERISTICS:
         (A) LENGTH: 34 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Ile or Leu"

(ix) FEATURE:
         (A) NAME/KEY: Modified-site
         (B) LOCATION: 7
         (D) OTHER INFORMATION: /product= "OTHER"
             /note= "Xaa = hydrophobic amino acid
             selected from Ala, Leu, Ile, Val, Pro,
             Phe, Trp or Met"

(ix) FEATURE:
         (A) NAME/KEY: Modified-site
         (B) LOCATION: 8
         (D) OTHER INFORMATION: /product= "OTHER"
             /note= "Xaa = hydrophobic amino acid
             selected from Ala, Leu, Ile, Val, Pro,
             Phe, Trp or Met"

(ix) FEATURE:
         (A) NAME/KEY: Modified-site
         (B) LOCATION: 10
         (D) OTHER INFORMATION: /product= "OTHER"
             /note= "Xaa = hydrophobic amino acid
             selected from Ala, Leu, Ile, Val, Pro,
             Phe, Trp or Met"

(ix) FEATURE:
         (A) NAME/KEY: Modified-site
         (B) LOCATION: 11
         (D) OTHER INFORMATION: /product= "OTHER"
             /note= "Xaa = hydrophobic amino acid
             selected from Ala, Leu, Ile, Val, Pro,
             Phe, Trp or Met"

(ix) FEATURE:
         (A) NAME/KEY: Modified-site
         (B) LOCATION: 12
         (D) OTHER INFORMATION: /product= "OTHER"
             /note= "Xaa = Arg or Gln"

(ix) FEATURE:
         (A) NAME/KEY: Modified-site
         (B) LOCATION: 13
         (D) OTHER INFORMATION: /product= "OTHER"
             /note= "Xaa = polar amino acid
             selected from Gly, Ser, Thr, Tyr, Cys,
             Asn or Gln"

(ix) FEATURE:
         (A) NAME/KEY: Modified-site
         (B) LOCATION: 21
         (D) OTHER INFORMATION: /product= "OTHER"
             /note= "Xaa = polar amino acid

```
            selected from Gly, Ser, Thr, Tyr, Cys,
            Asn or Gln"

(ix) FEATURE:
         (A) NAME/KEY: Modified-site
         (B) LOCATION: 25
         (D) OTHER INFORMATION: /product= "OTHER"
             /note= "Xaa = polar amino acid
             selected from Gly, Ser, Thr, Tyr, Cys,
             Asn or Gln"

(ix) FEATURE:
         (A) NAME/KEY: Modified-site
         (B) LOCATION: 28
         (D) OTHER INFORMATION: /product= "OTHER"
             /note= "Xaa = Tyr or Phe"

(ix) FEATURE:
         (A) NAME/KEY: Modified-site
         (B) LOCATION: 29
         (D) OTHER INFORMATION: /product= "OTHER"
             /note= "Xaa = Tyr or Phe"

(ix) FEATURE:
         (A) NAME/KEY: Modified-site
         (B) LOCATION: 31
         (D) OTHER INFORMATION: /product= "OTHER"
             /note= "Xaa = Lys or His"

(xi) SEQUENCE DESCRIPTION: SEQ ID NO:78:

Trp Xaa Xaa Xaa Xaa Xaa Xaa Xaa Xaa Xaa Xaa Xaa Xaa Phe Phe Tyr
1               5                   10                  15

Ile Thr Glu Xaa Xaa Xaa Xaa Xaa Xaa Xaa Xaa Xaa Xaa Arg Xaa Xaa
            20                  25                  30

Xaa Trp (2) INFORMATION FOR SEQ ID NO:79:

(i) SEQUENCE CHARACTERISTICS:
         (A) LENGTH: 35 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = Ile or Leu"

(ix) FEATURE:
         (A) NAME/KEY: Modified-site
         (B) LOCATION: 7
         (D) OTHER INFORMATION: /product= "OTHER"
             /note= "Xaa = hydrophobic amino acid
             selected from Ala, Leu, Ile, Val, Pro,
             Phe, Trp or Met"

(ix) FEATURE:
         (A) NAME/KEY: Modified-site
         (B) LOCATION: 8
         (D) OTHER INFORMATION: /product= "OTHER"
             /note= "Xaa = hydrophobic amino acid
             selected from Ala, Leu, Ile, Val, Pro,
             Phe, Trp or Met"

(ix) FEATURE:
         (A) NAME/KEY: Modified-site
         (B) LOCATION: 10
         (D) OTHER INFORMATION: /product= "OTHER"
             /note= "Xaa = hydrophobic amino acid
             selected from Ala, Leu, Ile, Val, Pro,
             Phe, Trp or Met"
```

(ix) FEATURE:
        (A) NAME/KEY: Modified-site
        (B) LOCATION: 11
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 12
        (D) OTHER INFORMATION: /product= "OTHER"
            /note= "Xaa = Arg or Gln"

(ix) FEATURE:
        (A) NAME/KEY: Modified-site
        (B) LOCATION: 13
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
        (A) NAME/KEY: Modified-site
        (B) LOCATION: 21
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
        (A) NAME/KEY: Modified-site
        (B) LOCATION: 25
        (D) OTHER INFORMATION: /product= "OTHER"
            /note= "Xaa = polar amino acid
            selected from Gly, Ser, Thr, Tyr, Cys,
            Asn or Gln"

(ix) FEATURE:
        (A) NAME/KEY: Modified-site
        (B) LOCATION: 29
        (D) OTHER INFORMATION: /product= "OTHER"
            /note= "Xaa = Tyr or Phe"

(ix) FEATURE:
        (A) NAME/KEY: Modified-site
        (B) LOCATION: 30
        (D) OTHER INFORMATION: /product= "OTHER"
            /note= "Xaa = Tyr or Phe"

(ix) FEATURE:
        (A) NAME/KEY: Modified-site
        (B) LOCATION: 32
        (D) OTHER INFORMATION: /product= "OTHER"
            /note= "Xaa = Lys or His"

(xi) SEQUENCE DESCRIPTION: SEQ ID NO:79:

Trp Xaa Xaa Xaa Xaa Xaa Xaa Xaa Xaa Xaa Xaa Xaa Xaa Phe Phe Tyr
1               5                   10                  15

Ile Thr Glu Xaa Xaa Xaa Xaa Xaa Xaa Xaa Xaa Xaa Xaa Xaa Arg Xaa
            20                  25                  30

Xaa Xaa Trp
        35

(2) INFORMATION FOR SEQ ID NO:80:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide

```
    (ix) FEATURE:
        (A) NAME/KEY: Modified-site
        (B) LOCATION: 1
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 3
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 4
        (D) OTHER INFORMATION: /product= "OTHER"
            /note= "Xaa = Ile or Leu"

(ix) FEATURE:
        (A) NAME/KEY: Modified-site
        (B) LOCATION: 9
        (D) OTHER INFORMATION: /product= "OTHER"
            /note= "Xaa = polar amino acid
            selected from Gly, Ser, Thr, Tyr, Cys,
            Asn or Gln"

(xi) SEQUENCE DESCRIPTION: SEQ ID NO:80:

Xaa Arg Xaa Xaa Pro Lys Xaa Asn Xaa
1               5

(2) INFORMATION FOR SEQ ID NO:81:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /note= "Xaa = Tyr or Phe"

(ix) FEATURE:
        (A) NAME/KEY: Modified-site
        (B) LOCATION: 6
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 10
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 13
        (D) OTHER INFORMATION: /product= "OTHER"
            /note= "Xaa = Cys or Ala"

(ix) FEATURE:
        (A) NAME/KEY: Modified-site
        (B) LOCATION: 17
        (D) OTHER INFORMATION: /product= "OTHER"
            /note= "Xaa = Ile or Val"
```

(xi) SEQUENCE DESCRIPTION: SEQ ID NO:81:

Pro Arg Xaa Xaa Phe Xaa Xaa Asp Asp Xaa Xaa Xaa Xaa Tyr Asp Xaa
1               5                   10                  15

Xaa (2) INFORMATION FOR SEQ ID NO:82:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = Arg or Gln"

(ix) FEATURE:
        (A) NAME/KEY: Modified-site
        (B) LOCATION: 7
        (D) OTHER INFORMATION: /product= "OTHER"
            /note= "Xaa = Ile or Leu"

(ix) FEATURE:
        (A) NAME/KEY: Modified-site
        (B) LOCATION: 8
        (D) OTHER INFORMATION: /product= "OTHER"
            /note= "Xaa = Pro or Phe"

(ix) FEATURE:
        (A) NAME/KEY: Modified-site
        (B) LOCATION: 11
        (D) OTHER INFORMATION: /product= "OTHER"
            /note= "Xaa = Ser or Leu"

(ix) FEATURE:
        (A) NAME/KEY: Modified-site
        (B) LOCATION: 13
        (D) OTHER INFORMATION: /product= "OTHER"
            /note= "Xaa = Leu or Val"

(ix) FEATURE:
        (A) NAME/KEY: Modified-site
        (B) LOCATION: 16
        (D) OTHER INFORMATION: /product= "OTHER"
            /note= "Xaa = hydrophobic amino acid
                selected from Ala, Leu, Ile, Val, Pro,
                Phe, Trp or Met"

(ix) FEATURE:
        (A) NAME/KEY: Modified-site
        (B) LOCATION: 17
        (D) OTHER INFORMATION: /product= "OTHER"
            /note= "Xaa = Ile or Leu"

(xi) SEQUENCE DESCRIPTION: SEQ ID NO:82:

Tyr Xaa Xaa Xaa Xaa Gly Xaa Xaa Gln Gly Xaa Ser Xaa Ser Xaa Xaa
1               5                   10                  15

Xaa (2) INFORMATION FOR SEQ ID NO:83:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = Ile or Leu"

(ix) FEATURE:
         (A) NAME/KEY: Modified-site
         (B) LOCATION: 2
         (D) OTHER INFORMATION: /product= "OTHER"
             /note= "Xaa = Leu or Met"

(ix) FEATURE:
         (A) NAME/KEY: Modified-site
         (B) LOCATION: 3
         (D) OTHER INFORMATION: /product= "OTHER"
             /note= "Xaa = Arg or Lys"

(ix) FEATURE:
         (A) NAME/KEY: Modified-site
         (B) LOCATION: 8
         (D) OTHER INFORMATION: /product= "OTHER"
             /note= "Xaa = Tyr or Phe"

(ix) FEATURE:
         (A) NAME/KEY: Modified-site
         (B) LOCATION: 10
         (D) OTHER INFORMATION: /product= "OTHER"
             /note= "Xaa = hydrophobic amino acid
             selected from Ala, Leu, Ile, Val, Pro,
             Phe, Trp or Met"

(ix) FEATURE:
         (A) NAME/KEY: Modified-site
         (B) LOCATION: 11
         (D) OTHER INFORMATION: /product= "OTHER"
             /note= "Xaa = Ile or Val"

(ix) FEATURE:
         (A) NAME/KEY: Modified-site
         (B) LOCATION: 12
         (D) OTHER INFORMATION: /product= "OTHER"
             /note= "Xaa = Leu or Val"

(xi) SEQUENCE DESCRIPTION: SEQ ID NO:83:

Xaa Xaa Xaa Phe Xaa Asp Asp Xaa Leu Xaa Xaa Xaa
1               5                   10

(2) INFORMATION FOR SEQ ID NO:84:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = Gly or Val"

(ix) FEATURE:
         (A) NAME/KEY: Modified-site
         (B) LOCATION: 4
         (D) OTHER INFORMATION: /product= "OTHER"
             /note= "Xaa = charged amino acid
             selected from Asp, Glu, His, Lys or Arg"

(ix) FEATURE:
         (A) NAME/KEY: Modified-site
         (B) LOCATION: 6
         (D) OTHER INFORMATION: /product= "OTHER"

```
                /note= "Xaa = polar amino acid
                 selected from Gly, Ser, Thr, Tyr, Cys,
                 Asn or Gln"

(ix) FEATURE:
         (A) NAME/KEY: Modified-site
         (B) LOCATION: 10
         (D) OTHER INFORMATION: /product= "OTHER"
             /note= "Xaa = Asn or Ser"

(xi) SEQUENCE DESCRIPTION: SEQ ID NO:84:

Xaa Xaa Xaa Xaa Xaa Xaa Xaa Xaa Xaa Xaa Xaa Gln Lys Xaa Xaa Xaa
1               5                   10                  15

(2) INFORMATION FOR SEQ ID NO:85:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = hydrophobic amino acid
              selected from Ala, Leu, Ile, Val, Pro,
              Phe, Trp or Met"

(ix) FEATURE:
         (A) NAME/KEY: Modified-site
         (B) LOCATION: 5
         (D) OTHER INFORMATION: /product= "OTHER"
             /note= "Xaa = Phe or Tyr"

(xi) SEQUENCE DESCRIPTION: SEQ ID NO:85:

Xaa Xaa Asp Asp Xaa
1               5

(2) INFORMATION FOR SEQ ID NO:86:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = Phe or Tyr"

(ix) FEATURE:
         (A) NAME/KEY: Modified-site
         (B) LOCATION: 5
         (D) OTHER INFORMATION: /product= "OTHER"
             /note= "Xaa = hydrophobic amino acid
              selected from Ala, Leu, Ile, Val, Pro,
              Phe, Trp or Met"

(xi) SEQUENCE DESCRIPTION: SEQ ID NO:86:

Xaa Xaa Asp Asp Xaa
1               5

(2) INFORMATION FOR SEQ ID NO:87:

(i) SEQUENCE CHARACTERISTICS:
```

(A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:87:

Trp Xaa Gly Xaa
1

(2) INFORMATION FOR SEQ ID NO:88:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 6
        (D) OTHER INFORMATION: /product= "OTHER"
            /note= "Xaa = hydrophobic amino acid
            selected from Ala, Leu, Ile, Val, Pro,
            Phe, Trp or Met"

(xi) SEQUENCE DESCRIPTION: SEQ ID NO:88:

Xaa Leu Gly Xaa Xaa Xaa
1               5

(2) INFORMATION FOR SEQ ID NO:89:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:89:

Trp Xaa Xaa Xaa Xaa Xaa Xaa Xaa Xaa Xaa Xaa Xaa Xaa Phe Phe Tyr
1               5                   10                  15

Xaa Thr Glu Xaa Xaa Xaa Xaa Xaa Xaa Xaa Xaa Xaa Xaa Arg Xaa Xaa
            20                  25                  30

Xaa Trp (2) INFORMATION FOR SEQ ID NO:90:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:90:

Trp Xaa Xaa Xaa Xaa Xaa Xaa Xaa Xaa Xaa Xaa Xaa Xaa Phe Phe Tyr

```
            1               5                  10                 15
         Xaa Thr Glu Xaa Xaa Xaa Xaa Xaa Xaa Xaa Xaa Xaa Xaa Arg Xaa
                     20                  25                  30

Xaa Xaa Trp
                 35

(2) INFORMATION FOR SEQ ID NO:91:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Leu or Ile"

(ix) FEATURE:
        (A) NAME/KEY: Modified-site
        (B) LOCATION: 10
        (D) OTHER INFORMATION: /product= "OTHER"
            /note= "Xaa = Leu or Ile"

(ix) FEATURE:
        (A) NAME/KEY: Modified-site
        (B) LOCATION: 11
        (D) OTHER INFORMATION: /product= "OTHER"
            /note= "Xaa = Leu or Ile"

(ix) FEATURE:
        (A) NAME/KEY: Modified-site
        (B) LOCATION: 12
        (D) OTHER INFORMATION: /product= "OTHER"
            /note= "Xaa = Gln or Arg"

(ix) FEATURE:
        (A) NAME/KEY: Modified-site
        (B) LOCATION: 28
        (D) OTHER INFORMATION: /product= "OTHER"
            /note= "Xaa = Phe or Tyr"

(ix) FEATURE:
        (A) NAME/KEY: Modified-site
        (B) LOCATION: 29
        (D) OTHER INFORMATION: /product= "OTHER"
            /note= "Xaa = Phe or Tyr"

(ix) FEATURE:
        (A) NAME/KEY: Modified-site
        (B) LOCATION: 31
        (D) OTHER INFORMATION: /product= "OTHER"
            /note= "Xaa = Lys or His"

(xi) SEQUENCE DESCRIPTION: SEQ ID NO:91:

Trp Xaa Xaa Xaa Xaa Xaa Xaa Xaa Xaa Xaa Xaa Xaa Xaa Phe Phe Trp
1               5                  10                  15

Xaa Thr Glu Xaa Xaa Xaa Xaa Xaa Xaa Xaa Xaa Xaa Xaa Arg Xaa Xaa
            20                  25                  30

Xaa Trp (2) INFORMATION FOR SEQ ID NO:92:

(i) SEQUENCE CHARACTERISTICS:
        (A) LENGTH: 35 amino acids
        (B) TYPE: amino acid
        (C) STRANDEDNESS:
        (D) TOPOLOGY: linear
```

(ii) MOLECULE TYPE: peptide (ix) FEATURE:
            (A) NAME/KEY: Modified-site
            (B) LOCATION: 2
            (D) OTHER INFORMATION: /product= "OTHER"
                /note= "Xaa = Leu or Ile"

(ix) FEATURE:
            (A) NAME/KEY: Modified-site
            (B) LOCATION: 10
            (D) OTHER INFORMATION: /product= "OTHER"
                /note= "Xaa = Leu or Ile"

(ix) FEATURE:
            (A) NAME/KEY: Modified-site
            (B) LOCATION: 11
            (D) OTHER INFORMATION: /product= "OTHER"
                /note= "Xaa = Leu or Ile"

(ix) FEATURE:
            (A) NAME/KEY: Modified-site
            (B) LOCATION: 12
            (D) OTHER INFORMATION: /product= "OTHER"
                /note= "Xaa = Gln or Arg"

(ix) FEATURE:
            (A) NAME/KEY: Modified-site
            (B) LOCATION: 29
            (D) OTHER INFORMATION: /product= "OTHER"
                /note= "Xaa = Phe or Tyr"

(ix) FEATURE:
            (A) NAME/KEY: Modified-site
            (B) LOCATION: 30
            (D) OTHER INFORMATION: /product= "OTHER"
                /note= "Xaa = Phe or Tyr"

(ix) FEATURE:
            (A) NAME/KEY: Modified-site
            (B) LOCATION: 32
            (D) OTHER INFORMATION: /product= "OTHER"
                /note= "Xaa = Lys or His"

(xi) SEQUENCE DESCRIPTION: SEQ ID NO:92:

Trp Xaa Xaa Xaa Xaa Xaa Xaa Xaa Xaa Xaa Xaa Xaa Xaa Phe Phe Trp
1               5                   10                  15

Xaa Thr Glu Xaa Xaa Xaa Xaa Xaa Xaa Xaa Xaa Xaa Xaa Xaa Arg Xaa
            20                  25                  30

Xaa Xaa Trp
        35

(2) INFORMATION FOR SEQ ID NO:93:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:93:

Leu Arg Xaa Xaa Pro Lys Xaa Xaa Xaa
1               5

(2) INFORMATION FOR SEQ ID NO:94:

(i) SEQUENCE CHARACTERISTICS:
        (A) LENGTH: 9 amino acids
        (B) TYPE: amino acid
        (C) STRANDEDNESS:

(D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 3
        (D) OTHER INFORMATION: /product= "OTHER"
            /note= "Xaa = hydrophobic amino acid
            selected from Ala, Leu, Ile, Val, Pro,
            Phe, Trp or Met"

(xi) SEQUENCE DESCRIPTION: SEQ ID NO:94:

Xaa Arg Xaa Ile Pro Lys Xaa Xaa Xaa
1               5

(2) INFORMATION FOR SEQ ID NO:95:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:95:

Xaa Arg Xaa Ile Xaa
1               5

(2) INFORMATION FOR SEQ ID NO:96:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:96:

Xaa Xaa Xaa Xaa Phe Xaa Xaa Xaa Asp Xaa Xaa Xaa Xaa Tyr Asp Xaa
1               5                   10                  15

Xaa (2) INFORMATION FOR SEQ ID NO:97:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:

(A) NAME/KEY: Modified-site
        (B) LOCATION: 8
        (D) OTHER INFORMATION: /product= "OTHER"
            /note= "Xaa = hydrophobic amino acid
            selected from Ala, Leu, Ile, Val, Pro,
            Phe, Trp or Met"

(ix) FEATURE:
        (A) NAME/KEY: Modified-site
        (B) LOCATION: 10
        (D) OTHER INFORMATION: /product= "OTHER"
            /note= "Xaa = hydrophobic amino acid
            selected from Ala, Leu, Ile, Val, Pro,
            Phe, Trp or Met"

(xi) SEQUENCE DESCRIPTION: SEQ ID NO:97:

Pro Xaa Leu Tyr Phe Xaa Xaa Xaa Asp Xaa Xaa Xaa Xaa Tyr Asp Xaa
1               5                   10                  15

Ile (2) INFORMATION FOR SEQ ID NO:98:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:98:

Tyr Xaa Xaa Xaa Xaa Gly Xaa Xaa Gln Gly Xaa Xaa Xaa Ser Xaa Xaa
1               5                   10                  15

Xaa Xaa Xaa Xaa Xaa Xaa
            20

(2) INFORMATION FOR SEQ ID NO:99:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /product= "OTHER"
            /note= "Xaa = hydrophobic amino acid
            selected from Ala, Leu, Ile, Val, Pro,
            Phe, Trp or Met"

(xi) SEQUENCE DESCRIPTION: SEQ ID NO:99:

Gln Xaa Xaa Gly Ile Pro Gln Gly Ser Xaa Leu Ser Xaa Xaa Leu
1               5                   10                  15

(2) INFORMATION FOR SEQ ID NO:100:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:100:

Xaa Xaa Xaa Xaa Xaa Xaa Asp Asp Xaa Leu Xaa Xaa Xaa

```
1               5               10
(2) INFORMATION FOR SEQ ID NO:101:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:101:

Leu Leu Arg Phe Xaa Asp Asp Phe Leu Leu Xaa Thr
1               5                   10
```